(12) United States Patent
Bengtsson et al.

(10) Patent No.: US 11,195,606 B2
(45) Date of Patent: Dec. 7, 2021

(54) SYSTEMS AND METHODS FOR THE DETERMINATION OF INSULIN SENSITIVITY

(71) Applicant: Novo Nordisk A/S, Bagsvaerd (DK)

(72) Inventors: Henrik Bengtsson, Taastrup (DK); Tinna Bjoerk Aradottir, Copenhagen (DK); Pete Brockmeier, Copenhagen (DK)

(73) Assignee: Novo Nordisk A/S, Bagsvaerd (DK)

( * ) Notice: Subject to any disclaimer, the term of this patent is extended or adjusted under 35 U.S.C. 154(b) by 381 days.

(21) Appl. No.: 16/315,820

(22) PCT Filed: Jun. 22, 2017

(86) PCT No.: PCT/EP2017/065378
§ 371 (c)(1),
(2) Date: Jan. 7, 2019

(87) PCT Pub. No.: WO2018/007160
PCT Pub. Date: Jan. 11, 2018

(65) Prior Publication Data
US 2019/0228853 A1    Jul. 25, 2019

(30) Foreign Application Priority Data
Jul. 8, 2016 (EP) .................................. 16178558

(51) Int. Cl.
*G16H 20/17* (2018.01)
*G16H 10/40* (2018.01)
(Continued)

(52) U.S. Cl.
CPC .......... *G16H 20/17* (2018.01); *A61M 5/1723* (2013.01); *G16H 10/40* (2018.01); *A61B 5/4836* (2013.01); *G16H 40/40* (2018.01)

(58) Field of Classification Search
USPC .............................................................. 705/2
See application file for complete search history.

(56) References Cited

U.S. PATENT DOCUMENTS 6,544,212 B2 * 4/2003 Galley ................... G16H 20/17
604/31
7,404,796 B2   7/2008 Ginsberg
(Continued)

FOREIGN PATENT DOCUMENTS

AU    2015/100005 A4    2/2015
WO    2005000209 A2    1/2005
(Continued)

OTHER PUBLICATIONS

Bao, et al., "Improving the Estimation of Mealtime Insulin Dose in Adults with Type 1 Diabetes", Diabetes Care, Oct. 2011, vol. 34, pp. 2146-2151; (Year: 2011).*
(Continued)

*Primary Examiner* — Amber A Misiaszek
(74) *Attorney, Agent, or Firm* — Wesley Nicolas

(57) ABSTRACT

A subject is prescribed short and long acting insulin medicament regimens. When a qualified fasting event occurs, the basal insulin sensitivity estimate of the subject is updated using (i) an expected fasting blood glucose level based upon the long acting insulin medicament dosing specified by the long acting regimen during the fasting event, (ii) glucose measurements contemporaneous with the fasting event and (iii) a prior insulin sensitivity factor. A basal insulin sensitivity factor curve is calculated from the updated basal insulin sensitivity estimate. A bolus insulin sensitivity estimate of the subject is updated upon occurrence of a correction bolus with a short acting insulin medicament using (i) an expected blood glucose level based upon the correction bolus, (ii) glucose measurements after occurrence of the correction bolus, and (iii) a prior insulin sensitivity factor. A
(Continued)

bolus insulin sensitivity factor curve is calculated from the updated bolus insulin sensitivity estimate.

11 Claims, 18 Drawing Sheets

(51) Int. Cl.
  *A61M 5/172* (2006.01)
  *A61B 5/00* (2006.01)
  *G16H 40/40* (2018.01)

(56) References Cited

U.S. PATENT DOCUMENTS

| | | | |
|---|---|---|---|
| 8,370,077 B2 | 2/2013 | Bashan et al. | |
| 2005/0203360 A1* | 9/2005 | Brauker | A61B 5/7257 600/345 |
| 2009/0036753 A1 | 2/2009 | King | |
| 2010/0262434 A1 | 10/2010 | Shaya | |
| 2011/0098548 A1* | 4/2011 | Budiman | G16Z 99/00 600/365 |
| 2011/0257496 A1 | 10/2011 | Terashima et al. | |
| 2012/0232520 A1 | 9/2012 | Sloan et al. | |
| 2013/0165901 A1* | 6/2013 | Ruchti | G16H 50/20 604/504 |
| 2013/0338629 A1* | 12/2013 | Agrawal | G16H 50/70 604/504 |
| 2014/0343530 A1 | 11/2014 | Bashan et al. | |
| 2016/0162797 A1 | 6/2016 | Thorpe et al. | |
| 2019/0348164 A1 | 11/2019 | Bengtsson et al. | |

FOREIGN PATENT DOCUMENTS

| | | |
|---|---|---|
| WO | 2010/072386 A2 | 7/2010 |
| WO | 2012/122520 A1 | 9/2012 |
| WO | 2013/096769 A1 | 6/2013 |

OTHER PUBLICATIONS

Medtronic Minimed: "Paradigm 522 and 722 Insulin Pumps. User Guide", Internet Citation, Nov. 21, 2006, pp. 1-176, XP002495154, Retrieved from the Internet: URL:http:www.minimed.com/pdf/x22_user_guide.pdf, retrieved on Jan. 5, 2016.

R. M. Bergenstal et al: "Adjust to Target in Type 2 Diabetes: Comparison of a simple algorithm with carbohydrate counting for adjustment of mealtime insulin glulisine", Diabetes Care, 2008, vol. 31 , No. 7, pp. 1305-1310.

Herrero et al., "Advanced insulin bolus advisor based on run-to-run control and case-based reasoning," IEEE Journal of Biomedical and Health Informatics, May 2015, vol. 19, No. 3, pp. 1087-1096.

* cited by examiner

428

Make a bolus insulin sensitivity estimate ($ISF_{bolus,i,t}$) 232 upon occurrence of a correction bolus with a short acting insulin medicament using (i) an expected blood glucose level ($BG_{expected}$) based upon the correction bolus with the short acting insulin medicament, (ii) the glucose level ($\widehat{BG}_{corr,i}$) of the subject after occurrence of the correction bolus, wherein $\widehat{BG}_{corr,i}$ is obtained from the portion of the plurality of glucose measurements that is contemporaneous with a period of time after the occurrence of the correction bolus, and (iii) a bolus insulin sensitivity factor ($ISF_{bolus,i-p,t}$) of the subject estimated based upon occurrence of a prior correction bolus with the short acting insulin medicament.

430

$$ISF_{bolus,i,t} = \left(\frac{BG_{expected} - \widehat{BG}_{corr,i}}{\widehat{BG}_{corr,i}} + 1\right) ISF_{bolus,i-p,t}$$

432

Estimate a bolus insulin sensitivity factor curve ($ISF_{bolus,i}$) 236.

434

The estimating the bolus sensitivty factor curve ($ISF_{bolus,i}$) 236 comprises computing:

$$ISF_{bolus,i} = \left(\frac{ISF_{bolus,i,t} - ISF_{bolus,i-p,t}}{ISF_{bolus,i,t}} + 1\right) ISF_{bolus,i-p}.$$

436

Estimate the basal insulin sensitivity curve ($ISF_{basal,i}$) 234 as a function of the estimated bolus insulin sensitivity estimate ($ISF_{bolus,i,t}$) 232.

438

The estimating the ($ISF_{basal,i}$) 234 as a function of the estimated bolus insulin sensitivity estimate ($ISF_{bolus,i,t}$) 232 comprises computing:

$$ISF_{basal,i} = \left(\frac{ISF_{bolus,i,t} - ISF_{bolus,i-p,t}}{ISF_{bolus,i,t}} + 1\right) ISF_{basal,i-p}.$$

440

Update the bolus insulin sensitivity curve ($ISF_{bolus}$) as a function of the estimated bolus insulin sensitivity factor curve ($ISF_{bolus,i}$) and prior estimated bolus insulin sensitivity factor curves for the subject.

442

$$ISF_{bolus} = \sum_{n=i-q}^{i} w_n ISF_{bolus,n},$$

where, q is a predetermined number of historical updates to $ISF_{bolus}$, w is a linear or nonlinear vector of normalised weights, n is an integer index into the historical updates to $ISF_{bolus}$ and vector w, and $ISF_{bolus,n}$ is an $n^{th}$ past $ISF_{bolus}$ calculation.

Fig. 4C

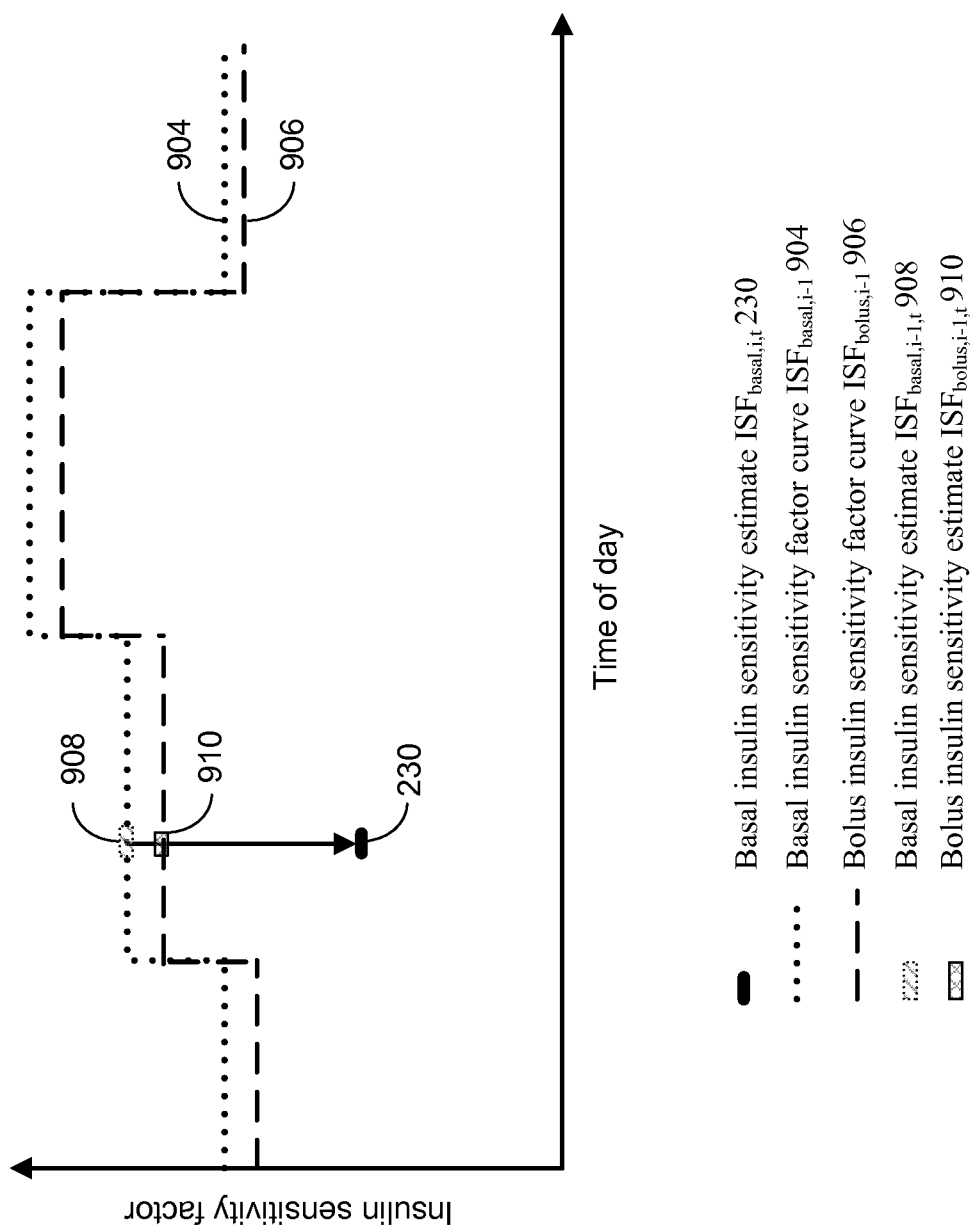

SYSTEMS AND METHODS FOR THE DETERMINATION OF INSULIN SENSITIVITY

CROSS-REFERENCE TO RELATED APPLICATIONS

This application is a 35 U.S.C. § 371 National Stage application of International Application PCT/EP2017/065378 (published as WO 2018/007160), filed Jun. 22, 2017, which claims priority to European Patent Application 16178558.9, filed Jul. 8, 2016, the contents of all above-named applications are incorporated herein by reference.

TECHNICAL FIELD

The present disclosure relates generally to systems, methods and computer programs for assisting patients and health care practitioners in estimating insulin sensitivity and using such information for purposes such as providing a recommended dose of a short acting insulin medicament to achieve a target fasting glucose level in a subject.

BACKGROUND

Type 2 diabetes mellitus is characterized by progressive disruption of normal physiologic insulin secretion. In healthy individuals, basal insulin secretion by pancreatic β cells occurs continuously to maintain steady glucose levels for extended periods between meals. Also in healthy individuals, there is prandial secretion in which insulin is rapidly released in an initial first-phase spike in response to a meal, followed by prolonged insulin secretion that returns to basal levels after 2-3 hours.

Insulin is a hormone that binds to insulin receptors to lower blood glucose by facilitating cellular uptake of glucose, amino acids, and fatty acids into skeletal muscle and fat and by inhibiting the output of glucose from the liver. In normal healthy individuals, physiologic basal and prandial insulin secretions maintain euglycemia, which affects fasting plasma glucose and postprandial plasma glucose concentrations. Basal and prandial insulin secretion is impaired in Type 2 diabetes and early post-meal response is absent. To address these adverse events, patients with Type 2 diabetes are provided with insulin treatment regimens. Patients with Type 1 diabetes are also provided with insulin treatment regimens.

Some diabetic patients only need a basal insulin treatment regimen to make up for deficiencies in pancreatic β cells insulin secretion. Other diabetic patients need both basal and bolus insulin treatment.

Patients that require both basal and bolus insulin treatment take a periodic basal insulin medicament treatment, for instance once or twice a day, as well as one or more bolus insulin medicament treatments with meals. Such multiple daily injection (MDI) insulin therapy usually involves injections of fast acting insulin before each meal and long-acting insulin once to twice per day. Most patients undergoing insulin therapy for managing their diabetes have difficulty determining how much insulin they need. The size of a dose depends on how many carbohydrates the patient consumed over a particular period, how far their current blood glucose levels are from a target level, as well as current physiological state such as insulin sensitivity. Traditionally, two parameters are used to calculate fast-acting insulin doses (i) insulin sensitivity factor (ISF), which is used to calculate how much insulin is needed to move glucose levels to a desired target, and (ii) carb-to-insulin ratio (CIR), which is used to calculate how much insulin is needed to account for a meal. Since these factors are used to calculate the amount of insulin medicament to dose, it is important that they are correct and relate to the current physiological state of the patient. Otherwise, the dosing will be imprecise and result in suboptimal treatment and episodes of hyper- and hypoglycaemic events.

Patients' physiological state affects their insulin sensitivity and thereby how much insulin they need to account for meals and too high glucose levels. Situations where insulin sensitivity changes include periods of illness (e.g. fever, influenza etc.) at which time insulin sensitivity typically decreases. They also include periods of high levels of physical activity, at which time insulin sensitivity typically increases. They further include periods of high levels of stress, which can cause insulin sensitivity to decrease, but typically recovers after the stress has passed. Patients experience a high level of difficulty during these periods in controlling their blood glucose levels. Their predefined parameters do not apply for dose calculations and they experience hyper- and hypoglycaemic events and a feeling of loss of control.

Determining patient ISF and CIR values is a challenge to health care professionals and patients and it requires extensive work. For a health care professional to accurately estimate the ISF, the HCP needs access to extensive and reliable data including glucose measurement data, insulin doses, as well as other information that may affect the patients' physiological state. This data needs to be provided by the patient, which is time consuming and inconvenient. Many health care professionals have difficulty determining ISF from all of the data and tend to guess at the value based upon only one or two data points. Furthermore, the patient may not have sufficiently frequent access to a health care professional to make adequate adjustments to the patient's diabetes management formula and/or its various factors. Furthermore, health care professionals and patients cannot calculate insulin sensitivity frequently enough to capture changes during periods of stress, illness etc.

Conventional automated dose calculators typically update the ISF estimate based on glucose response to fast acting insulin, either following a meal-related dose or a correction bolus. This poses problems. For instance, if the ISF is estimated based on meal-related doses, high uncertainty may be expected due to the high uncertainty in CHO-counting. If the ISF is estimated based on a correction bolus only, this requires that a correction bolus is taken frequently. If this is not done, for instance because the patient is in relatively good glycaemic control, the ISF is not updated frequently and periods of increased insulin sensitivity may not be detected.

WO 2012/122520 discloses that patient's using long-acting insulin may have different sensitivity to insulin. It further discloses that measurements of a fasting blood glucose level can be measured and compared to a predetermined threshold value, that a dosage recommendation algorithm can be used to estimate a dose pased on the fasting blood glucose level and the threshold value. The document also discloses that a measurement of the blood glucose level can be used to titrate the long-acting insulin dose until a threshold range is achieved. WO 2012/122520 further shows that a patient's insulin sensitivity can be based on the patient's fasting blood glucose level and the fasting insulin level. However, WO 2012/122520 does not solve the problem of ensuring that parameters for dose estimation is frequently updated, in particular if no correction bolus is taken.

Given the above background, what is needed in the art are systems and methods that provide satisfactory ways to estimate parameters in an insulin medicament regimen, such as ISF, CSF, and related parameters.

SUMMARY

The present disclosure addresses the above-identified need in the art by providing methods, devices, computer programs and computer readable carriers having stored thereon computer programs for estimating parameters in an insulin medicament regimen. In particular, embodiments of the present disclosure relate generally to a method and apparatus for assisting patients and health care practitioners in managing insulin treatment to diabetic patients. In one aspect, insulin sensitivity is estimated based on data sets of continuous glucose monitoring data and insulin pen data where at least two types of insulin medicament are used, for instance, a fast acting insulin medicament and a long acting insulin medicament.

In a first aspect of the present disclosure is proved a device for estimating parameters in an insulin medicament regimen for a subject that includes both a short acting insulin medicament regimen and a long acting insulin medicament regimen, and wherein the device comprises one or more processors and a memory, the memory storing instructions that, when executed by the one or more processors, perform a method of:
  A) obtaining:
    A.1) a first data set, the first data set comprising a plurality of glucose measurements of the subject taken over a first period of time and, for each respective glucose measurement in the plurality of glucose measurements, a timestamp representing when the respective measurement was made;
    A.2) a second data set from one or more insulin pens used by the subject to apply the insulin medicament dosage regimen, the second data set comprises a plurality of insulin medicament records, each insulin medicament record in the plurality of medicament records comprises: (i) a respective insulin medicament injection event including an amount of insulin medicament injected into the subject using a respective insulin pen in the one or more insulin pens (ii) a corresponding electronic timestamp that is automatically generated by the respective insulin pen upon occurrence of the respective insulin medicament injection event, and (iii) a type of insulin medicament, wherein the type of insulin medicament is a short acting insulin medicament or a long acting insulin medicament;
  B) determining one or more insulin sensitivity change estimates by:
    B.1) making an estimate of a basal insulin sensitivity change between a basal insulin sensitivity estimate ($ISF_{basal,i,t}$) for the subject related to the occurrence of a first basal insulin related event undertaken by the subject within the first period of time, when the first basal insulin related event is deemed qualified, and a basal insulin sensitivity estimate ($ISF_{basal,i-p,t}$) of the subject related to the occurrence of a qualified basal insulin related event occurring before the first basal insulin related event, wherein the occurrence of the basal insulin related events are identified in the first data set, the estimating the change using:
      (i) the basal insulin sensitivity estimate ($ISF_{basal,i-p,t}$) of the subject related to the occurrence of the qualified basal insulin related event occurring before the first basal insulin related event (ii) glucose measurements from the first data set contemporaneous with the occurrence of the first qualified basal insulin related event, (iii) glucose measurements from the first data set contemporaneous with the occurrence of the qualified basal insulin related event occurring before the first qualified basal insulin related event, (iv) an insulin medicament injection event from the second data set corresponding to the first qualified basal insulin related event, wherein the injection has been applied according to the long acting insulin medicament regimen, and (v) an insulin medicament injection event from the second data set corresponding to the qualified basal insulin related event occurring before the first qualified basal insulin related event, wherein the injection has been applied according to the long acting insulin medicament regimen; and/or
    B.2) making an estimate of a bolus insulin sensitivity change between a bolus insulin sensitivity estimate ($ISF_{bolus,i,t}$) for the subject relating to the occurrence of a correction bolus with a short acting insulin medicament within the first period of time and a bolus insulin sensitivity estimate ($ISF_{bolus,i-p,t}$) of the subject related to the occurrence of a prior correction bolus with the short acting insulin medicament, wherein the occurrence of the correction bolus and the occurrence of the prior correction bolus are identified in the first data set, the estimating the change using: (i) glucose measurements from the first data set contemporaneous with the occurrence of the correction bolus with a short acting medicament, (ii) the bolus insulin sensitivity estimate ($ISF_{bolus,i-p,t}$) of the subject related to the occurrence of a prior correction bolus with the short acting insulin medicament and (iii) an insulin medicament injection event from the second data set corresponding to the occurrence of the correction bolus and applied according to the short acting insulin medicament regimen (214); and
  C) estimating the bolus insulin sensitivity estimate ($ISF_{bolus,i,t}$) as a function of the estimated basal insulin sensitivity change, in response to making an estimate of the basal insulin sensitivity change in B.1); and/or
  D) estimating the basal insulin sensitivity estimate ($ISF_{basal,i,t}$) as a function of the estimated bolus insulin sensitivity change, in response to making an estimate of the bolus insulin sensitivity change in B.2), and
  wherein the insulin sensitivity estimates are parameters in the insulin medicament regimen.

Hereby is provided a more robust ISF estimator based on bolus and basal insulin injections, where a new bolus or basal ISF estimate is based on an estimate of basal or bolus insulin sensitivity change, respectively. In the present disclosure, the insulin sensitivity factor (ISF) can be estimated based on a drop in glucose level following a correction bolus and/or a change in fasting glucose levels response following a basal insulin injection. The identification of a change between the basal insulin sensitivity estimate ($ISF_{basal,i,t}$) of the subject during a first basal insulin related event and the basal insulin sensitivity estimate ($ISF_{basal,i-p,t}$) of the subject during a qualified basal insulin related event occurring before the first basal insulin related event in B.1), enables the estimating of a change in an insulin sensitivity of the subject, wherein the estimated change in insulin sensitivity can be used to calculate a new bolus insulin sensitivity estimate. Similarly, the identification of a change between the bolus insulin sensitivity estimate ($ISF_{bolus,i,t}$) for the subject relating to the occurrence of a correction bolus with a short acting insulin medicament within the first period of time and a bolus insulin sensitivity estimate ($ISF_{bolus,i-p,t}$) of the subject related to the occurrence of a prior correction bolus with the short acting insulin medicament, can be used to calculate a new basal insulin sensitivity estimate. As the bolus insulin sensitivity estimate can be based on an event related to a basal insulin related event, and as the basal insulin sensitivity estimate can be based on an event related to a correction bolus, i.e., a bolus insulin related event, the ISF estimator is more robust, and more frequent parameter updates are enabled. The first and second data set systematically provides timestamped data, and thereby contributes to the reliability of the estimated parameters, and the robustness of the estimator. If for example a change in insulin sensitivity is not detected by the ISF estimator, the next ISF calculation will be less correct, whereas an efficient detection of a change in ISF will increase the validity. Therefore, the density of glucose influences the ability to identify insulin related events, and the injection data provided directly by one or more insulin pens increases the quality of the estimated parameters, as well as it enables adherence categorization based on stamped time-insulin injections.

In a further aspect, the estimated basal insulin sensitivity change is a function of the estimated basal insulin sensitivity estimate ($ISF_{basal,i,t}$) for the subject upon occurrence of the first basal insulin related event and the basal insulin sensitivity factor ($ISF_{basal,i-p,t}$) of the subject during the qualified basal insulin related event occurring before the first bolus insulin relevant event.

In a further aspect, the estimated bolus insulin sensitivity change is a function of the estimated bolus insulin sensitivity estimate ($ISF_{bolus,i,t}$) for the subject upon occurrence of the correction bolus with a short acting insulin medicament and the bolus insulin sensitivity factor ($ISF_{bolus,i-p,t}$) of the subject estimated based upon occurrence of a prior correction bolus with the short acting insulin medicament.

In a further aspect, the method further comprising:
E) estimating a basal insulin sensitivity factor curve ($ISF_{basal,i}$) as a function of the estimated basal insulin change, in response to estimating the basal insulin sensitivity change in B.1) and/or in response to estimating the basal insulin sensitivity estimate in D).

In a further aspect, the estimating the basal insulin sensitivity factor curve ($ISF_{basal,i}$) in E) comprises computing:

$$ISF_{basal,i} = \left( \frac{ISF_{basal,i,t} - ISF_{basal,i-p,t}}{ISF_{basal,i-p,t}} + 1 \right) ISF_{basal,i-p},$$

wherein $ISF_{basal,i-p}$ represents a prior basal sensitivity factor curve estimate.

In a further aspect, the method further comprising:
F) estimating a bolus insulin sensitivity factor curve ($ISF_{bolus,i}$) as a function of (i) the estimated bolus insulin sensitivity change, in response to estimating the bolus insulin sensitivity change in B2) and/or in response to estimating the bolus insulin sensitivity in C).

In a further aspect, the estimating the bolus sensitivity factor curve ($ISF_{bolus,i}$) in F) comprises computing:

$$ISF_{bolus,i} = \left( \frac{ISF_{bolus,i,t} - ISF_{bolus,i-p,t}}{ISF_{bolus,i-p,t}} + 1 \right) ISF_{bolus,i-p},$$

wherein $ISF_{bolus,i-p}$ represents a prior bolus sensitivity factor curve estimate.

In a further aspect, the method further comprising:
G) updating
(i) the bolus insulin sensitivity curve ($ISF_{bolus}$) as a function of the estimated bolus insulin sensitivity factor curve ($ISF_{bolus,i}$) of F) and prior estimated bolus insulin sensitivity factor curves for the subject, and
(ii) updating the basal insulin sensitivity curve ($ISF_{basal}$) as a function of the estimated basal insulin sensitivity factor curve ($ISF_{basal,i}$) of E) and prior estimated basal insulin sensitivity factor curves for the subject; and
H) providing a recommended dose of the short acting insulin medicament to achieve a target fasting glucose level in the subject by using glucose measurements from a portion of the plurality of glucose measurements and the updated bolus insulin sensitivity curve ($ISF_{bolus}$) or the updated basal insulin sensitivity curve ($ISF_{basal}$).

In a further aspect, the estimating the basal insulin sensitivity change for the subject in B.1) is computed as:

$$\left( \frac{ISF_{basal,i}}{ISF_{basal,i-p}} \right) = \left( \frac{FBG_{expected} - \widehat{FBG}_i}{\widehat{FBG}_i} + 1 \right),$$

wherein $FBG_{expected}$ the expected blood glucose level ($FBG_{expected}$) in a period of time during the first qualified basal insulin related event based on (i) the basal insulin sensitivity estimate ($ISF_{basal,i-p,t}$) of the subject related to the occurrence of the qualified basal insulin related event occurring before the first basal insulin related event (ii) the glucose measurements from the first data set contemporaneous with the occurrence of the qualified basal insulin related event occurring before the first qualified basal insulin related event, (iii) the insulin medicament injection event from the second data set corresponding to the first qualified basal insulin related event, and (iv) the insulin medicament injection event from the second data set corresponding to the qualified basal insulin related event occurring before the first qualified basal insulin related event, and wherein $\widehat{FBG}_i$ is the glucose level ($\widehat{FBG}_i$) obtained from the glucose measurements from the first data set contemporaneous with the occurrence of the first qualified basal insulin related event.

In a further aspect, the estimating the basal insulin sensitivity change for the subject in B.1) is computed as:

$$\left( \frac{ISF_{basal,i,t}}{ISF_{basal,i-p,t}} \right) = \left( \frac{\widehat{FBG}_i - \widehat{FBG}_{i-p}}{FBG_{expected} - \widehat{FBG}_{i-p}} \right),$$

wherein $\widehat{FBG}_i$ is the glucose level ($\widehat{FBG}_i$) obtained from the glucose measurements from the first data set contemporaneous with the occurrence of the first qualified basal insulin related event, wherein $FBG_{expected}$ is the expected blood glucose level (FBG$_{expected}$) during the first basal insulin related event based on (i) the basal insulin sensitivity estimate (ISF$_{basal,i-p,t}$) of the subject related to the occurrence of the qualified basal insulin related event occurring before the first basal insulin related event (ii) the glucose measurements from the first data set contemporaneous with the occurrence of the qualified basal insulin related event occurring before the first qualified basal insulin related event, (iii) the insulin medicament injection event from the second data set corresponding to the first qualified basal insulin related event, and (iv) the insulin medicament injection event from the second data set corresponding to the qualified basal insulin related event occurring before the first qualified basal insulin related event, and wherein $\widehat{FBG}_{i-p}$ is the glucose level ($\widehat{FBG}_{i-p}$) obtained from the glucose measurements from the first data set contemporaneous with the occurrence of the qualified basal insulin related event occurring before the first qualified basal insulin related event, and wherein FBG$_{expected}$ is different from $\widehat{FBG}_{i-p}$.

In a further aspect, the expected blood glucose level (FBG$_{expected}$) is computed as:

$$FBG_{expected} = \widehat{FBG}_{basal,i-p} - ISF_{basal,i-p,t}(U_{basal,i} - U_{basal,i-p}),$$

wherein $\widehat{FBG}_{basal,i-p}$ is the glucose level ($\widehat{FBG}_{basal,i-p}$) based on the glucose measurements from the first data set contemporaneous with the occurrence of the qualified basal insulin related event occurring before the first qualified basal insulin related event, wherein U$_{basal,\ i}$ is the amount of insulin medicament (U$_{basal,i}$) corresponding to the insulin medicament injection event from the second data set corresponding to the first qualified basal insulin related event, U$_{basal,\ i-1}$ is the amount of insulin (U$_{basal,i-p}$) corresponding to the insulin medicament injection event from the second data set corresponding to the qualified basal insulin related event occurring before the first qualified basal insulin related event.

In a further aspect, the first basal insulin related event is deemed qualified when (i) the subject has taken no correction bolus of the short acting insulin medicament in the twelve hours prior to the first basal insulin related event and (ii) the subject has taken a meal bolus of the short acting insulin medicament with each hypoglycaemic event free meal in the fourteen hours prior to the first fasting event, wherein the occurrence of a correction bolus, a first basal insulin related event, a hypoglycaemic event free meal are identified in the first data set In a further aspect, the occurrence of a correction bolus is further identified in the second data set.

In a further aspect, the estimating the bolus insulin sensitivity change in B.2) is computed as:

$$\left(\frac{ISF_{bolus,i,t}}{ISF_{bolus,i-p,t}}\right) = \left(\frac{BG_{expected} - \widehat{BG}_{bolus,corr,i}}{\widehat{BG}_{bolus,corr,i}} + 1\right),$$

wherein BG$_{expected}$ is the expected blood glucose level (BG$_{expected}$) based on (i) the glucose level ($\widehat{BG}_{bolus,hyp,i}$) of the subject after a meal event, wherein $\widehat{BG}_{bolus,hyp,i}$ is obtained from the portion of the glucose measurements obtained from the first data set that are contemporaneous with a period of time during a hyperglycaemic event after a meal event, and whereby the portion of the glucose measurements is a subset of the measurements that are contemporaneous with the occurrence of the correction bolus with a short acting medicament, (ii) the bolus insulin sensitivity estimate (ISF$_{bolus,i-p,t}$) of the subject related to the occurrence of the prior correction bolus with the short acting insulin medicament and (iii) an insulin medicament injection event from the second data set corresponding to the occurrence of the correction bolus, and wherein $\widehat{BG}_{bolus,corr,i}$ is the glucose level ($\widehat{BG}_{bolus,corr,i}$) of the subject after the occurrence of the correction bolus, wherein $\widehat{BG}_{bolus,corr,i}$ is obtained from the portion of the glucose measurements of the first data set that are contemporaneous with a period of time after the occurrence of the correction bolus, and whereby the portion of the glucose measurements is a subset of the measurements that are contemporaneous with the occurrence of the correction bolus with a short acting medicament.

In a further aspect, the estimating the bolus insulin sensitivity change in B.2) is computed as:

$$\left(\frac{ISF_{bolus,i,t}}{ISF_{bolus,i-p,t}}\right) = \left(\frac{\widehat{BG}_{bolus,hyp,i} - \widehat{BG}_{bolus,corr,i}}{\widehat{BG}_{bolus,corr,i} - BG_{expected}}\right),$$

wherein $\widehat{BG}_{bolus,hyp,i}$ is the glucose level ($\widehat{BG}_{bolus,hyp,i}$) of the subject after a meal event, wherein $\widehat{BG}_{bolus,hyp,i}$ is obtained from the portion of the glucose measurements obtained from the first data set that are contemporaneous with a period of time during a hyperglycaemic event after a meal event, and whereby the portion of the glucose measurements is a subset of the measurements that are contemporaneous with the occurrence of the correction bolus with a short acting medicament, wherein $\widehat{BG}_{bolus,corr,i}$ is the glucose level ($\widehat{BG}_{corr,i}$) of the subject after occurrence of the correction bolus, wherein $\widehat{BG}_{bolus,corr,i}$ is the glucose level ($\widehat{BG}_{bolus,corr,i}$) of the subject after the occurrence of the correction bolus, wherein $\widehat{BG}_{bolus,corr,i}$ is obtained from the portion of the glucose measurements of the first data set that are contemporaneous with a period of time after the occurrence of the correction bolus, and whereby the portion of the glucose measurements is a subset of the measurements that are contemporaneous with the occurrence of the correction bolus with a short acting medicament, and wherein BG$_{expected}$ is the expected blood glucose level (BG$_{expected}$) based on (i) the glucose level ($\widehat{BG}_{bolus,hyp,i}$) of the subject after a meal event, wherein $\widehat{BG}_{bolus,hyp,i}$ is obtained from the portion of the glucose measurements obtained from the first data set that are contemporaneous with a period of time during a hyperglycaemic event after a meal event, and whereby the portion of the glucose measurements is a subset of the measurements that are contemporaneous with the occurrence of the correction bolus with a short acting medicament, (ii) the bolus insulin sensitivity estimate (ISF$_{bolus,i-p,t}$) of the subject related to the occurrence of the prior correction bolus with the short acting insulin medicament and (iii) an insulin medicament injection event from the second data set corresponding to the occurrence of the correction bolus.

In a further aspect, the expected blood glucose level (BG$_{expected}$) is computed as:

$$BG_{expected} = \widehat{BG}_{bolus1,hyp,i} - ISF_{bolus,i-p,t}U_{bolus,i}.$$

In a further aspect, the estimating the bolus insulin sensitivity curve (ISF$_{bolus,i}$) as a function of the estimated basal insulin sensitivity change, in response to estimating the basal insulin sensitivity change in B.1) comprises computing:

$$ISF_{bolus,i} = \left(\frac{ISF_{basal,i,t} - ISF_{basal,i-p,t}}{ISF_{basal,i-p,t}} + 1\right) ISF_{bolus,i-p},$$

wherein $ISF_{bolus,i-p}$ represents a prior bolus sensitivity factor curve estimate.

In a further aspect, the estimating the basal insulin sensitivity curve ($ISF_{basal,i}$) as a function of the estimated bolus insulin sensitivity change, in response to estimating the bolus insulin sensitivity change in B2) comprises computing:

$$ISF_{basal,i} = \left(\frac{ISF_{bolus,i,t} - ISF_{bolus,i-p,t}}{ISF_{bolus,i-p,t}} + 1\right) ISF_{basal,i-p},$$

wherein $ISF_{basal,i-p}$ represents a prior basal sensitivity factor curve estimate.

In a further aspect, the updating the bolus insulin sensitivity factor curve comprises computing:

$$ISF_{bolus} = \sum_{n=i-q}^{i} w_n ISF_{bolus,n},$$

wherein,
q is a predetermined number of historical updates to the bolus insulin sensitivity curve ($ISF_{bolus}$),
w is a linear or nonlinear vector of normalised weights,
n is an integer index into the historical updates to the bolus insulin sensitivity curve ($ISF_{bolus}$) and vector w, and
$ISF_{bolus,n}$ is an $n^{th}$ past bolus insulin sensitivity curve ($ISF_{bolus}$) curve.

In a further aspect, the updating the basal insulin sensitivity factor curve comprises computing:

$$ISF_{basal} = \sum_{n=i-q}^{i} w_n ISF_{basal,n}$$

wherein,
q is a predetermined number of historical updates to the basal insulin sensitivity curve ($ISF_{basal}$),
w is a linear or nonlinear vector of normalised weights,
n is an integer index into the historical updates to the basal insulin sensitivity curve ($ISF_{basal}$) and vector w, and
$ISF_{basal,n}$ is an $n^{th}$ past basal insulin sensitivity curve ($ISF_{basal}$).

In a further aspect, the method further comprises:
obtaining a third data set (238), the third data set comprising a plurality of physiological measurements of the subject taken over the first period of time and, for each respective physiological measurement (240) in the plurality of physiological measurements, a physiological measurement timestamp (242) representing when the respective physiological measurement was made; and wherein
a value of p is determined by the plurality of physiological measurements.

In a further aspect, each physiological measurement is a measurement of body temperature of the subject and wherein p is reduced during periods when the subject has an elevated temperature.

In a further aspect, each physiological measurement is a measurement of activity of the subject and wherein p is reduced during periods when the subject is incurring elevated activity.

In a further aspect is provided a method for estimating parameters in an insulin medicament dosage regimen for a subject that includes both a short acting insulin medicament regimen and a long acting insulin medicament regimen, the method comprising:

A) obtaining:
  A.1) a first data set, the first data set comprising a plurality of glucose measurements of the subject taken over a first period of time and, for each respective glucose measurement in the plurality of glucose measurements, a timestamp representing when the respective measurement was made;
  A.2) a second data set from one or more insulin pens used by the subject to apply the insulin medicament dosage regimen, the second data set comprises a plurality of insulin medicament records, each insulin medicament record in the plurality of medicament records comprises: (i) a respective insulin medicament injection event including an amount of insulin medicament injected into the subject using a respective insulin pen in the one or more insulin pens (ii) a corresponding electronic timestamp that is automatically generated by the respective insulin pen upon occurrence of the respective insulin medicament injection event, and (iii) a type of insulin medicament, wherein the type of insulin medicament is a short acting insulin medicament or a long acting insulin medicament;

B) determining one or more insulin sensitivity change estimates by:
  B.1) making an estimate of a basal insulin sensitivity change between a basal insulin sensitivity estimate ($ISF_{basal,i,t}$) for the subject related to the occurrence of a first basal insulin related event undertaken by the subject within the first period of time, when the first basal insulin related event is deemed qualified, and a basal insulin sensitivity estimate ($ISF_{basal,i-p,t}$) of the subject related to the occurrence of a qualified basal insulin related event occurring before the first basal insulin related event, wherein the occurrence of the basal insulin related events are identified in the first data set, the estimating using:
    (i) the basal insulin sensitivity estimate ($ISF_{basal,i-p,t}$) of the subject related to the occurrence of the qualified basal insulin related event occurring before the first basal insulin related event (ii) glucose measurements from the first data set contemporaneous with the occurrence of the first qualified basal insulin related event, (iii) glucose measurements from the first data set contemporaneous with the occurrence of the qualified basal insulin related event occurring before the first qualified basal insulin related event, (iv) an insulin medicament injection event from the second data set corresponding to the first qualified basal insulin related event, wherein the injection has been applied according to the long acting insulin medicament regimen, and (v) an insulin medicament injection event from the second data set corresponding to the qualified basal insulin related event occurring before the first qualified basal insulin related event, wherein the injection has been applied according to the long acting insulin medicament regimen; and/or B.2) making an estimate of a bolus insulin sensitivity change between a bolus insulin sensitivity estimate ($ISF_{bolus,i,t}$) for the subject relating to the occurrence of a correction bolus with a short acting insulin medicament within the first period of time and a bolus insulin sensitivity estimate ($ISF_{bolus,i-p,t}$) of the subject related to the occurrence of a prior correction bolus with the short acting insulin medicament, wherein the occurrence of the correction bolus and the occurrence of the prior correction bolus are identified in the first data set, the estimating using: (i) glucose measurements from the first data set contemporaneous with the occurrence of the correction bolus with a short acting medicament, (ii) the bolus insulin sensitivity estimate ($ISF_{bolus,i-p,t}$) of the subject related to the occurrence of a prior correction bolus with the short acting insulin medicament and (iii) an insulin medicament injection event from the second data set corresponding to the occurrence of the correction bolus and applied according to the short acting insulin medicament regimen; and C) estimating the bolus insulin sensitivity estimate ($ISF_{bolus,i,t}$) as a function of the estimated basal insulin sensitivity change, in response to making an estimate of the basal insulin sensitivity change in B.1); and/or D) estimating the basal insulin sensitivity estimate ($ISF_{basal,i,t}$) as a function of the estimated bolus insulin sensitivity change, in response to making an estimate of the bolus insulin sensitivity change in B.2), and wherein the insulin sensitivity estimates are parameters in the insulin medicament regimen.

In a further aspect is provided, a computer program is provided comprising instructions that, when executed by one or more processors, perform the method according to claim 23.

In a further aspect is provided, a computer-readable data carrier having stored thereon the computer program according to claim 24.

In some embodiments, the ISF is a weighted average over a past estimate horizon, either past few days or a specific past period known to be similar with respect to current physiological circumstances. In some embodiments, the ISF is updated as soon as new data is available but suspended during non-adherence. An example of non-adherence events include, for instance, following a forgotten dinner bolus, in which glucose levels will be higher than otherwise and therefore the data is not useful for accurate ISF estimation. If a significant change in ISF is detected, the system can either ask for user input of an explanation or use data from wearables such as temperature, blood pressure or activity meters. If the significant change is confirmed by such a device, the estimation horizon is shortened or moved to a known past similar period. Assuming that ISF and CIR are proportionally correlated, CIR is updated proportionally according to changes in ISF, i.e. if increase in insulin sensitivity is observed, then less insulin is typically needed to account for CHO in a meal. By only estimating ISF based on correction bolus and not meal-related doses, the uncertainty of CHO counting and postprandial BG behavior is eliminated. Furthermore, by estimating ISF based on response in fasting glucose following a basal injection, more frequent ISF estimations are available than if only done based on bolus. Furthermore, measuring changes in ISF based on response to two different insulins adds robustness to ISF estimation.

Adding wearable devices such as activity monitors and temperature measuring devices allows additional features. For instance, a temperature measuring device (i) offers the prospect of knowing when changes in ISF are expected due to illness, allows for insulin medicament titration to be set on hold during illness, alerts for times in which detected changes in ISF should be given higher weight. An activity monitor offers knowing when changes in ISF are expected due to increased activity, and alerts as to when detected changes in ISF can be given higher weight.

Thus, major advantages of the disclosed systems and methods are therefore a more robust estimate of insulin sensitivity which results in a more precise insulin dosage during long-term physiological changes as well as periods of deviations such as illness, stress and increased level of activity.

As an application of these techniques, a diabetic patient or a health care practitioner is provided with an accurate basal insulin sensitivity factor curve and/or bolus insulin sensitivity factor curve that serves as an improved basis for providing a recommended dose of a short acting insulin medicament to achieve a target fasting glucose level for the diabetic patient.

In one aspect of the present disclosure, systems and methods are provided for estimating parameters in an insulin medicament regimen for a subject that includes both a short acting insulin medicament regimen and a long acting insulin medicament regimen. A first data set is obtained. The first data set comprises a plurality of glucose measurements of the subject taken over a period of time and, for each respective glucose measurement in the plurality of glucose measurements, a timestamp representing when the respective measurement was made.

A new basal insulin sensitivity estimate ($ISF_{basal,i,t}$) or a new bolus insulin sensitivity estimate ($ISF_{bolus,i,t}$) is then made for the subject.

The basal insulin sensitivity estimate ($ISF_{basal,i,t}$) is made for the subject upon occurrence of a first fasting event undertaken by the subject within a period of time encompassed by the first data set, when the first fasting event is deemed qualified. In some embodiments, the first fasting event is deemed qualified when (i) the subject has taken no correction bolus of the short acting insulin medicament in the twelve hours prior to the first fasting event and (ii) the subject has taken a meal bolus of the short acting insulin medicament with each hypoglycaemic event free meal in the fourteen hours prior to the first fasting event, e.g, a meal bolus was taken with each meal except if the bolus was not taken due to a hypoglyceamic event. The basal insulin sensitivity estimate ($ISF_{basal,i,t}$) makes use of (i) an expected fasting blood glucose level based upon a present dosing of a long acting insulin medicament in the long acting insulin medicament regimen ($FBG_{expected}$) during the first fasting event, (ii) a fasting glucose level of the subject during the first fasting event ($\widehat{FBG}_i$) that is obtained from the portion of the plurality of glucose measurements that is contemporaneous with the first fasting event, and (iii) an insulin sensitivity factor of the subject during a qualified fasting event occurring before the first fasting event ($ISF_{basal,i-p,t}$). In some embodiments, the basal insulin sensitivity estimate ($ISF_{basal,i,t}$) for the subject is computed as:

$$ISF_{basal,i,t} = \left(\frac{FBG_{expected} - \widehat{FBG}_i}{\widehat{FBG}_i} + 1\right) ISF_{basal,i-p,t}.$$

A basal insulin sensitivity factor curve ($ISF_{basal,i}$) is estimated when the new basal insulin sensitivity estimate ($ISF_{basal,i,t}$) is made. Whereas the new basal insulin sensitivity factor estimate ($ISF_{basal,i,t}$) represents basal insulin sensitivity of the subject at the time of the occurrence of the first qualified fasting event, the basal insulin sensitivity factor curve estimate ($ISF_{basal,i}$) represents the basal insulin sensitivity factor of the subject over a predetermined recurring time period, such as the course of a day. However, the new basal insulin sensitivity estimate ($ISF_{basal,i,t}$) is used to update the basal insulin sensitivity factor curve estimate ($ISF_{basal,i}$) in accordance with the teachings of the present disclosure. In some embodiments, the basal sensitivity factor curve estimate ($ISF_{basal,i}$) is computed by the formula:

$$ISF_{basal,i} = \left( \frac{ISF_{basal,i,t} - ISF_{basal,i-p,t}}{ISF_{basal,i-p,t}} + 1 \right) ISF_{basal,i-p},$$

where $ISF_{basal,i-p}$ represents a prior basal sensitivity factor curve estimate and, here, t serves to index through the entire basal sensitivity factor curve.

The bolus insulin sensitivity estimate ($ISF_{bolus,i,t}$) is made for the subject upon occurrence of a correction bolus with a short acting insulin medicament within the period of time. This estimate makes use of (i) an expected blood glucose level based upon the correction bolus with the short acting insulin medicament ($BG_{expected}$), (ii) the glucose level of the subject after occurrence of the correction bolus ($\widetilde{BG}_{corr,i}$), where $\widetilde{BG}_{corr,i}$ is obtained from the portion of the plurality of glucose measurements that is contemporaneous with a period of time after the occurrence of the correction bolus, and (iii) an insulin sensitivity factor of the subject estimated based upon occurrence of a prior correction bolus with the short acting insulin medicament ($ISF_{bolus,i-p,t}$). In some embodiments, this bolus insulin sensitivity estimate ($ISF_{bolus,i,t}$) is computed as:

$$ISF_{bolus,i,t} = \left( \frac{BG_{expected} - \widetilde{BG}_{corr,i}}{\widetilde{BG}_{corr,i}} + 1 \right) ISF_{bolus,i-p}.$$

A bolus insulin sensitivity factor curve ($ISF_{bolus,i}$) is made when the new bolus insulin sensitivity estimate ($ISF_{bolus,i,t}$) is made. Whereas the new bolus insulin sensitivity estimate ($ISF_{bolus,i,t}$) represents bolus insulin sensitivity of the subject at the time of the correction bolus, the bolus insulin sensitivity factor curve ($ISF_{bolus,i}$) represents the bolus insulin sensitivity factor of the subject over a predetermined recurring time period, such as the course of a day. However, the new bolus insulin sensitivity estimate ($ISF_{bolus,i,t}$) is used to update the bolus insulin sensitivity factor curve ($ISF_{bolus,i}$) in accordance with the teachings of the present disclosure. In some embodiments, the estimating the bolus sensitivity factor curve comprises computing:

$$ISF_{bolus,i} = \left( \frac{ISF_{basal,i,t} - ISF_{basal,i-p,t}}{ISF_{basal,i-p,t}} + 1 \right) ISF_{bolus,i-p},$$

where $ISF_{bolus,i-p}$ represents a prior bolus sensitivity factor curve estimate.

In some embodiments, further estimates are made. For instance, in some embodiments the bolus insulin sensitivity curve ($ISF_{bolus,i}$) is estimated as a function of the newly estimated basal insulin sensitivity factor curve ($ISF_{basal,i}$). That is, when the estimated basal insulin sensitivity factor curve ($ISF_{basal,i}$) is estimated as described above, the newly estimated basal insulin sensitivity factor curve ($ISF_{basal,i}$) is used to estimate the bolus insulin sensitivity curve ($ISF_{bolus,i}$). In some embodiments, the estimating of the bolus insulin sensitivity curve ($ISF_{bolus,i}$) as a function of the estimated basal insulin sensitivity factor curve ($ISF_{basal,i}$) comprises computing:

$$ISF_{bolus,i} = \left( \frac{ISF_{basal,i,t} - ISF_{basal,i-p,t}}{ISF_{basal,i-p,t}} + 1 \right) ISF_{bolus,i-p},$$

where $ISF_{bolus,i-p}$ represents a prior bolus sensitivity factor curve estimate.

Correspondingly, in some embodiments, the basal insulin sensitivity curve ($ISF_{basal,i}$) is estimated as a function of the newly estimated bolus insulin sensitivity factor curve ($ISF_{bolus,i}$). That is, when the estimated bolus insulin sensitivity factor curve ($ISF_{bolus,i}$) is estimated as described above, the newly estimated bolus insulin sensitivity factor curve ($ISF_{bolus,i}$) is used to estimate the basal insulin sensitivity curve ($ISF_{basal,i}$) In some embodiments, the estimating the basal insulin sensitivity curve ($ISF_{basal,i}$) as a function of the estimated bolus insulin sensitivity factor curve ($ISF_{bolus,i}$) comprises computing:

$$ISF_{basal,i} = \left( \frac{ISF_{bolus,i,t} - ISF_{bolus,i-p,t}}{ISF_{bolus,i-p,t}} + 1 \right) ISF_{basal,i-p},$$

where $ISF_{basal,i-p}$ represents a prior basal sensitivity factor curve estimate.

The above embodiments describe the computation of a new estimated bolus insulin sensitivity curve ($ISF_{bolus,i}$) and/or a new basal insulin sensitivity curve ($ISF_{basal,i}$) for an $i^{th}$ time period, such as an $i^{th}$ day. Typically this $i^{th}$ time period (e.g., this $i^{th}$ day) is the present day. In some embodiments, when a new estimated bolus insulin sensitivity curve ($ISF_{bolus,i}$) has been estimated, it is then combined with one or more bolus insulin sensitivity curve estimates from prior days (or prior recurring time periods) in order to form an updated bolus insulin sensitivity curve ($ISF_{bolus}$). In some embodiments, this bolus insulin sensitivity factor curve updated by computing:

$$ISF_{bolus} = \sum_{n=i-q}^{i} w_n ISF_{bolus,n},$$

where q is a predetermined number of historical updates to the bolus insulin sensitivity curve ($ISF_{bolus}$), w is a linear or nonlinear vector of normalised weights, n is an integer index into the historical updates to $ISF_{bolus}$ and vector w, and $ISF_{bolus,n}$ is an $n^{th}$ past bolus insulin sensitivity curve ($ISF_{bolus}$).

Likewise, in some embodiments, when a new estimated basal insulin sensitivity factor curve ($ISF_{basal,i}$) has been made, it is then combined with one or more basal insulin sensitivity curves from prior days (or prior recurring time periods) in order to form an updated basal insulin sensitivity factor curve ($ISF_{basal}$) In some embodiments, the updating the basal insulin sensitivity factor curve comprises computing:

$$ISF_{basal} = \sum_{n=i-q}^{i} w_n ISF_{basal,n},$$

where q is a predetermined number of historical updates to the basal insulin sensitivity curve ($ISF_{basal}$), w is a linear or nonlinear vector of normalised weights, n is an integer index into the historical updates to the basal insulin sensitivity curve ($ISF_{basal}$) and vector w, and $ISF_{basal,n}$ is an $n^{th}$ past basal insulin sensitivity curve ($ISF_{basal}$) curve.

In some such embodiments, a recommended dose of the short acting insulin to achieve a target fasting glucose level in the subject is provided by using glucose measurements from a portion of the plurality of glucose measurements and the updated bolus insulin sensitivity curve ($ISF_{bolus}$) or the updated basal insulin sensitivity curve ($ISF_{basal}$).

In some embodiments, the method further comprises obtaining a third data set that comprises a plurality of physiological measurements of the subject taken over the first period of time and, for each respective physiological measurement in the plurality of physiological measurements, a physiological measurement timestamp representing when the respective physiological measurement was made. In such embodiments, the value of p, in other words the amount of historical data that is used to update the basal and/or bolus insulin sensitivity factor curves, is determined by the plurality of physiological measurements. In some embodiments, each physiological measurement is a measurement of body temperature of the subject and the value p is reduced during periods when the subject has an elevated temperature. In some embodiments, each physiological measurement is a measurement of activity of the subject and the value p is reduced during periods when the subject is incurring elevated activity.

In some embodiments, the long acting insulin medicament consists of a single insulin medicament having a duration of action that is between 12 and 24 hours or a mixture of insulin medicaments that collectively have a duration of action that is between 12 and 24 hours, and the short acting insulin medicament consists of a single insulin medicament having a duration of action that is between three to eight hours or a mixture of insulin medicaments that collectively have a duration of action that is between three to eight hours.

In another aspect is provided, a device for estimating parameters in an insulin medicament regimen for a subject that includes both a short acting insulin medicament regimen and a long acting insulin medicament regimen, and wherein the device comprises one or more processors and a memory, the memory storing instructions that, when executed by the one or more processors, perform a method of:

A) obtaining a first data set, the first data set comprising a plurality of glucose measurements of the subject taken over a first period of time and, for each respective glucose measurement in the plurality of glucose measurements, a timestamp representing when the respective measurement was made;

B) determining an estimate by:

B.1) making a basal insulin sensitivity estimate ($ISF_{basal,i,t}$) for the subject upon occurrence of a first fasting event undertaken by the subject within the first period of time, when the first fasting event is deemed qualified, the estimating using (i) an expected fasting blood glucose level based upon a present dosing of a long acting insulin medicament in the long acting insulin medicament regimen ($FBG_{expected}$) during the first fasting event, (ii) a fasting glucose level of the subject during the first fasting event ($\overline{FBG}_i$) that is obtained from the portion of the plurality of glucose measurements that is contemporaneous with the first fasting event, and (iii) an insulin sensitivity factor of the subject during a qualified fasting event occurring before the first fasting event ($ISF_{basal,i-p,t}$); or B.2) making a bolus insulin sensitivity estimate ($ISF_{bolus,i,t}$) for the subject upon occurrence of a correction bolus with a short acting insulin medicament within the first period of time, the estimating using (i) an expected blood glucose level based upon the correction bolus with the short acting insulin medicament ($BG_{expected}$), (ii) the glucose level of the subject after occurrence of the correction bolus ($\overline{BG}_{corr,i}$), wherein $\overline{BG}_{corr,i}$ is obtained from the portion of the plurality of glucose measurements that is contemporaneous with a period of time after the occurrence of the correction bolus, and (iii) an insulin sensitivity factor of the subject estimated based upon occurrence of a prior correction bolus with the short acting insulin medicament ($ISF_{bolus,i-p,t}$);

C) estimating a basal insulin sensitivity factor curve ($ISF_{basal,i}$) when the bolus insulin sensitivity estimate ($ISF_{basal,i,t}$) is made in B.1); and D) estimating a bolus insulin sensitivity factor curve ($ISF_{bolus,i}$) when the bolus insulin sensitivity estimate ($ISF_{bolus,i,t}$) is made in B.2).

BRIEF DESCRIPTION OF THE DRAWINGS

FIGS. 4A, 4B, and 4C collectively provide a flow chart of processes and features of a device for estimating parameters in an insulin medicament regimen for a subject in accordance with various embodiments of the present disclosure.

FIG. 9A illustrates determining a basal insulin sensitivity estimate ($ISF_{basal,i,t}$) upon occurrence of a qualified fasting event at a given time (t) and how a value of this basal insulin sensitivity estimate ($ISF_{basal,i,t}$) compares to respective existing basal and bolus insulin sensitivity factor curves $ISF_{basal}$ and $ISF_{bolus}$ over the course of a time period in accordance with an embodiment of the present disclosure.

Like reference numerals refer to corresponding parts throughout the several views of the drawings.

DETAILED DESCRIPTION

Figure 1:
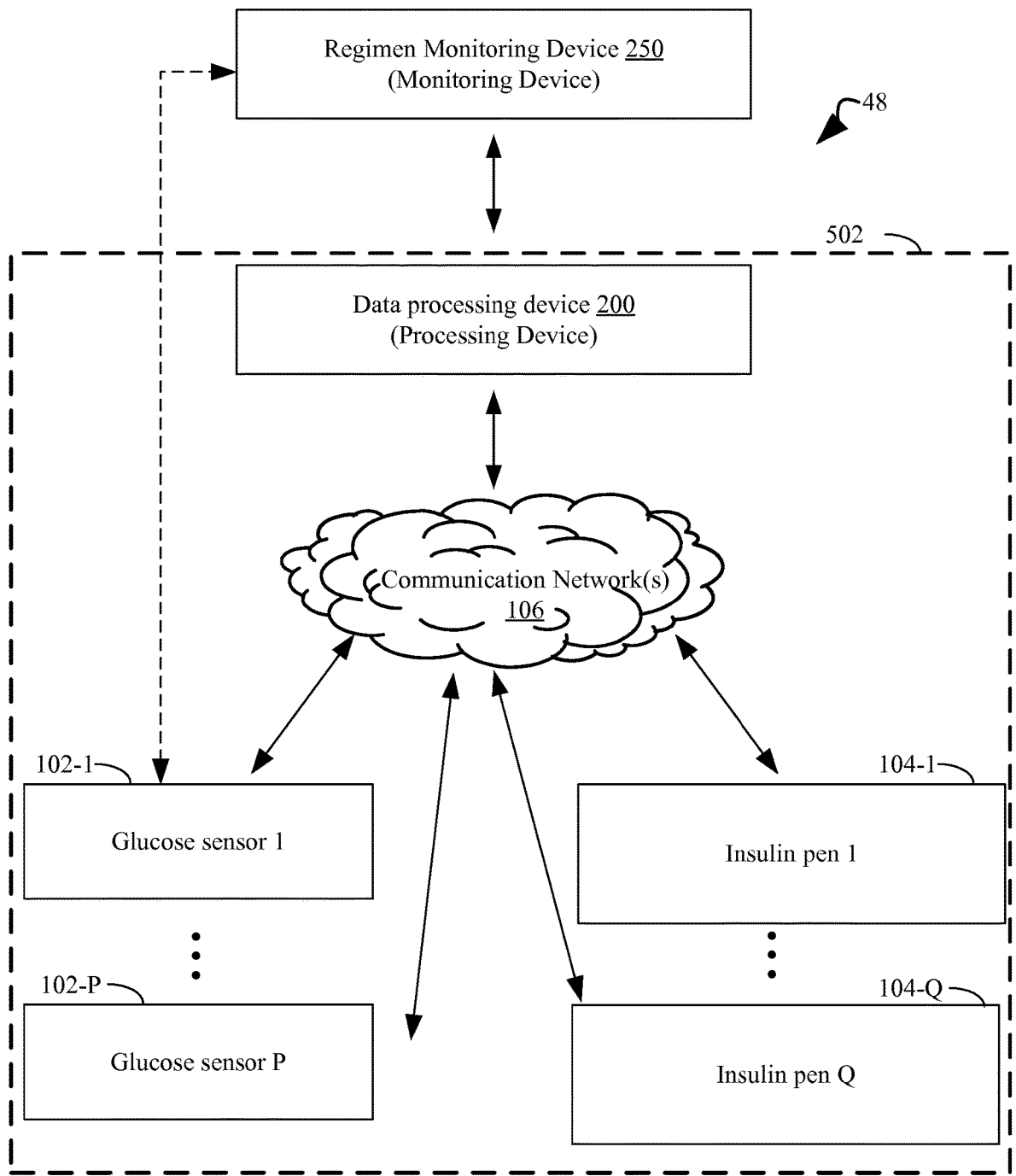
FIG. 1 illustrates an exemplary system topology that includes a regimen monitoring device for estimating parameters in an insulin medicament regimen, a regimen adherence assessor device for analyzing and preparing regimen adherence data, one or more glucose sensors that measure glucose data from the subject, and one or more insulin pens that are used by the subject to inject insulin medicaments in accordance with the prescribed insulin medicament regimen, where the above-identified components are interconnected, optionally through a communications network, in accordance with an embodiment of the present disclosure.
Figure 5:
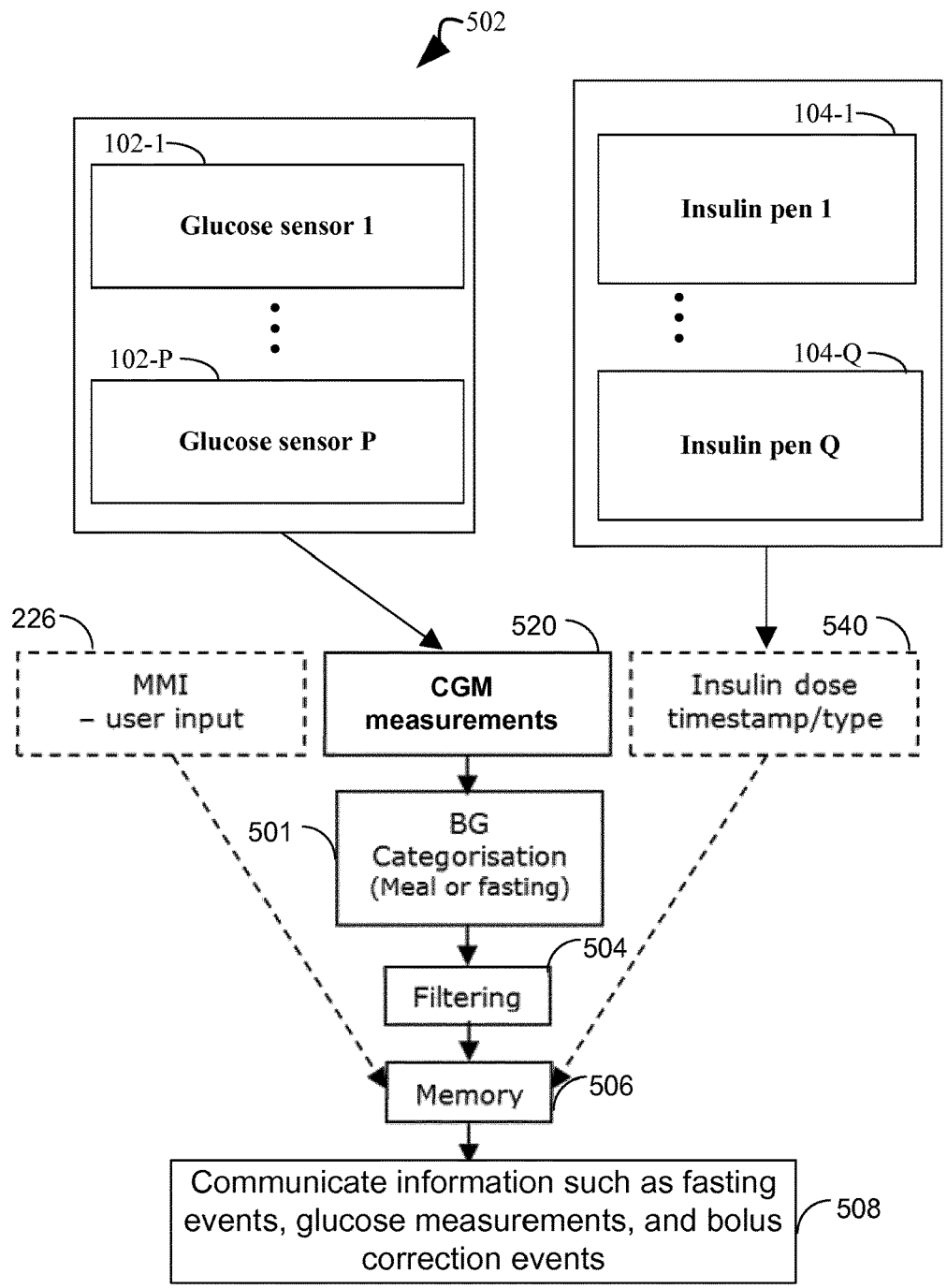
FIG. 5 illustrates an example integrated system of connected insulin pen(s), continuous glucose monitor(s), memory and a processor for performing algorithmic categorization of autonomous glucose data in accordance with an embodiment of the present disclosure.

The present disclosure relies upon the acquisition of data regarding a plurality of metabolic events, such as fasting events or meals, a subject engaged in over a period of time. For each such metabolic event, the data includes a timestamp. FIG. 1 illustrates an example of a system 48 for estimating parameters in an insulin medicament regimen for a subject and an integrated system 502 for the acquisition of such data, and FIG. 5 provides more details of such a system 502. The integrated system 502 includes one or more connected insulin pens 104, one or more continuous glucose monitors 102, and a memory 506.

With the integrated system 502, autonomous timestamped glucose measurements of the subject are obtained 520. Also, data from the one or more insulin pens used to apply a prescribed insulin regimen to the subject is obtained 540 as a plurality of records. Each record comprises a timestamped event specifying an amount of injected insulin medicament that the subject received as part of the prescribed insulin medicament dosage regimen. In some embodiments, fasting events are identified using the autonomous timestamped glucose measurements of the subject. Optionally, meal events are also identified using the autonomous timestamped glucose measurements 520 In this way, the glucose measurements are categorized 501 and filtered 504 and stored in non-transitory memory 506. This filtered glucose data is communicated in accordance with the methods of the present disclosure 508. For instance, in the form of fasting events, time stamped glucose measurements, and bolus correction events autonomously identified due to their temporal proximity to autonomously determined meal events.

Reference will now be made in detail to embodiments, examples of which are illustrated in the accompanying drawings. In the following detailed description, numerous specific details are set forth in order to provide a thorough understanding of the present disclosure. However, it will be apparent to one of ordinary skill in the art that the present disclosure may be practiced without these specific details. In other instances, well-known methods, procedures, components, circuits, and networks have not been described in detail so as not to unnecessarily obscure aspects of the embodiments.

It will also be understood that, although the terms first, second, etc. may be used herein to describe various elements, these elements should not be limited by these terms. These terms are only used to distinguish one element from another. For example, a first subject could be termed a second subject, and, similarly, a second subject could be termed a first subject, without departing from the scope of the present disclosure. The first subject and the second subject are both subjects, but they are not the same subject. Furthermore, the terms "subject" and "user" are used interchangeably herein. By the term insulin pen is meant an injection device suitable for applying discrete doses of insulin, and wherein the injection device is adapted for logging and communicating dose related data.

The terminology used in the present disclosure is for the purpose of describing particular embodiments only and is not intended to be limiting of the invention. As used in the description of the invention and the appended claims, the singular forms "a", "an" and "the" are intended to include the plural forms as well, unless the context clearly indicates otherwise. It will also be understood that the term "and/or" as used herein refers to and encompasses any and all possible combinations of one or more of the associated listed items. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof.

As used herein, the term "if" may be construed to mean "when" or "upon" or "in response to determining" or "in response to detecting," depending on the context. Similarly, the phrase "if it is determined" or "if [a stated condition or event] is detected" may be construed to mean "upon determining" or "in response to determining" or "upon detecting [the stated condition or event]" or "in response to detecting [the stated condition or event]," depending on the context.

Figure 2:
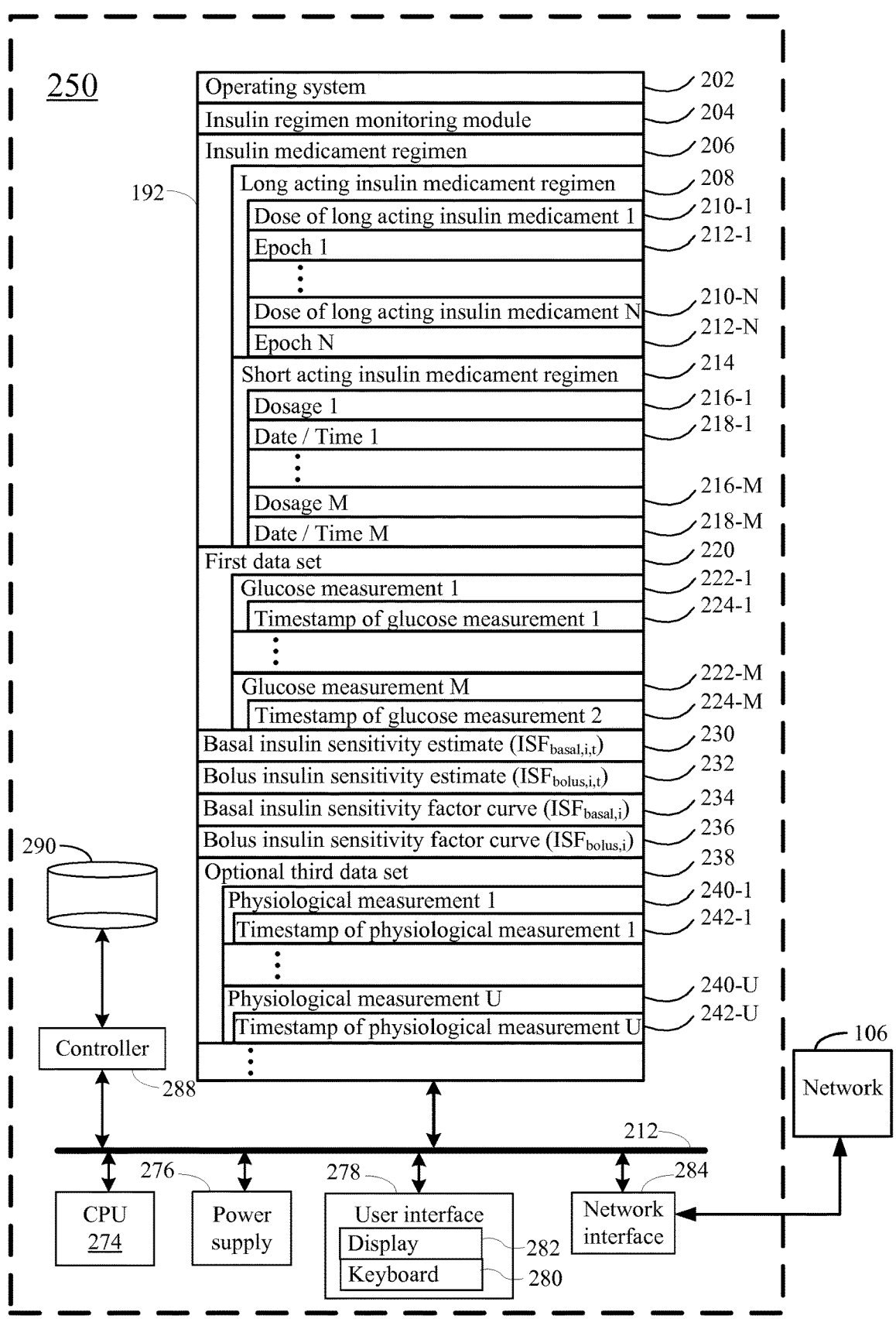
FIG. 2 illustrates a device for estimating parameters in an insulin medicament regimen for a subject in accordance with an embodiment of the present disclosure.
Figure 3:
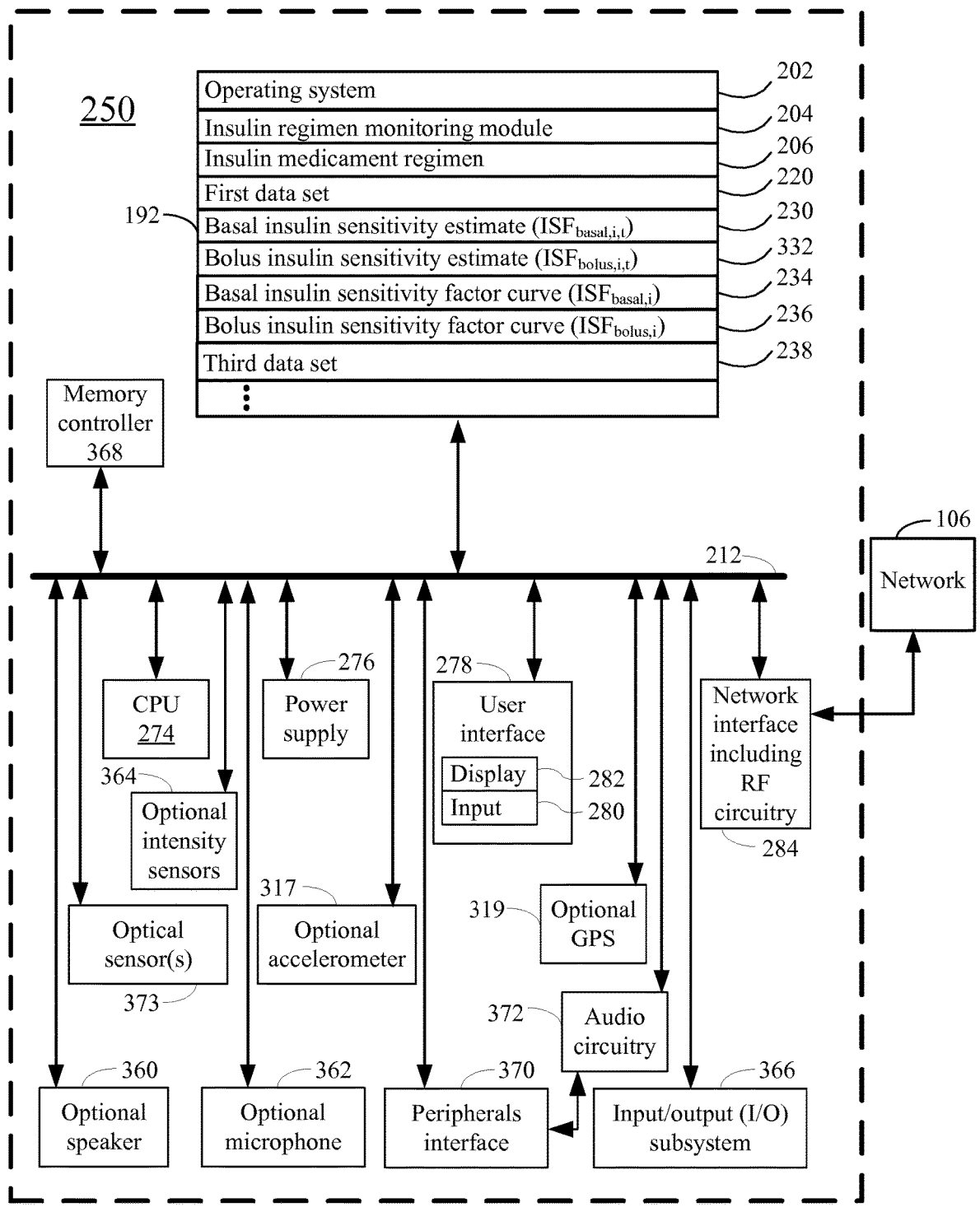
FIG. 3 illustrates a device for estimating parameters in an insulin medicament regimen for a subject in accordance with another embodiment of the present disclosure.

A detailed description of a system 48 for estimating parameters in an insulin medicament regimen for a subject that includes both a short acting insulin medicament regimen and a long acting insulin medicament regimen in accordance with the present disclosure is described in conjunction with FIGS. 1 through 3. As such, FIGS. 1 through 3 collectively illustrate the topology of the system in accordance with the present disclosure. In the topology, there is an insulin medicament dosage regimen monitoring device ("monitoring device 250") (FIGS. 1, 2, and 3), a data processing device ("processing device 200"), one or more glucose sensors 102 associated with the subject (FIG. 1), and one or more insulin pens 104 for injecting insulin medicaments into the subject (FIG. 1). Throughout the present disclosure, the processing device 200 and the monitoring device 250 will be referenced as separate devices solely for purposes of clarity. That is, the disclosed functionality of the processing device 200 and the disclosed functionality of the monitoring device 250 are contained in separate devices as illustrated in FIG. 1. However, it will be appreciated that, in fact, in some embodiments, the disclosed functionality of the processing device 200 and the disclosed functionality of the monitoring device 250 are contained in a single device. In some embodiments, the disclosed functionality of the processing device 200 and/or the disclosed functionality of the monitoring device 250 are contained in a single device and this single device is a glucose monitor 102 or the insulin pen 104.

Referring to FIG. 1, the monitoring device 250 estimates parameters in an insulin medicament regimen for a subject that includes both a short acting insulin medicament regimen and a long acting insulin medicament regimen. To do this, the processing device 200, which is in electrical communication with the monitor device 250, receives autonomous glucose measurements originating from one or more glucose sensors 102 attached to a subject on an ongoing basis. Further, the processing device 200 receives insulin medicament injection data from one or more insulin pens 104 used by the subject to obtain insulin medicaments. In some embodiments, the processing device 200 receives such data directly from the glucose sensor(s) 102 and insulin pens 104 used by the subject. For instance, in some embodiments the processing device 200 receives this data wirelessly through radio-frequency signals. In some embodiments such signals are in accordance with an 802.11 (WiFi), Bluetooth, or ZigBee standard. In some embodiments, the monitoring device 200 receives such data directly, identifies metabolic events, such as fasting events and meals, within the data, and passes such data to the monitoring device 250. In some embodiments the glucose sensor 102 and/or insulin pen includes an RFID tag and communicates to processing device 200 and/or the monitoring device 250 using RFID communication.

In some embodiments, the processing device 200 and/or the monitoring device 250 is not proximate to the subject and/or does not have wireless capabilities or such wireless capabilities are not used for the purpose of acquiring glucose data and insulin medicament injection data. In such embodiments, a communication network 106 may be used to communicate glucose measurements from the one or more glucose sensors 102 to the processing device 200 and from the one or more insulin pens 104 to the processing device 200.

Examples of networks 106 include, but are not limited to, the World Wide Web (WWW), an intranet and/or a wireless network, such as a cellular telephone network, a wireless local area network (LAN) and/or a metropolitan area network (MAN), and other devices by wireless communication. The wireless communication optionally uses any of a plurality of communications standards, protocols and technologies, including but not limited to Global System for Mobile Communications (GSM), Enhanced Data GSM Environment (EDGE), high-speed downlink packet access (HSDPA), high-speed uplink packet access (HSUPA), Evolution, Data-Only (EV-DO), HSPA, HSPA+, Dual-Cell HSPA (DC-HSPDA), long term evolution (LTE), near field communication (NFC), wideband code division multiple access (W-CDMA), code division multiple access (CDMA), time division multiple access (TDMA), Bluetooth, Wireless Fidelity (Wi-Fi) (e.g., IEEE 802.11a, IEEE 802.11ac, IEEE 802.11ax, IEEE 802.11b, IEEE 802.11g and/or IEEE 802.11n), voice over Internet Protocol (VoIP), Wi-MAX, a protocol for e-mail (e.g., Internet message access protocol (IMAP) and/or post office protocol (POP)), instant messaging (e.g., extensible messaging and presence protocol (XMPP), Session Initiation Protocol for Instant Messaging and Presence Leveraging Extensions (SIMPLE), Instant Messaging and Presence Service (IMPS)), and/or Short Message Service (SMS), or any other suitable communication protocol, including communication protocols not yet developed as of the filing date of the present disclosure.

In some embodiments, there is a single glucose sensor 102 attached to the subject and the processing device 200 and/or the monitoring device 250 is part of the glucose sensor 102. That is, in some embodiments, the processing device 200 and/or the monitoring device 250 and the glucose sensor 102 are a single device.

In some embodiments, the adherence device 200 and/or the monitor device 250 is part of an insulin pen or pump 104. That is, in some embodiments, the adherence device 200 and/or the monitor device 250 and an insulin pen 104 are a single device.

Of course, other topologies of the system 48 are possible. For instance, rather than relying on a communications network 106, the one or more glucose sensors 102 and the one or more insulin pens 104 may wirelessly transmit information directly to the processing device 200 and/or the monitoring device 250. Further, in some embodiments, the processing device 200 and/or the monitoring device 250 constitutes a portable electronic device, a server computer, or in fact constitute several computers that are linked together in a network or be a virtual machine in a cloud computing context. As such, the exemplary topology shown in FIG. 1 merely serves to describe the features of an embodiment of the present disclosure in a manner that will be readily understood to one of skill in the art.

Referring to FIG. 2, in typical embodiments, the monitoring device 250 comprises one or more computers. For purposes of illustration in FIG. 2, the monitoring device 250 is represented as a single computer that includes all of the functionality for evaluating historical adherence to a prescribed insulin medicament dosage regimen for a subject. However, the disclosure is not so limited. In some embodiments, the functionality for estimating parameters in an insulin medicament regimen for a subject that includes both a short acting insulin medicament regimen and a long acting insulin medicament regimen is spread across any number of networked computers and/or resides on each of several networked computers and/or is hosted on one or more virtual machines at a remote location accessible across the communications network 106. One of skill in the art will appreciate that any of a wide array of different computer topologies are used for the application and all such topologies are within the scope of the present disclosure.

Turning to FIG. 2 with the foregoing in mind, an exemplary monitoring device 250 for estimating parameters in an insulin medicament regimen for a subject comprises one or more processing units (CPU's) 274, a network or other communications interface 284, a memory 192 (e.g., random access memory), one or more magnetic disk storage and/or persistent devices 290 optionally accessed by one or more controllers 288, one or more communication busses 212 for interconnecting the aforementioned components, and a power supply 276 for powering the aforementioned components. In some embodiments, data in memory 192 is seamlessly shared with non-volatile memory 290 using known computing techniques such as caching. In some embodiments, memory 192 and/or memory 290 includes mass storage that is remotely located with respect to the central processing unit(s) 274. In other words, some data stored in memory 192 and/or memory 290 may in fact be hosted on computers that are external to the monitoring device 250 but that can be electronically accessed by the monitoring device 250 over an Internet, intranet, or other form of network or electronic cable (illustrated as element 106 in FIG. 2) using network interface 284.

The memory 192 of the monitoring device 250 for estimating parameters in an insulin medicament regimen for a subject stores:

an operating system 202 that includes procedures for handling various basic system services;

an insulin regimen monitoring module 204;

an insulin medicament regimen for a subject, the insulin medicament regimen comprising a long acting insulin medicament regimen 208 and a short acting insulin medicament regimen 214;

a first data set 220, the first data set comprising a plurality of glucose measurements for the subject and, for each respective glucose measurement 222 in the plurality of glucose measurements, a timestamp 224 representing when the respective glucose measurement was made;

a second data set (not shown) from one or more insulin pens used by the subject to apply the insulin medicament dosage regimen, the second data set comprises a plurality of insulin medicament records, each insulin medicament record in the plurality of medicament records comprises: (i) a respective insulin medicament injection event including an amount of insulin medicament injected into the subject using a respective insulin pen in the one or more insulin pens (ii) a corresponding electronic timestamp that is automatically generated by the respective insulin pen upon occurrence of the respective insulin medicament injection event, and (iii) a type of insulin medicament, wherein the type of insulin medicament is a short acting insulin medicament or a long acting insulin medicament;

a basal insulin sensitivity estimate ($ISF_{basal,i,t}$) 230 for the subject;

bolus insulin sensitivity estimate ($ISF_{bolus,i,t}$) 232 for the subject;

a basal insulin sensitivity factor curve estimate ($ISF_{basal,i}$) 234 for the subject;

a bolus insulin sensitivity factor curve estimate ($ISF_{bolus,i}$) 236 for the subject; and an optional third data set 220, the third data set comprising a plurality of physiological measurements for the subject and, for each respective physiological measurement 240 in the plurality of physiological measurements, a timestamp 242 representing when the respective physiological measurement was made.

Figure 6:
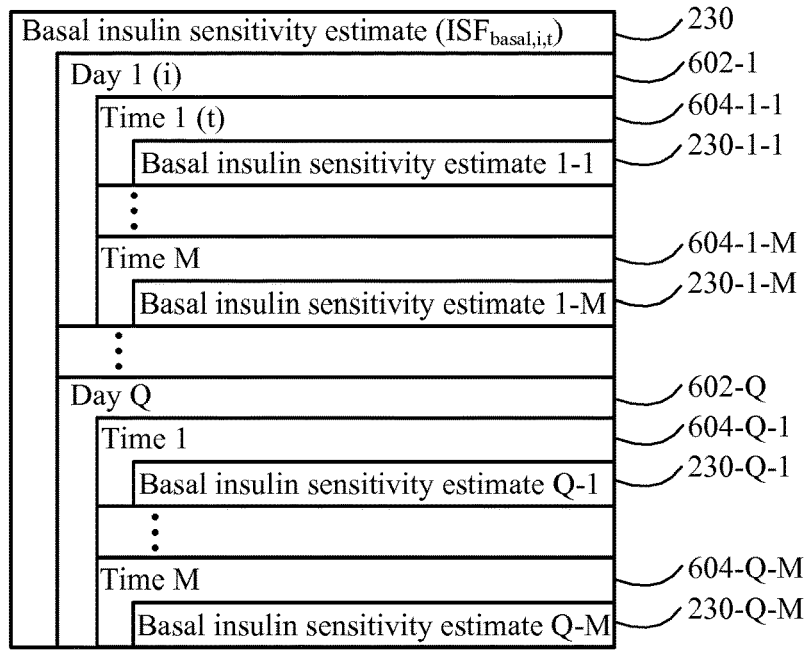
FIG. 6 illustrates basal insulin sensitivity estimate ($ISF_{basal,i,t}$) and bolus insulin sensitivity estimate ($ISF_{bolus,i,t}$) data structures in accordance with an embodiment of the present disclosure.
Figure 6:
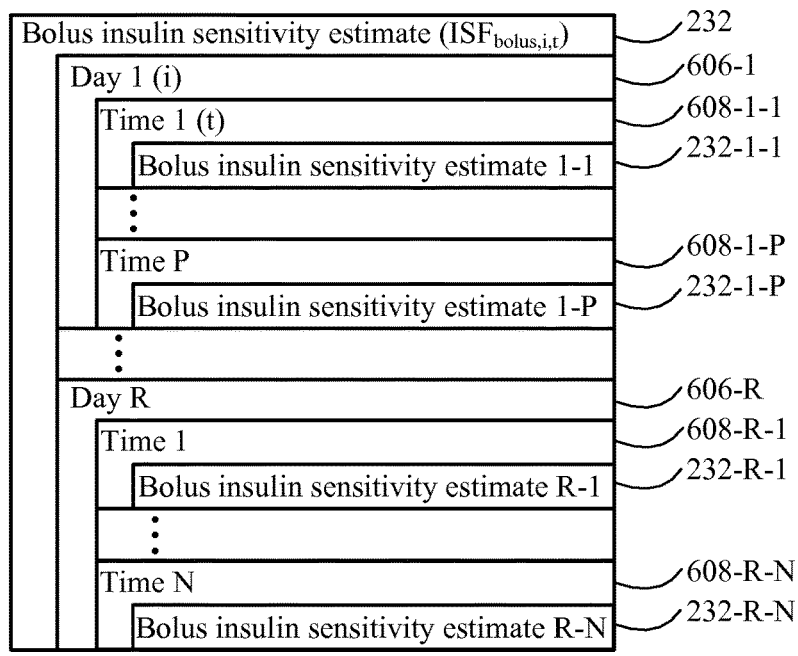

FIG. 6 provides further details on a basal insulin sensitivity estimate ($ISF_{basal,i,t}$) 230 for a subject. Each basal insulin sensitivity estimate ($ISF_{basal,i,t}$) 230 represents a basal insulin sensitivity estimate 230-$x$-$y$, that is taken on a particular day 602-$x$, at a particular time t 604-$x$-$y$, where, here, x represents the particular day, and y represents the particular time t. FIG. 6 also provides further details on a bolus insulin sensitivity estimate ($ISF_{bolus,i,t}$) 232 for a subject. Each bolus insulin sensitivity estimate ($ISF_{bolus,i,t}$) 232 represents a bolus insulin sensitivity estimate 232-$x$-$y$, that is taken on a particular day 606-$x$, at a particular time t 608-$x$-$y$, where, here, x represents the particular day, and y represents the particular time t.

Figure 7:
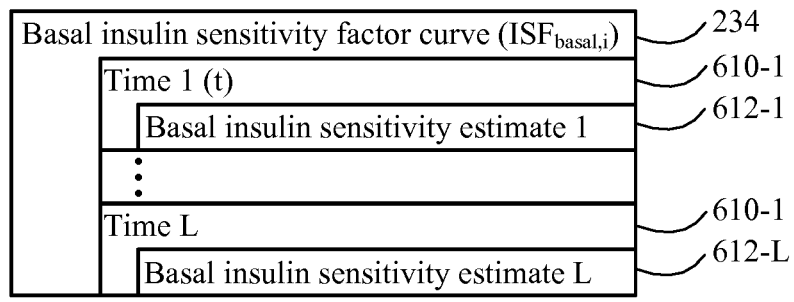
FIG. 7 illustrates a basal insulin sensitivity factor curve ($ISF_{basal,i}$) data structure and a bolus insulin sensitivity factor curve ($ISF_{bolus,i}$) data structure in accordance with an embodiment of the present disclosure.
Figure 7:
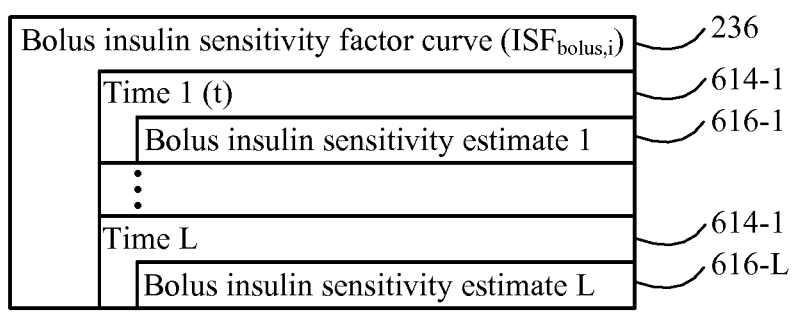

FIG. 7 provides further details on a basal insulin sensitivity curve estimate ($ISF_{basal,i}$) 234 for a subject. The basal insulin sensitivity curve estimate ($ISF_{basal,i}$) 234 includes a basal insulin sensitivity estimate 612-$y$ for each time t 610-$y$ across a particular recurring time period, such as a day, a week or a month. In some embodiments, two or more, three or more, or five or more basal insulin sensitivity curve estimates ($ISF_{basal,i}$) 234 are combined to form an updated basal insulin sensitivity curve in accordance with the present disclosure. FIG. 7 also provides further details on a bolus insulin sensitivity curve estimate ($ISF_{bolus,i}$) 236 for a subject. The bolus insulin sensitivity curve estimate ($ISF_{bolus,i}$) 236 includes a bolus insulin sensitivity estimate 616-$y$ for each time t 614-$y$ across a particular recurring time period, such as a day, a week or a month. In some embodiments, two or more, three or more, or five or more bolus insulin sensitivity curve estimates ($ISF_{bolus,i}$) 236 are combined to form an updated bolus insulin sensitivity curve in accordance with the present disclosure.

In some embodiments, the insulin regimen monitoring module 204 is accessible within any browser (phone, tablet, laptop/desktop). In some embodiments the insulin regimen monitoring module 204 runs on native device frameworks, and is available for download onto the monitoring device 250 running an operating system 202 such as Android or iOS.

In some implementations, one or more of the above identified data elements or modules of the monitoring device 250 for estimating parameters in an insulin medicament dosage regimen are stored in one or more of the previously described memory devices, and correspond to a set of instructions for performing a function described above. The above-identified data, modules or programs (e.g., sets of instructions) need not be implemented as separate software programs, procedures or modules, and thus various subsets of these modules may be combined or otherwise re-arranged in various implementations. In some implementations, the memory 192 and/or 290 optionally stores a subset of the modules and data structures identified above. Furthermore, in some embodiments the memory 192 and/or 290 stores additional modules and data structures not described above.

In some embodiments, a monitoring device 250 for estimating parameters in an insulin medicament dosage regimen is a smart phone (e.g., an iPHONE), laptop, tablet computer, desktop computer, or other form of electronic device (e.g., a gaming console). In some embodiments, the monitoring device 250 is not mobile. In some embodiments, the monitoring device 250 is mobile.

FIG. 3 provides a further description of a specific embodiment of a monitoring device 250 in accordance with the instant disclosure. The monitoring device 250 illustrated in FIG. 3 has one or more processing units (CPU's) 274, peripherals interface 370, memory controller 368, a network or other communications interface 284, a memory 192 (e.g., random access memory), a user interface 278, the user interface 278 including a display 282 and input 280 (e.g., keyboard, keypad, touch screen), an optional accelerometer 317, an optional GPS 319, optional audio circuitry 372, an optional speaker 360, an optional microphone 362, one or more optional intensity sensors 364 for detecting intensity of contacts on the monitor device 250 (e.g., a touch-sensitive surface such as a touch-sensitive display system 282 of the monitor device 250), an optional input/output (I/O) subsystem 366, one or more optional optical sensors 373, one or more communication busses 212 for interconnecting the aforementioned components, and a power supply 276 for powering the aforementioned components.

In some embodiments, the input 280 is a touch-sensitive display, such as a touch-sensitive surface. In some embodiments, the user interface 278 includes one or more soft keyboard embodiments. The soft keyboard embodiments may include standard (QWERTY) and/or non-standard configurations of symbols on the displayed icons.

The monitoring device 250 illustrated in FIG. 3 optionally includes, in addition to accelerometer(s) 317, a magnetometer (not shown) and a GPS 319 (or GLONASS or other global navigation system) receiver for obtaining information concerning the location and orientation (e.g., portrait or landscape) of the monitoring device 250 and/or for determining an amount of physical exertion by the subject or other physiological measurements 240.

It should be appreciated that the monitoring device 250 illustrated in FIG. 3 is only one example of a multifunction device that may be used for estimating parameters in an insulin medicament dosage regimen for a subject, and that the monitoring device 250 optionally has more or fewer components than shown, optionally combines two or more components, or optionally has a different configuration or arrangement of the components. The various components shown in FIG. 3 are implemented in hardware, software, firmware, or a combination thereof, including one or more signal processing and/or application specific integrated circuits.

Memory 192 of the monitoring device 250 illustrated in FIG. 3 optionally includes high-speed random access memory and optionally also includes non-volatile memory, such as one or more magnetic disk storage devices, flash memory devices, or other non-volatile solid-state memory devices. Access to memory 192 by other components of the monitoring device 250, such as CPU(s) 274 is, optionally, controlled by the memory controller 368.

The peripherals interface 370 can be used to couple input and output peripherals of the device to CPU(s) 274 and memory 192. The one or more processors 274 run or execute various software programs and/or sets of instructions stored in memory 192, such as the insulin regimen monitoring module 204, to perform various functions for the monitoring device 250 and to process data.

In some embodiments, the peripherals interface 370, CPU(s) 274, and memory controller 368 are, optionally, implemented on a single chip. In some other embodiments, they are, optionally, implemented on separate chips.

RF (radio frequency) circuitry of network interface 284 receives and sends RF signals, also called electromagnetic signals. In some embodiments, the insulin medicament regimen 206, the first data set 220, and/or the third data set 238 is received using this RF circuitry from one or more devices such as a glucose sensor 102 associated with a subject, an insulin pen 104 associated with the subject and/or the processing device 200. In some embodiments, the RF circuitry 108 converts electrical signals to/from electromagnetic signals and communicates with communications networks and other communications devices, glucose sensors 102, insulin pens 104, and/or the data processing device 200 via the electromagnetic signals. The RF circuitry 284 optionally includes well-known circuitry for performing these functions, including but not limited to an antenna system, an RF transceiver, one or more amplifiers, a tuner, one or more oscillators, a digital signal processor, a CODEC chipset, a subscriber identity module (SIM) card, memory, and so forth. The RF circuitry 284 optionally communicates with the communication network 106. In some embodiments, the circuitry 284 does not include RF circuitry and, in fact, is connected to the network 106 through one or more hard wires (e.g., an optical cable, a coaxial cable, or the like).

In some embodiments, the audio circuitry 372, the optional speaker 360, and the optional microphone 362 provide an audio interface between the subject and the monitoring device 250. The audio circuitry 372 receives audio data from the peripherals interface 370, converts the audio data to electrical signals, and transmits the electrical signals to the speaker 360. The speaker 360 converts the electrical signals to human-audible sound waves. The audio circuitry 372 also receives electrical signals converted by the microphone 362 from sound waves. The audio circuitry 372 converts the electrical signal to audio data and transmits the audio data to the peripherals interface 370 for processing. The audio data is, optionally, retrieved from and/or transmitted to the memory 192 and/or the RF circuitry 284 by the peripherals interface 370.

In some embodiments, the power supply 276 optionally includes a power management system, one or more power sources (e.g., battery, alternating current (AC)), a recharging system, a power failure detection circuit, a power converter or inverter, a power status indicator (e.g., a light-emitting diode (LED)) and any other components associated with the generation, management and distribution of power in portable devices.

In some embodiments, the monitoring device 250 optionally also includes one or more optical sensors 373. The optical sensor(s) 373 optionally include charge-coupled device (CCD) or complementary metal-oxide semiconductor (CMOS) phototransistors. The optical sensor(s) 373 receive light from the environment, projected through one or more lens, and converts the light to data representing an image. The optical sensor(s) 373 optionally capture still images and/or video. In some embodiments, an optical sensor is located on the back of the monitoring device 250, opposite the display 282 on the front of the device 250, so that the input 280 is enabled for use as a viewfinder for still and/or video image acquisition. In some embodiments, another optical sensor 373 is located on the front of the monitoring device 250 so that the subject's image is obtained (e.g., to verify the health or condition of the subject, to determine the physical activity level of the subject, to help diagnose a subject's condition remotely, to acquire physiological measurements 240, etc.).

As illustrated in FIG. 3, a monitoring device 250 preferably comprises an operating system 202 that includes procedures for handling various basic system services. The operating system 202 (e.g., iOS, DARWIN, RTXC, LINUX, UNIX, OS X, WINDOWS, or an embedded operating system such as VxWorks) includes various software components and/or drivers for controlling and managing general system tasks (e.g., memory management, storage device control, power management, etc.) and facilitates communication between various hardware and software components.

In some embodiments the monitoring device 250 is a smart phone. In other embodiments, the monitoring device 250 is not a smart phone but rather is a tablet computer, desktop computer, emergency vehicle computer, or other form or wired or wireless networked device. In some embodiments, the monitoring device 250 has any or all of the circuitry, hardware components, and software components found in the monitoring device 250 depicted in FIG. 2 or 3. In the interest of brevity and clarity, only a few of the possible components of the monitoring device 250 are shown in order to better emphasize the additional software modules that are installed on the monitoring device 250.

While the system 48 disclosed in FIG. 1 can work standalone, in some embodiments it can also be linked with electronic medical records to exchange information in any way.

Figure 4A:
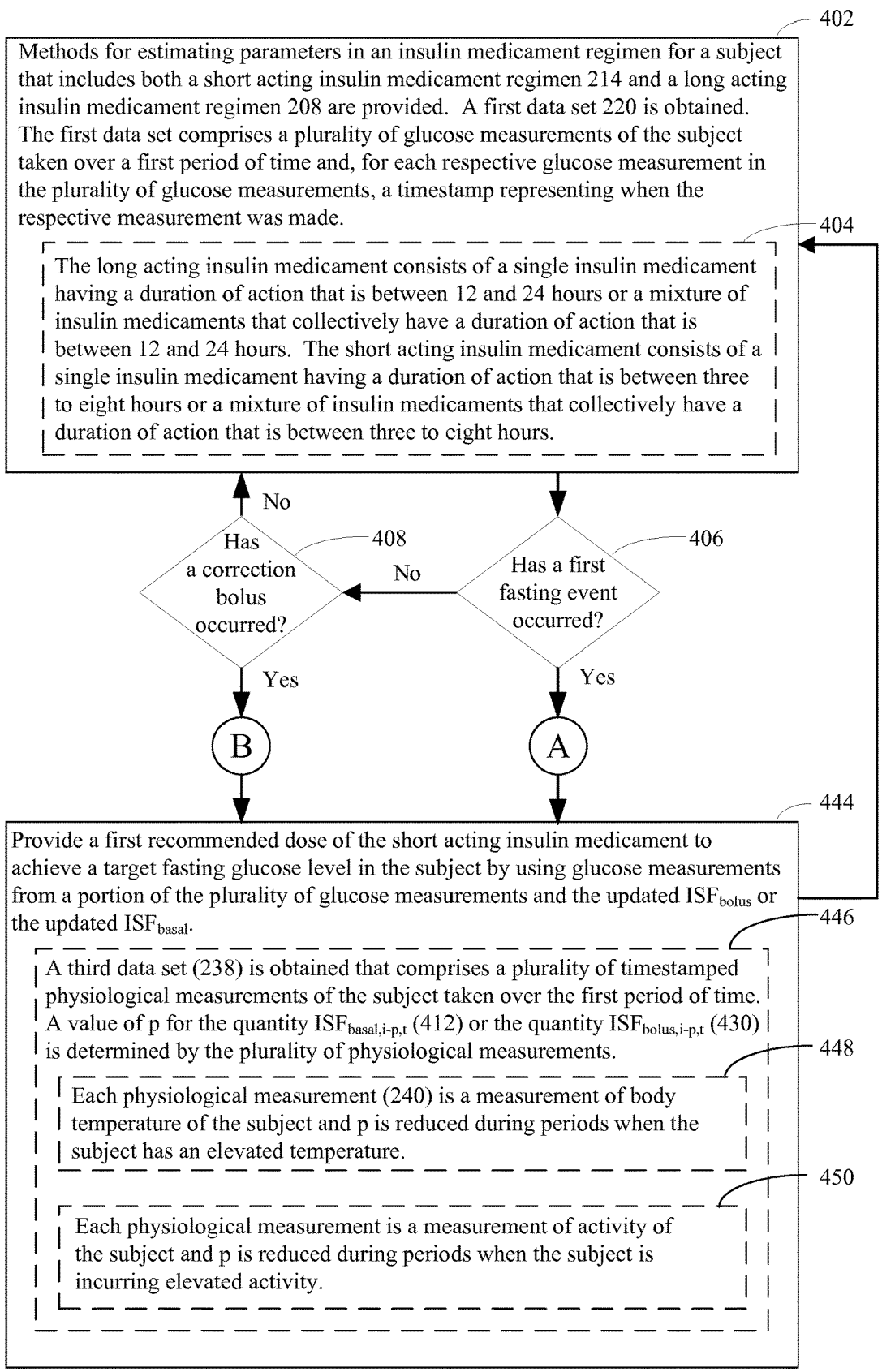
Figure 4B:
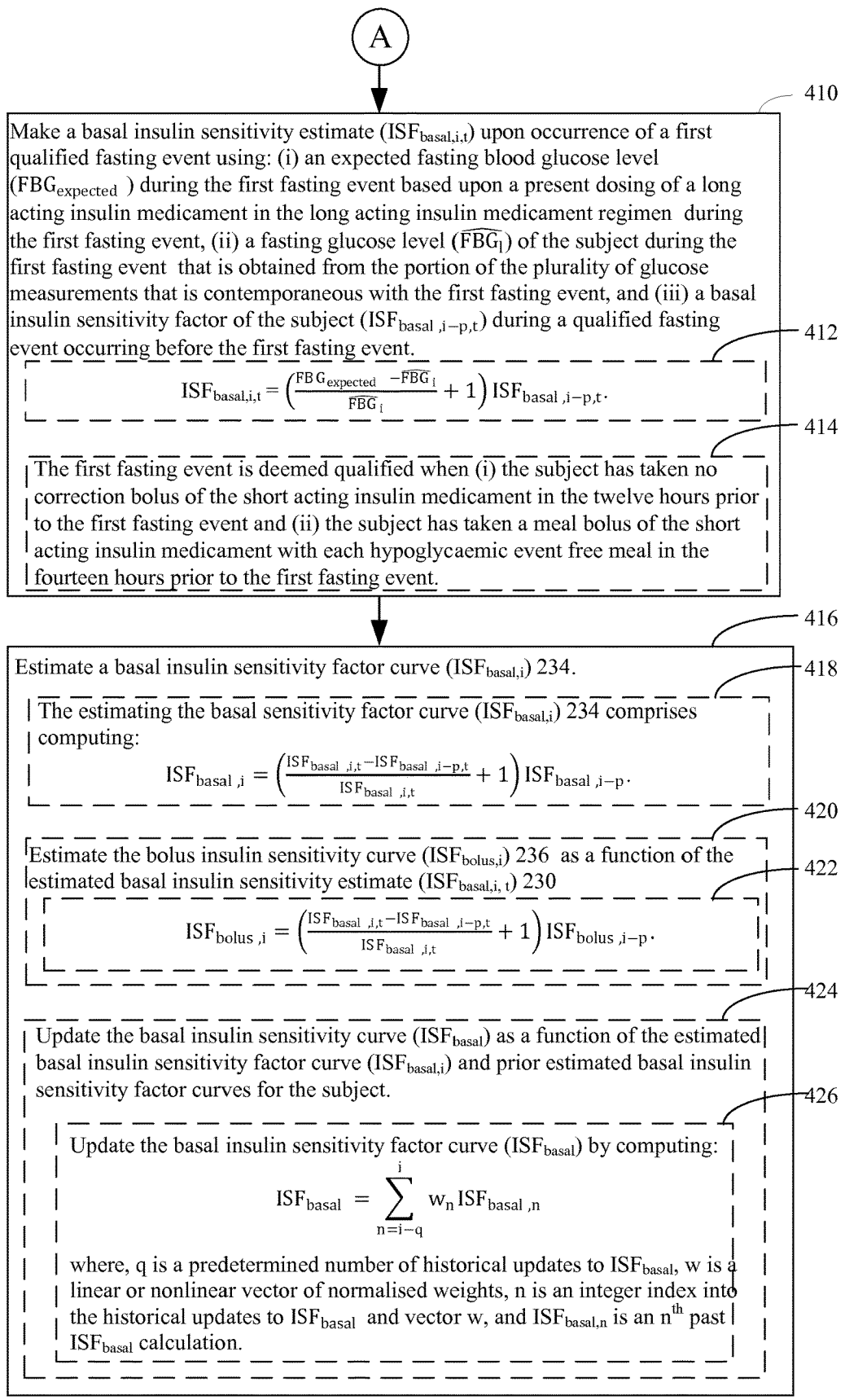

Now that details of a system 48 for estimating parameters in an insulin medicament dosage regimen 206 have been disclosed, details regarding a flow chart of processes and features of the system, in accordance with an embodiment of the present disclosure, are disclosed with reference to FIGS. 4A through 4C. In some embodiments, these processes are carried out by the monitoring device 250 described above, which comprises one or more processors 274 and a memory 192/290. The memory stores instructions that, when executed by the one or more processors, perform the processes disclosed with reference to FIGS. 4A through 4C and that are described below. In some embodiments, such processes and features of the system are carried out by the insulin regimen monitoring module 204 illustrated in FIGS. 2 and 3.

Figure 8:
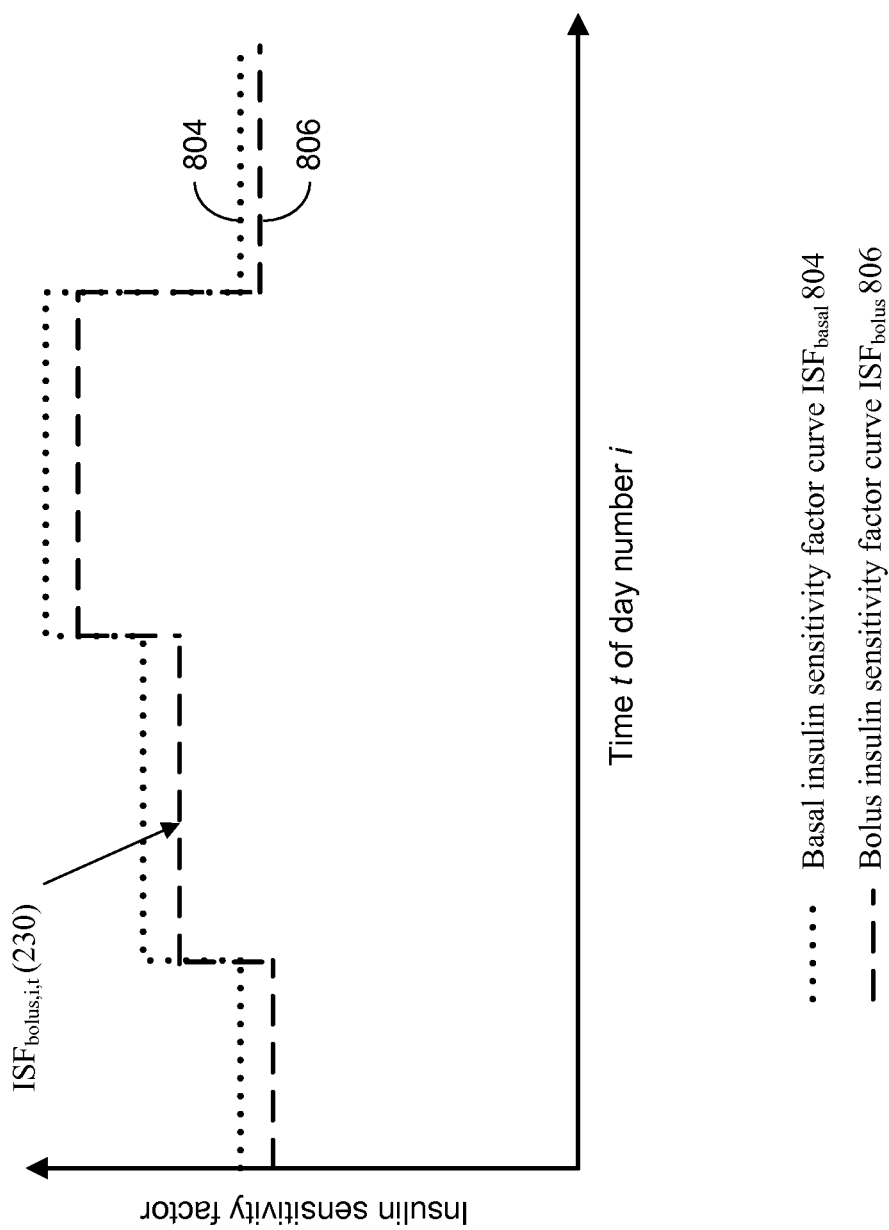
FIG. 8 illustrates a basal (long acting) insulin sensitivity factor curve ($ISF_{basal}$) and a bolus (short acting) insulin sensitivity factor curve ($ISF_{bolus}$) over the course of a time period, such as a day, in order to illustrate how the insulin sensitivity factor of a subject varies over this course of such a time period.

Block 402. With reference to block 402 of FIG. 4A, the goal of many insulin therapies is to match as closely as possible normal physiologic insulin secretion to control fasting and postprandial plasma glucose. This is done with an insulin medicament regimen 206 for the subject. In the present disclosure, the insulin medicament regimen 206 comprises a long acting insulin medicament regimen 208 and a short acting insulin medicament regimen 214. In the disclosure, the insulin sensitivity factor (ISF) and the carb-to-insulin ratio (CIR) are updated based on the response of a subject to fast and long acting insulin medicament injection events. Two parameters of an insulin medicament regimen 206 that can be used in dosage calculations for long and fast acting insulin medicaments are defined herein as the basal insulin sensitivity factor curve $ISF_{basal}$ and the bolus insulin sensitivity factor curve $ISF_{bolus}$. These two parameters are different for each subject and they describe the sensitivity of a respective subject to long and fast acting insulin medicaments, and are proportional to each other. The ISF sensitivity can be different for different times of the day, as illustrated in FIG. 8, and this is why the ISF sensitivity is expressed as ISF curves. Moreover, as seen in FIG. 8, $ISF_{basal}$ 804 and $ISF_{bolus}$ 806 each vary throughout the day but are proportional to each other throughout the day. The present disclosure advantageously takes advantage of this proportionality between $ISF_{basal}$ 804 and $ISF_{bolus}$ 806 to provide improved, more accurate ISF curves.

In some embodiments, the short acting insulin medicament used in the short acting insulin medicament regimen 214 consists of a single insulin medicament having a duration of action that is between three to eight hours or a mixture of insulin medicaments that collectively have a duration of action that is between three to eight hours. Examples of such short acting insulin medicaments include, but are not limited, to Lispro (HUMALOG, May 18, 2001, insulin lispro [rDNA origin] injection, [prescribing information], Indianapolis, Ind.: Eli Lilly and Company), Aspart (NOVOLOG, July 2011, insulin aspart [rDNA origin] injection, [prescribing information], Princeton, N.J., NOVO NORDISK Inc., July, 2011), Glulisine (Helms Kelley, 2009, "Insulin glulisine: an evaluation of its pharmacodynamic properties and clinical application," Ann Pharmacother 43:658-668), and Regular (Gerich, 2002, "Novel insulins: expanding options in diabetes management," Am J Med. 113:308-316).

In some embodiments, the long acting insulin medicament used in the long acting insulin medicament regimen 208 consists of a single insulin medicament having a duration of action that is between 12 and 24 hours or a mixture of insulin medicaments that collectively have a duration of action that is between 12 and 24 hours. In some embodiments, long acting insulin medicaments suitable for use in the long acting insulin medicament regimen 208 are those insulin medicaments having a duration of action that is between 12 and 24 hours or a mixture of insulin medicaments that collectively have a duration of action that is between 12 and 24 hours. Examples of such long acting insulin medicaments include, but are not limited to, Insulin Degludec (developed by NOVO NORDISK under the brand name Tresiba), NPH (Schmid, 2007, "New options in insulin therapy. J Pediatria (Rio J). 83(Suppl 5):S146-S155), Glargine (LANTUS, Mar. 2, 2007, insulin glargine [rDNA origin] injection, [prescribing information], Bridgewater, N.J.: Sanofi-Aventis), and Determir (Plank et al., 2005, "A double-blind, randomized, dose-response study investigating the pharmacodynamic and pharmacokinetic properties of the long-acting insulin analog detemir," Diabetes Care 28:1107-1112).

In the method, a first data set 220 is obtained. The first data set comprises a plurality of glucose measurements of the subject taken over a first period of time and, for each respective glucose measurement in the plurality of glucose measurements, a timestamp representing when the respective measurement was made. In some embodiments, each glucose measurement 222 is an autonomous glucose measurement. The FREESTYLE LIBRE CGM by ABBOTT ("LIBRE") is an example of a glucose sensor that may be used as a glucose sensor 102 that makes autonomous glucose measurements. The LIBRE allows calibration-free glucose measurements with an on-skin coin-sized sensor, which can send up to eight hours of data to a reader device (e.g., the processing device 200 and/or the monitoring device 250) via near field communications, when brought close together. The LIBRE can be worn for fourteen days in all daily life activities.

In the method, a second data set is obtained from one or more insulin pens used by the subject to apply the insulin medicament dosage regimen, the second data set comprises a plurality of insulin medicament records, each insulin medicament record in the plurality of medicament records comprises: (i) a respective insulin medicament injection event including an amount of insulin medicament injected into the subject using a respective insulin pen in the one or more insulin pens (ii) a corresponding electronic timestamp that is automatically generated by the respective insulin pen upon occurrence of the respective insulin medicament injection event, and (iii) a type of insulin medicament, wherein the type of insulin medicament is a short acting insulin medicament or a long acting insulin medicament The first and second data set systematically provides timestamped data, and thereby contributes to the reliability of the estimated parameters, and the robustness of the estimator. If for example a change in insulin sensitivity is not detected by the ISF estimator, the next ISF calculation will be less correct, as a new estimate is based on a previous estimate. On the contrary, an efficient detection of a change in ISF will increase the validity of the estimated parameters. Therefore, the frequency of glucose measurements influences the ability to resolve metabolic events that can be identified in the blood glucose, and thereby identify insulin related events. As the injection data is provided directly by one or more insulin pens, the quality of the estimated parameters increases, and the systematicly obtained data enables further adherence categorization based on stamped time-insulin injections. Therefore, ISF estimator utilizes the benefit of insulin dose and glucose data systematically provided an insulin injection device and glucose measuring device.

In some embodiments, the first data set comprises autonomous glucose measurements that are taken from the subject at an interval rate of 5 minutes or less, 3 minutes or less, or 1 minute or less. However, the present disclosure is not limited to the use of first data sets 220 that comprises autonomous glucose measurements. In some embodiments, the first data set 220 comprises nonautonomous glucose measurements or a composite of autonomous and nonautonomous glucose measurements Blocks 406 and 408. In the present disclosure, when a fasting event has occurred (406-Yes), process control turns to steps 410 and 416 of FIG. 4B. On the other hand, when a correction bolus injection event has occurred (408-Yes), process control turns to steps 428 and 432 of FIG. 4C. In other instances, where a fasting event has not occurred (406-No), or a correction bolus has not occurred (408-No) process control waits until a fasting event or a bolus correction is detected. In some instances where the subject exhibits poor adherence to the insulin medicament regimen, process control suspends altogether until adherence to the insulin medicament regimen improves.

In some embodiments, the fasting event is detected autonomously using a fasting detection algorithm and the glucose measurements in the first data set 220. There are a number of methods for detecting a fasting event using glucose measurements 222 from a glucose monitor 102. For instance, in some embodiments a first fasting event is identified in a first time period (e.g., a period of 24 hours) encompassed by the plurality of glucose measurements in the first data set 220 by first computing a moving period of variance $\sigma_k^2$ across the glucose measurements, where:

$$\sigma_k^2 = \left(\frac{1}{M} \sum_{i=k-M}^{k} (G_i - \overline{G})\right)^2$$

and where, $G_i$ is the $i^{th}$ glucose measurement in the portion k of the plurality of glucose measurements considered, M is a number of glucose measurements in the plurality of glucose measurements and represents a contiguous predetermined time span, $\overline{G}$ is the mean of the M glucose measurements selected from the plurality of glucose measurements of the first data set 220, and k is within the first time period. As an example, the glucose measurements may span several days or weeks, with glucose measurements taken every five minutes. A first time period k (e.g., one day) within this overall time span is selected and thus the portion k of the plurality of measurements is examined for a period of minimum variance. The first fasting period is deemed to be the period of minimum variance $$\min_k \sigma_k^2$$

within the first time period. Next, the process is repeated with portion k of the plurality of glucose measurements by examining the next portion k of the plurality of glucose measurements for another period of minimum variance thereby assigning another fasting period.

Turning to block 408 of FIG. 4A, in some embodiments, the correction bolus injection event is determined by pen injection data received from the one or more insulin pens 104. In some embodiments, a bolus injection event is determined by mapping the pen injection data received from the one or more insulin pens 104 onto meal events that are autonomously derived by analysis of the glucose measurements 222 in the first data set 220. In such embodiments, when a pen injection event occurs shortly before or after a meal, it is deemed to be a bolus injection event. In some embodiments, for this purpose, a meal event is detected from the glucose measurements 222 in the first data set 220 by computing: (i) a first model comprising a backward difference estimate of glucose rate of change using the glucose measurements 222, (ii) a second model comprising a backward difference estimate of glucose rate of change based on Kalman filtered estimates of glucose using the glucose measurements 222, (iii) a third model comprising a Kalman filtered estimate of glucose and Kalman filtered estimate of rate of change (ROC) of glucose based on the plurality of glucose measurements 222, and/or (iv) a fourth model comprising a Kalman filtered estimate of rate of change of ROC of glucose based on the glucose measurements 222. In some such embodiments, the first model, the second model, the third model and the fourth model are each computed across the glucose measurements 222 and a meal event is identified at an instance where at least three of the four models indicate a meal event. For further disclosure on such meal event detection, see Dassau et al., 2008, "Detection of a Meal Using Continuous Glucose Monitoring," Diabetes Care 31, pp. 295-300, which is hereby incorporated by reference. See also, Cameron et al., 2009, "Probabilistic Evolving Meal Detection and Estimation of Meal Total Glucose Appearance," Journal of Diabetes Science and Technology 3(5), pp. 1022-1030, which is hereby incorporated by reference.

In some embodiments, only those bolus injection events and those fasting events that are deemed to be insulin medicament regimen 206 adherent are used for the basal insulin sensitivity estimates ($ISF_{basal,i,t}$) 230 and the bolus insulin sensitivity estimates ($ISF_{bolus,i,t}$) 232. In other words, in some embodiments, only those bolus injection events that are deemed insulin medicament regimen 206 adherent will trigger the condition 408-Yes. Moreover, only those fasting events that are deemed insulin medication regimen 206 adherent will trigger the condition 406-Yes. Example 1, below, illustrates a way in which a determination is made as to whether a bolus injection event or a fasting event is insulin regimen adherent. Moreover, European Patent Application Number EP16177080.5, entitled "Regimen Adherence Measure for Insulin Treatment Base on Glucose Measurement and Insulin Pen Data," filed Jun. 30, 2016, which is hereby incorporated by reference, discloses techniques for identifying and classifying fasting events as adherent or nonadherent. In some embodiments, only those fasting events that are classified as "basal regimen adherent" in accordance with European Patent Application Number EP16177080.5 will trigger the condition 406-Yes in the present disclosure. Further, European Patent Application Number EP16177080.5, discloses techniques for identifying and classifying meal events as "bolus regimen adherent" or "bolus regimen nonadherent." In some embodiments, only those bolus injection event that are associated with meals that are classified as "bolus regimen adherent" in accordance with European Patent Application Number EP16177080.5 will trigger the condition 408-Yes in the present disclosure.

Block 410. Turning to block 410 of FIG. 4B, in the case where a first qualified fasting event occurred (406-Yes), a basal insulin sensitivity estimate (ISF$_{basal,i,t}$) 230 is made using: (i) an expected fasting blood glucose level based upon a present dosing of a long acting insulin medicament in the long acting insulin medicament regimen (FBG$_{expected}$) during the first fasting event, (ii) a fasting glucose level of the subject during the first fasting event ($\widetilde{FBG}_i$) that is obtained from the portion of the plurality of glucose measurements that is contemporaneous with the first fasting event, and (iii) a basal insulin sensitivity factor of the subject during a qualified fasting event occurring before the first fasting event (ISF$_{basal,i-p,t}$).

Referring to block 412 of FIG. 4B, in some such embodiments, the basal insulin sensitivity estimate (ISF$_{basal,i,t}$) 230 is computed as:

$$ISF_{basal,i,t} = \left(\frac{FBG_{expected} - \widetilde{FBG}_i}{\widetilde{FBG}_i} + 1\right) ISF_{basal,i-p,t}.$$

FIG. 9A illustrates the change in the value for ISF$_{basal,i,t}$ 230 due to the new basal update computed in block 412 of FIG. 4B.

Computation of FGB$_{expected}$. In some embodiments FBG$_{expected}$ (expected fasting blood glucose level) is a fasting blood glucose level that is obtained based upon trusted information. That is, information obtained about a subject during a period of time when the subject was adherent with the long acting insulin medicament regimen 208, denoted here as time period p. In some embodiments, FBG$_{expected}$ is obtained based on the present dosing of the long acting insulin medicament for the given time period in which the fasting event occurred (t), as set forth in the long acting insulin medicament regimen 208 (FIGS. 2 and 3), as well as the basal insulin sensitivity factor for the subject at time (t) obtained from the existing basal insulin sensitivity curve (ISF$_{basal,i-1}$) 904 of FIG. 9. This information is trusted because the current fasting event has already been determined to occur during a time when the subject was insulin regimen adherent. In other embodiments, FBG$_{expected}$ is calculated by looking up the glucose measurements 222 of the subject in the first data set 220 for the date and period of time that corresponds to the last insulin regimen adherent fasting period of the subject (e.g., the fasting period just prior to the fasting period that triggered the last instance of the condition 406-Yes of FIG. 4A). The below example illustrates one way in which a fasting event is qualified as insulin regimen adherent. Moreover, European Patent Application Number EP16177080.5, entitled "Regimen Adherence Measure for Insulin Treatment Based on Glucose Measurement and Insulin Pen Data," filed Jun. 30, 2016, which is hereby incorporated by reference, discloses techniques for identifying and classifying fasting events as adherent or nonadherent. In some embodiments, $\widetilde{FBG}_{ad}$ are the glucose measurements from the fasting event that is classified as "basal regimen adherent" in accordance with European Patent Application Number EP16177080.5 that is prior in time to the fasting event that triggered the last instance of condition 406-Yes in FIG. 4A in the present disclosure. Thus, in some embodiments, FBG$_{expected}$ is computed as:

$$FBG_{expected} = \widetilde{FBG}_{ad} - ISF_{basal,i-p,t} \Delta U_{basal}$$

where,
i indicates the current day,
t is the time of day,
$\widetilde{FBG}_{ad}$ is a glucose measurement 222 of the subject contemporaneous with the last qualified (e.g., insulin regimen adherent) fasting event of the subject (could also be denoted $\widetilde{FBG}_{basal,i-p}$), or some other measure of central tendency of a plurality of glucose measurements 222 of the subject contemporaneous with the last qualified fasting event of the subject,
ISF$_{basal,i-p,t}$ is the basal insulin sensitivity factor value taken at time t from the basal insulin sensitivity estimate curve (ISF$_{basal,i-p}$) (e.g., basal insulin sensitivity estimate curve ISF$_{basal,i-1}$ 908 of FIG. 9A when p is 1), at time t, where p typically has the value one but may have some greater value when the last fasting period (p=1) corresponds to a period in which the subject was not insulin regimen adherent, $$\Delta U_{basal} = U_{basal,i} - U_{basal,ad},$$

U$_{basal,i}$ is, in some embodiments, the dosage of the long acting insulin medicament 210 for the current time period i (e.g., the current epoch 212) specified by the long acting insulin medicament regimen 208, and, in other embodiments, is the amount of long acting insulin medicament 210 the subject has actually taken in the current time period i, as determined from injection event records from insulin pens 104, where it will be appreciated that U$_{basal,i}$ may be equivalently drawn from either source when the instant fasting period that triggered condition 406-A is long acting insulin regimen adherent, and U$_{basal,ad}$ is, in some embodiments, the dosage of the long acting insulin medicament 210 for the time that is contemporaneous with the last qualified (e.g., insulin regimen adherent) fasting event of the subject, and, in other embodiments, is the amount of long acting insulin medicament 210 the subject has actually taken in the time period p that is contemporaneous with the last qualified (e.g., insulin regimen adherent) fasting event of the subject, as determined from injection event records from insulin pens 104, where it will be appreciated that U$_{basal,ad}$ may be equivalently drawn from either source because it is from a period of time when the subject was long acting insulin regimen adherent. U$_{basal,ad}$ could also be denoted U$_{basal,i-p}$.

Calculation of ($\widetilde{FBG}_i$). In some embodiments $\widetilde{FBG}_i$ is a fasting blood glucose measurement during the time (t) of the fasting event, which is obtained from the portion of the plurality of glucose measurements in the first data set 220 that is contemporaneous in time (t) with the fasting event that triggered condition 406-Yes (first fasting event). In some embodiments, the fasting event is measured over a period of three or more minutes, five or more minutes, between five minutes and thirty minutes or some other period of time. As such, in some embodiments, there is more than one glucose measurement 222 for the fasting event in the first data set 220. When this is the case ($\widetilde{FBG}_i$) is an average value, or some other measure of central tendency, of the plurality of glucose measurements 222 within the time period.

Calculation of $ISF_{basal,i-p,t}$. The value $ISF_{basal,i-p,t}$ is the prior basal insulin sensitivity factor of the subject during a qualified fasting event occurring before the present fasting event. The value $ISF_{basal,i-p,t}$ can, for example, be obtained from sampling the value at time (t) on the existing basal insulin sensitivity curve $(ISF_{basal,i,t})$ 230 of FIG. 9A. With p set to 1, meaning take $ISF_{basal,i-p,t}$ from the prior recurring time period, such as the prior day, a value for $ISF_{basal,i-1,t}$ 908 is obtained for $ISF_{basal,i-p,t}$. In this way, computation of the equation of block 412 results in a value $ISF_{basal,i,t}$ 230 that is illustrated in FIG. 9A.

Block 414. Referring to block 414 of FIG. 4B, in some embodiments, the first fasting event is deemed qualified when (i) the subject has taken no correction bolus of the short acting insulin medicament in a first predetermined period of time (e.g., twelve hours) prior to the first fasting event and (ii) the subject has taken a meal bolus of the short acting insulin medicament with each hypoglycaemic event free meal in a second predetermined time (e.g. fourteen hours) prior to the first fasting event. In some embodiments the first predetermined period of time is six hours or greater, seven hours or greater, eight hours or greater, nine hours or greater, ten hours or greater, eleven hours or greater or twelve hours or greater. In some embodiments the second predetermined period of time is ten hours or greater, eleven hours or greater, twelve hours or greater, thirteen hours or greater, fourteen hours or greater, or fifteen hours or greater.

Figure 9B:
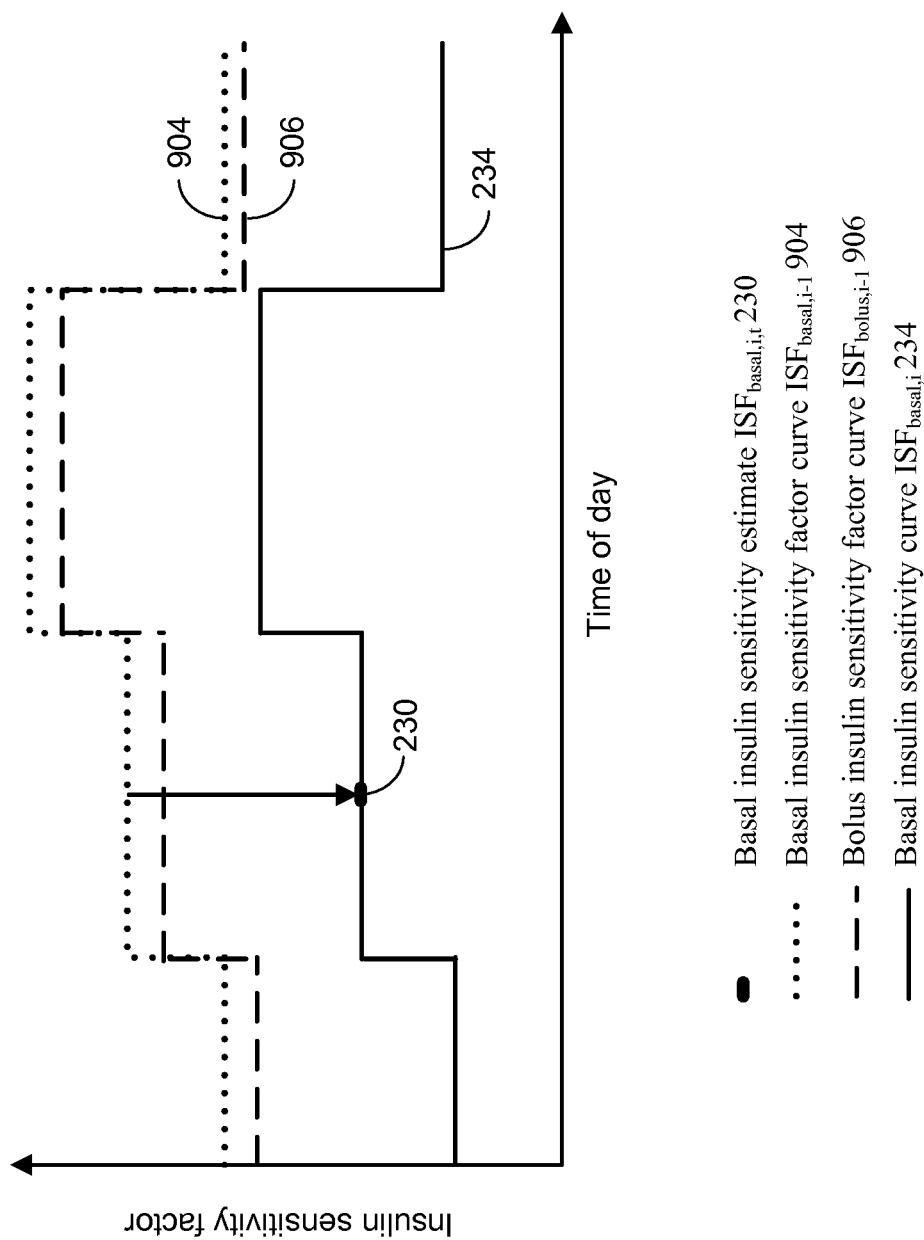
FIG. 9B illustrates estimating a basal insulin sensitivity factor curve ($ISF_{basal,i}$) once a basal insulin sensitivity estimate ($ISF_{basal,i,t}$) has been made in accordance with an embodiment of the present disclosure.

Referring to block 416 of FIG. 4B and as illustrated in FIGS. 9A and 9B, once the basal insulin sensitivity estimate $(ISF_{basal,i,t})$ 230 has been made, a basal insulin sensitivity factor curve $(ISF_{basal,i})$ 234 is estimated. Whereas the new basal insulin sensitivity factor estimate $(ISF_{basal,i,t})$ 230 represents basal insulin sensitivity of the subject at the time (t) of the occurrence of the first qualified fasting event, the basal insulin sensitivity factor curve estimate $(ISF_{basal,i})$ 234 represents the basal insulin sensitivity factor of the subject over a predetermined recurring time period, such as the course of a day. However, the new basal insulin sensitivity estimate $(ISF_{basal,i,t})$ 230 is used to update the basal insulin sensitivity factor curve estimate $(ISF_{basal,i})$ 234 in accordance with the teachings of the present disclosure. Referring to block 418, in some embodiments, the basal sensitivity factor curve estimate $(ISF_{basal,i})$ 234 is computed by the formula:

$$ISF_{basal,i} = \left(\frac{ISF_{basal,i,t} - ISF_{basal,i-p,t}}{ISF_{basal,i-p,t}} + 1\right) ISF_{basal,i-p},$$

where $ISF_{basal,i-p}$ represents a prior basal sensitivity factor curve estimate. For example, if p is from the day prior to the new fasting event and thus has the value 1, and if the basal sensitivity factor curve estimate is over the course of a recurring 24 hour time period such as a day, the basal sensitivity factor curve estimate $(ISF_{basal,i})$ 234 is computed by shifting the prior basal sensitivity factor curve estimate $(ISF_{basal,i-p})$ 904 of FIGS. 9A and 9B by the delta between the new basal insulin sensitivity estimate $(ISF_{basal,i,t})$ 230 obtained in block 410 or 412 of FIG. 4B, and the basal insulin sensitivity estimate $(ISF_{basal,i-1,t})$ 908 that is obtained by sampling the prior basal insulin sensitivity factor curve $(ISF_{basal,i-1})$ 904 of FIG. 9A or 9B for time (t), where this delta is expressed as:

$$\left(\frac{ISF_{basal,i,t} - ISF_{basal,i-p,t}}{ISF_{basal,i-p,t}} + 1\right)$$

for each sampled time t.

As illustrated by the transition from FIGS. 9A and 9B, even though the new basal insulin sensitivity estimate $(ISF_{basal,i,t})$ 230 for single time point in the time period, it is used to proportionally shift the entire basal sensitivity factor curve estimate $(ISF_{basal,i-1})$ 904 in order to calculate a new basal sensitivity factor curve estimate $(ISF_{basal,i})$ 234.

Figure 9C:
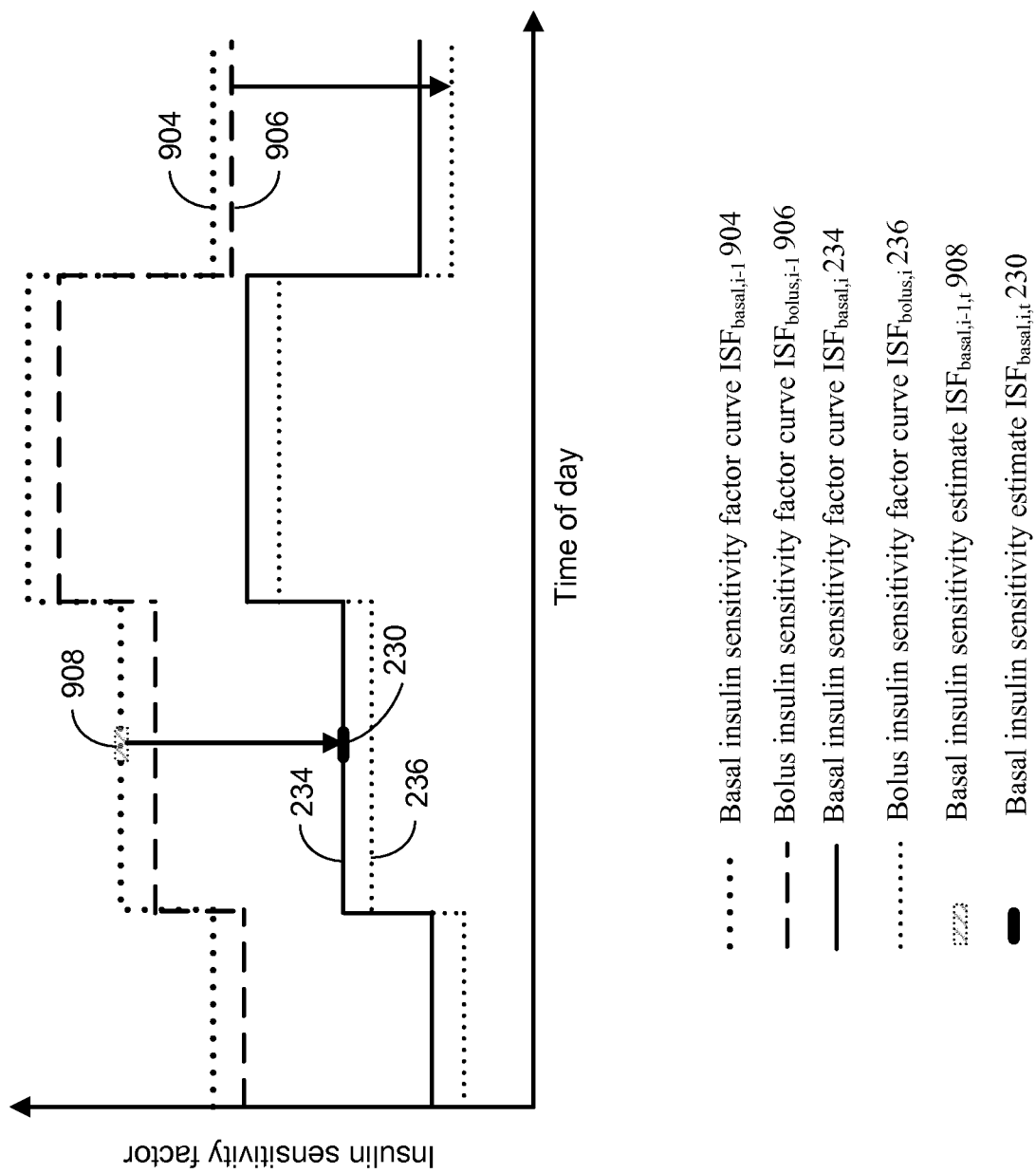
FIG. 9C illustrates computation of a bolus insulin sensitivity curve estimate ($ISF_{bolus,i}$) as a function of the newly estimated basal insulin sensitivity factor curve ($ISF_{basal,i}$) is accordance with an embodiment of the present disclosure.

Referring to block 420 and FIG. 9C, in some embodiments, further estimates are made. For instance, in some embodiments the bolus insulin sensitivity curve $(ISF_{bolus,i})$ 236 is estimated as a function of the newly estimated basal insulin sensitivity estimate $(ISF_{basal,i,t})$ 230. That is, when the basal insulin sensitivity estimate $(ISF_{basal,i,t})$ 230 is estimated as described above, it is used to estimate the bolus insulin sensitivity curve $(ISF_{bolus,i})$ 236. Referring to block 422 of FIG. 4B, in some embodiments, the estimating of the bolus insulin sensitivity curve $(ISF_{bolus,i})$ 236 as a function of the estimated basal insulin sensitivity factor estimate $(ISF_{basal,i,t})$ 230 comprises computing:

$$ISF_{bolus,i} = \left(\frac{ISF_{basal,i,t} - ISF_{basal,i-p,t}}{ISF_{basal,i-p,t}} + 1\right) ISF_{bolus,i-p},$$

where $ISF_{bolus,i-p}$ represents a prior bolus sensitivity factor curve estimate and here the value t is now used to step through the bolus entire sensitivity factor curve estimate (e.g., through the entire predetermined period of the curve, such as a day). For example, if p is from the day prior to the new fasting event and thus has the value 1, and if the basal and bolus insulin sensitivity factor curve estimates are both over the course of a recurring 24 hour time period such as a day, the bolus sensitivity factor curve estimate $(ISF_{bolus,i})$ 236 is computed by shifting the prior bolus sensitivity factor curve estimate $(ISF_{bolus,i-p})$ 906 of FIGS. 9B and 9C by the delta between the new basal insulin sensitivity estimate $(ISF_{basal,i,t})$ 230, denoted $(ISF_{basal,i,t})$ 230 (where FIG. 9C now illustrates one of many sampled values $(ISF_{basal,i,t})$ 230), and the corresponding basal insulin sensitivity estimate $(ISF_{basal,i-1,t})$ 908 that is obtained by sampling the prior basal insulin sensitivity factor curve $(ISF_{basal,i-1})$ 904 of FIG. 9B or 9C for time (t), where this delta is expressed as:

$$\left(\frac{ISF_{basal,i,t} - ISF_{basal,i-p,t}}{ISF_{basal,i-p,t}} + 1\right) = \left(\frac{ISF_{basal,i}}{ISF_{basal,i-p}}\right)$$

for each sampled time t.

Referring to block 424 of FIG. 4B, the above embodiments describe the computation of a new estimated basal insulin sensitivity curve $(ISF_{basal,i})$ 234 for an $i^{th}$ time period, such as an $i^{th}$ day. Typically this $i^{th}$ time period (e.g., this $i^{th}$ day) is the present day. In some embodiments, when a new estimated basal insulin sensitivity curve $(ISF_{bolus,i})$ 234 has been made, it is then combined with one or more basal insulin sensitivity curve estimates from prior days (or other prior recurring time periods represented by the curve) in order to form an updated basal insulin sensitivity curve $(ISF_{basal})$. Referring to block 426 of FIG. 4B, in some such embodiments, this basal insulin sensitivity factor curve is updated by computing:

$$ISF_{basal} = \sum_{n=i-q}^{i} w_n ISF_{basal,n},$$

where, q is a predetermined number of historical updates to $ISF_{basal}$, w is a linear or nonlinear vector of normalized weights, n is an integer index into the historical updates to $ISF_{basal}$ and vector w, and $ISF_{basal,n}$ is an $n^{th}$ past $ISF_{basal}$ calculation. For instance, in some embodiments, a basal insulin sensitivity curve estimate $ISF_{basal,n}$ representing an earlier period of time (e.g., an earlier day) is downweighted relative to a basal insulin sensitivity curve estimate $ISF_{basal,n}$ representing a later day. This is done to emphasize the basal insulin sensitivity curve estimates from more recent days, which are more likely to have significance determining the true a basal insulin sensitivity curve of the subject. This is accomplished in one embodiment, for example, by updating the basal insulin sensitivity factor curve using the equation of block 426 by applying a first weight against the earlier basal insulin sensitivity curve estimate $ISF_{basal,n}$ and a second weight against the later basal insulin sensitivity curve estimate $ISF_{basal,n}$ where the first weight is less than the second weight. In this way, the earlier basal insulin sensitivity curve estimate $ISF_{basal,n}$ contributes less to the updated insulin sensitivity curve than the later basal insulin sensitivity curve estimate $ISF_{basal,n}$. In some embodiments, the past seven insulin sensitivity curve estimate $ISF_{basal,n}$ are combined in accordance with the equation of block 426, where the oldest basal insulin sensitivity curve estimate curve ($ISF_{basal,n-7}$) has the lowest weight, the most recent basal insulin sensitivity curve estimate $ISF_{basal,n}$ has the highest weight and the curve estimates between the oldest curve estimate and the most recent curve estimate are linearly scaled.

In another example of how the formula of block 426 is weighted in other embodiments, each $w_n$ is an independent weight for a corresponding $ISF_{basal,n}$, and each $w_n$ is (i) equal to a first value when $w_n$ weights a $ISF_{basal,n}$ that is before a threshold date and (ii) equal to a second value when $w_n$ weights a $ISF_{basal,n}$ that is after a threshold date, and the first value is smaller than the second value. In such embodiments, each basal insulin sensitivity factor curve estimate $ISF_{basal,n}$ is multiplied by a corresponding weight to form the set $\{w_1 a_1, w_2 a_2, \ldots, w_R a_R\}$, where each $a_n$ in the set represents a $ISF_{basal,n}$ and this set is summed to form the basal insulin sensitivity factor curve $ISF_{basal}$. The weight w, of those basal insulin sensitivity factor curve estimates $ISF_{basal,n}$ that occur before the threshold date are each equal to a first value and those basal insulin sensitivity factor curve estimates $ISF_{basal,n}$ that occur after the threshold date are each equal to a second value. In some embodiments, the threshold date is three days prior to the date of the present qualifying fasting event of the last instance of step 406-Yes, five days prior to the date of the present qualifying fasting event of the last instance of step 406-Yes, or seven days prior to the date of the present qualifying fasting event of the last instance of step 406-Yes. In other words, in some embodiments, the updated basal insulin sensitivity factor curve $ISF_{basal}$ formed using the basal insulin sensitivity factor curve estimates $ISF_{basal,n}$ occurring more than three days ago, more than five days ago, or more than seven days ago are each weighted against a first weight whereas basal insulin sensitivity factor curve estimates $ISF_{basal,n}$ formed more recently are each weighted against a second weight. In some such embodiments, the first value is zero and the second value is 1.

In some embodiments, the basal insulin sensitivity factor curve estimates $ISF_{basal,n}$ are combined by taking a weighted average or a measure of central tendency of the basal insulin sensitivity factor curve estimate $ISF_{basal,n}$ at each time t across the curves estimates. That is, for each time t in the curve, each of the past basal insulin sensitivity factor curve estimates $ISF_{basal,n}$ are sampled at time t for the basal insulin sensitivity factor at that time t and the weighted average or measure of central tendency of these values is used to form a point for time t on the updated basal insulin sensitivity factor curve. In some embodiments, the measure of central tendency can be, for example, an arithmetic mean, weighted mean, midrange, midhinge, trimean, Winsorized mean, median, or mode of such values. In some embodiments, the plurality of basal insulin sensitivity factor curve estimate $ISF_{basal,n}$ are combined into the basal insulin sensitivity factor curve $ISF_{basal}$ by taking a weighted average of the N most recent basal insulin sensitivity factor curve estimates $ISF_{basal,n}$ or a measure of central tendency of the N most recent basal insulin sensitivity factor curve estimates $ISF_{basal,n}$, where N is a positive integer (e.g., 1, 2, 3, 4, 5, 6, etc.). This measure of central tendency can be, for example, an arithmetic mean, weighted mean, midrange, midhinge, trimean, Winsorized mean, median, or mode of such values.

Block 428. Turning to block 428 of FIG. 4C, in the case where a correction bolus with a short acting insulin medicament occurs (408-Yes), a bolus insulin sensitivity estimate ($ISF_{bolus,i,t}$) 232 is made for the subject. This estimate makes use of (i) an expected blood glucose level ($BG_{expected}$) based upon the correction bolus with the short acting insulin medicament, (ii) the glucose level ($\widehat{FBG}_{corr,i}$) of the subject after occurrence of the correction bolus, where $\widehat{FBG}_{corr,i}$ is obtained from the portion of the plurality of glucose measurements that is contemporaneous with a period of time after the occurrence of the correction bolus, and (iii) an insulin sensitivity factor ($ISF_{bolus,i-p,t}$) of the subject estimated based upon occurrence of a prior correction bolus with the short acting insulin medicament.

Referring to block 430 FIG. 4C, in some embodiments, this bolus insulin sensitivity estimate ($ISF_{bolus,i,t}$) 232 is computed as:

$$ISF_{bolus,i,t} = \left( \frac{BG_{expected} - \widehat{BG}_{corr,i}}{\widehat{BG}_{corr,i}} + 1 \right) ISF_{bolus,i-p,t}.$$

Computation of $BG_{expected}$. In some embodiments $BG_{expected}$ is computed as:

$$BG_{expected} = \widehat{FBG}_{hyp,i} - ISF_{bolus,i-p,t} U_{corr,i}.$$

Here, $\widehat{FBG}_{hyp,i}$ is a glucose measurement 222 of the subject contemporaneous with a hyperglycaemic event after a meal event, or some other measure of central tendency of a plurality of glucose measurements 222 of the subject contemporaneous with the hyperglycaemic event. $\widehat{BG}_{hyp,i}$ is measured before the correction bolus is taken. $ISF_{bolus,i-p,t}$ is the basal insulin sensitivity factor value taken at time t from the prior bolus insulin sensitivity estimate curve $ISF_{bolus,i-p}$, at time t (e.g., the time at which the subject actually took for the bolus that triggered the instant condition 408-Yes). $U_{corr,i}$ is, in some embodiments, the dosage of the short acting insulin medicament 214 for the current time period i (e.g., the current date/time 218) specified by the short acting insulin medicament regimen 214, and, in other embodiments, is the amount of short acting insulin medicament 214 the subject has actually taken for the bolus that triggered the instant condition 408-Yes. $U_{corr,i}$ is the correction bolus necessary to bring the hyperglycaemic glucose level below an upper limit and into a normal range of glucose levels.

$\overline{BG}_{hyp,i}$ can also be denoted $\overline{BG}_{bolus,hyp,i}$ and $\overline{BG}_{corr,i}$ can also be denoted $\overline{BG}_{bolus,corr,i}$.

Calculation of $\overline{BG}_{corr,i}$. In some embodiments $\overline{BG}_{corr,i}$ is a blood glucose measurement during the time (t) of the bolus injection event 408-Yes, which is obtained from the portion of the plurality of glucose measurements in the first data set 220 that is contemporaneous in time (t) with the bolus injection event that triggered condition 408-Yes (the correction bolus). In some embodiments, the bolus event is measured over a period of three or more minutes, five or more minutes, between five minutes and thirty minutes or some other period of time. As such, in some embodiments, there is more than one glucose measurement 222 for the bolus event in the first data set 220. In some embodiments, when this is the case $\overline{BG}_{corr,i}$ is an average value, or some other measure of central tendency, of the plurality of glucose measurements 222 within the time period. $BG_{corr,i}$ is measured after the correction bolus is taken.

Calculation of $ISF_{bolus,i-p,t}$. The value $ISF_{bolus,i-p,t}$ is the prior bolus insulin sensitivity factor of the subject during a qualified bolus event occurring before the present bolus event. The value $ISF_{bolus,i-p,t}$ can, for example, be obtained from sampling the value at time (t) on the existing bolus insulin sensitivity curve $ISF_{bolus,i-p}$. With p set to 1, meaning take $ISF_{bolus,i-p,t}$ from the prior recurring time period, such as the prior day, a value for $ISF_{bolus,i-1,t}$ is obtained for $ISF_{bolus,i-p,t}$.

Block 432. Referring to block 432 of FIG. 4C, once the new bolus insulin sensitivity estimate ($ISF_{bolus,i,t}$) 232 is made, a bolus insulin sensitivity factor curve ($ISF_{bolus,i}$) 236 is estimated. Whereas the new bolus insulin sensitivity estimate ($ISF_{bolus,i,t}$) 232 represents bolus insulin sensitivity of the subject at the time of the correction bolus, the bolus insulin sensitivity factor curve ($ISF_{bolus,i}$) 236 represents the bolus insulin sensitivity factor of the subject over a predetermined recurring time period, such as the course of a day. However, the new bolus insulin sensitivity estimate ($ISF_{bolus,i,t}$) 232 is used to update the bolus insulin sensitivity factor curve ($ISF_{bolus,i}$) 236 in accordance with the teachings of the present disclosure. Referring to block 434 of FIG. 4C, in some embodiments, the estimating the bolus sensitivity factor curve 236 comprises computing:

$$ISF_{bolus,i} = \left(\frac{ISF_{bolus,i,t} - ISF_{bolus,i-p,t}}{ISF_{bolus,i-p,t}} + 1\right) ISF_{bolus,i-p},$$

where $ISF_{bolus,i-p}$ represents a prior bolus sensitivity factor curve estimate.

Referring to block 436, in some embodiments, further estimates are made. For instance, in some embodiments the basal insulin sensitivity curve ($ISF_{basal,i}$) 234 is estimated as a function of the newly estimated bolus insulin sensitivity estimate ($ISF_{bolus,i,t}$) 232. That is, when the estimated bolus insulin sensitivity estimate ($ISF_{bolus,i,t}$) 232 is made as described above, it is used to estimate the basal insulin sensitivity curve ($ISF_{basal,i}$) 234. Referring to block 438 of FIG. 4C, in some embodiments, the estimating the basal insulin sensitivity curve ($ISF_{basal,i}$) 234 as a function of the estimated bolus insulin sensitivity estimate ($ISF_{bolus,i,t}$) 232 comprises computing:

$$ISF_{basal,i} = \left(\frac{ISF_{bolus,i,t} - ISF_{bolus,i-p,t}}{ISF_{bolus,i-p,t}} + 1\right) ISF_{basal,i-p},$$

where $ISF_{basal,i-p}$ represents a prior basal sensitivity factor curve estimate.

Referring to block 440 of FIG. 4C, the above embodiments describe the computation of a new estimated bolus insulin sensitivity curve ($ISF_{bolus,i}$) 236 for an $i^{th}$ time period, such as an $i^{th}$ day. Typically this $i^{th}$ time period (e.g., this $i^{th}$ day) is the present day. In some embodiments, when a new estimated bolus insulin sensitivity curve ($ISF_{bolus,i}$) 236 has been estimated, it is then combined with one or more bolus insulin sensitivity curve estimates from prior days (or prior recurring time periods) in order to form an updated bolus insulin sensitivity curve ($ISF_{bolus}$). Referring to block 442 of FIG. 4C, in some embodiments, this bolus insulin sensitivity factor curve updated by computing:

$$ISF_{bolus} = \sum_{n=i-q}^{i} w_n ISF_{bolus,n},$$

where q is a predetermined number of historical updates to the bolus insulin sensitivity curve ($ISF_{bolus}$), w is a linear or nonlinear vector of normalised weights, n is an integer index into the historical updates to $ISF_{bolus}$ and vector w, and $ISF_{bolus,n}$ is an $n^{th}$ past bolus insulin sensitivity curve ($ISF_{bolus}$).

For instance, in some embodiments, a bolus insulin sensitivity curve estimate $ISF_{bolus,n}$ representing an earlier period of time (e.g., an earlier day) is downweighted relative to a bolus insulin sensitivity curve estimate $ISF_{bolus,n}$ curve representing a later day. This is done to emphasize the bolus insulin sensitivity curve estimates from more recent days, which are more likely to have significance determining the true a bolus insulin sensitivity curve of the subject. This is accomplished for example, in one embodiment, by updating the bolus insulin sensitivity factor curve using the equation of block 442 by applying a first weight against the earlier bolus insulin sensitivity curve estimate $ISF_{bolus,n}$ and a second weight against the later basal insulin sensitivity curve estimate $ISF_{bolus,n}$ where the first weight is less than the second weight. In this way, the earlier basal insulin sensitivity curve estimate $ISF_{bolus,n}$ contributes less to the updated insulin sensitivity curve than the later basal insulin sensitivity curve estimate $ISF_{bolus,n}$. In some embodiments, the past seven bolus insulin sensitivity curve estimates $ISF_{bolus,n}$ are combined in accordance with the equation of block 442, where the oldest bolus insulin sensitivity curve estimate ($ISF_{bolus,n-7}$) has the lowest weight, the most recent bolus insulin sensitivity curve estimate $ISF_{bolus,n}$ has the highest weight and the curve estimates between the oldest curve estimate and the most recent curve estimate are linearly scaled.

In another example of how the formula of block 442 is weighted, each $w_n$ is an independent weight for a corresponding $ISF_{bolus,n}$, and each $w_n$ is (i) equal to a first value when $w_n$ weights a $ISF_{bolus,n}$ that is before a threshold date and (ii) equal to a second value when $w_n$ weights a $ISF_{bolus,n}$ that is after a threshold date, and the first value is smaller than the second value. In such embodiments, each bolus insulin sensitivity factor curve estimate $ISF_{bolus,n}$ is multiplied by a corresponding weight to form the set $\{w_1a_1, w_2a_2, \ldots, w_Ra_R\}$, where each $a_n$ in the set represents a $ISF_{bolus,n}$ and this set is summed to form the updated bolus insulin sensitivity factor curve $ISF_{basal}$. The weight $w_i$ of those bolus insulin sensitivity factor curve estimates $ISF_{bolus,n}$ that occur before the threshold date are each equal to a first value and those bolus insulin sensitivity factor curve estimates $ISF_{bolus,n}$ that occur after the threshold date are each equal to a second value. In some embodiments, the threshold date is three days prior to the date of the present qualifying bolus event of the last instance of step 408-Yes, five days prior to the date of the present qualifying bolus event of the last instance of step 408-Yes, or seven days prior to the date of the present qualifying bolus event of the last instance of step 408-Yes. In other words, in some embodiments, the updated bolus insulin sensitivity factor curve $ISF_{bolus}$ formed using the bolus insulin sensitivity factor curve estimates $ISF_{bolus}$ occurring more than three days ago, more than five days ago, or more seven days ago are each weighted against a first weight whereas bolus insulin sensitivity factor curve estimates $ISF_{bolus,n}$ formed more recently are each weighted against a second weight. In some such embodiments, the first value is zero and the second value is 1.

In some embodiments, the bolus insulin sensitivity factor curve estimates $ISF_{bolus,n}$ are combined by taking a weighted average or a measure of central tendency of the bolus insulin sensitivity factor curve estimate $ISF_{bolus,n}$ at each time t across the curve estimates.

That is, for each time t in the curve, each of the past bolus insulin sensitivity factor curve estimates $ISF_{bolus,n}$ are sampled at time t for the bolus insulin sensitivity factor at that time t and the weighted average or measure of central tendency of these values is used to form a point for time t on the updated bolus insulin sensitivity factor curve. In some embodiments, the measure of central tendency can be, for example, an arithmetic mean, weighted mean, midrange, midhinge, trimean, Winsorized mean, median, or mode of such values. In some embodiments, the plurality of bolus insulin sensitivity factor curve estimates $ISF_{bolus,n}$ are combined into the bolus insulin sensitivity factor curve $ISF_{bolus}$ by taking a weighted average of the N most recent bolus insulin sensitivity factor curve estimates $ISF_{bolus,n}$ or a measure of central tendency of the N most recent basal insulin sensitivity factor curve estimates $ISF_{bolus,n}$, where N is a positive integer (e.g., 1, 2, 3, 4, 5, 6, etc.). This measure of central tendency can be, for example, an arithmetic mean, weighted mean, midrange, midhinge, trimean, Winsorized mean, median, or mode of such values.

Block 444. Advantageously, the disclosed techniques provide improved basal insulin sensitivity factor ($ISF_{basal}$) and bolus insulin sensitivity factor ($ISF_{bolus}$) curves. Referring to block 444 of FIG. 4A, in some embodiments, a first recommended dose of the short acting insulin medicament to achieve a target fasting glucose level in the subject is provided by using glucose measurements from a portion of the plurality of glucose measurements and the updated bolus insulin sensitivity factor curve $ISF_{bolus}$ or the updated basal insulin sensitivity factor curve $ISF_{basal}$.

Referring to block 446, in some embodiments a third data set 238 is obtained that comprises a plurality of timestamped physiological measurements of the subject taken over the first period of time. In some such embodiments, a value of p for the quantity $ISF_{basal,i-p,t}$ 412 or the quantity $ISF_{bolus,i-p,t}$ 430 is determined by the plurality of physiological measurements. For instance, referring to block 448 of FIG. 4A, in some embodiments each physiological measurement 240 is a measurement of body temperature of the subject and p is reduced during periods when the subject has an elevated temperature. As another example, referring to block 450 of FIG. 4A, in some embodiments each physiological measurement is a measurement of activity of the subject and p is reduced during periods when the subject is incurring elevated activity.

In some such embodiments, a value of q for the summation of block 426 or the summation of block 442 is determined by the plurality of physiological measurements. For instance, in some embodiments each physiological measurement 240 is a measurement of body temperature of the subject and q is reduced during periods when the subject has an elevated temperature. As another example, in some embodiments each physiological measurement is a measurement of activity of the subject and q is reduced during periods when the subject is incurring elevated activity.

Figure 11:
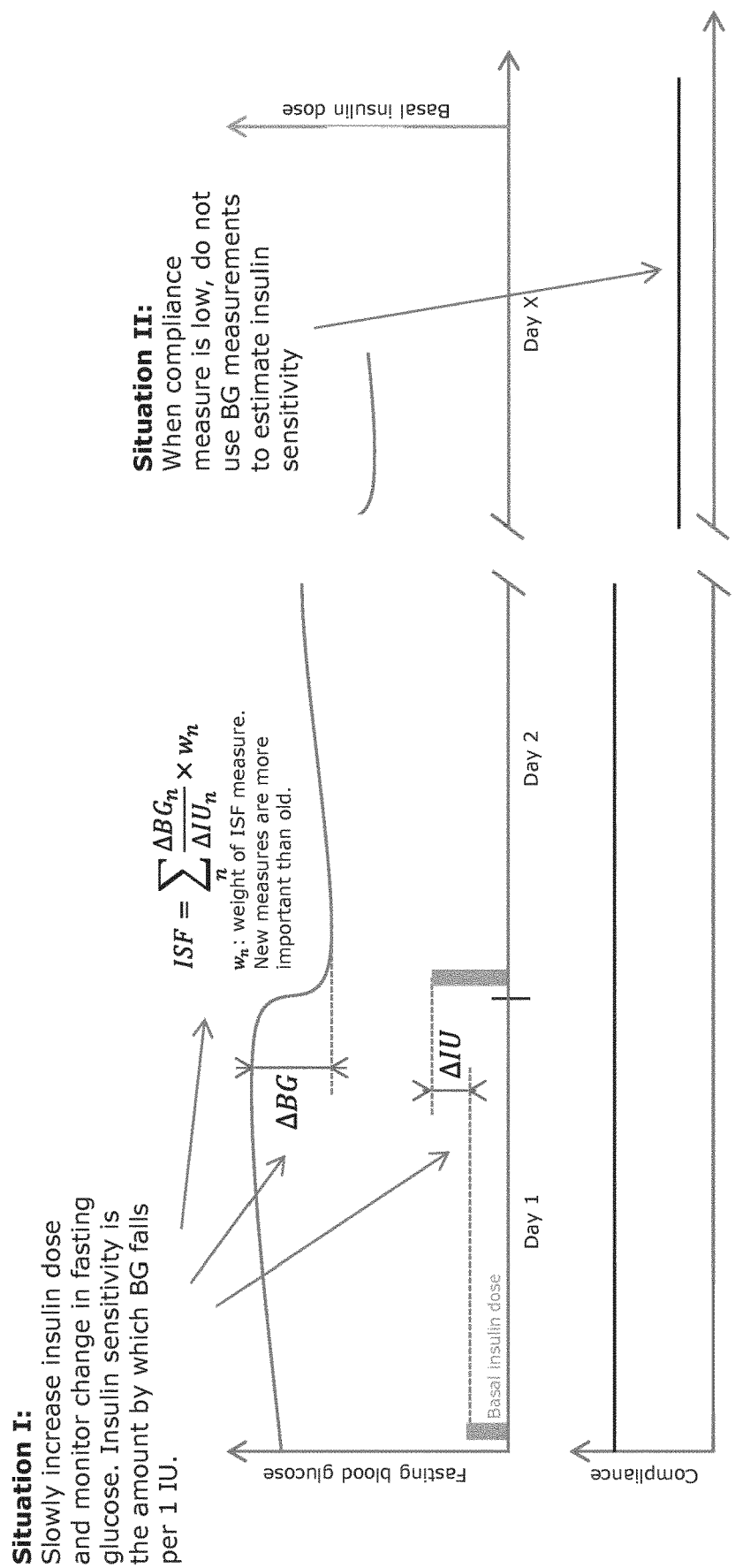
FIG. 11 illustrates how the overall adherence of the subject to an insulin medicament regimen is monitored and how the bolus insulin sensitivity curve estimation and updating is suspended during periods of time when the overall adherence of the subject to an insulin medicament regimen falls below a threshold value.

Referring to FIG. 11, in some embodiments, the overall adherence of the subject to an insulin medicament regimen is monitored using the techniques disclosed in European patent application Nos. 16177082.1, 16177083.9, and 16177090.4 each entitled "Systems and Methods for Analysis of Insulin Regimen Adherence Data," and filed Jun. 30, 2016, which are hereby incorporated by reference, and/or by the insulin regimen adherence techniques disclosed in Example 1. In some such embodiments, when the insulin medicament regimen 206 adherence falls below a threshold value (e.g., the insulin medicament regimen 206 adherence drops below 90 percent of the injection events specified by the insulin medicament regimen 206, the insulin medicament regimen 206 adherence drops below 80 percent of the injection events specified by the insulin medicament regimen 206, the insulin medicament regimen adherence drops below 70 percent of the injection events specified by the insulin medicament regimen 206, or some other threshold value based upon percentage of adherent injection events, fasting events and/or meal events) the use of fasting events or bolus insulin injection events to update the insulin sensitivity factor curves $ISF_{basal}$ and $ISF_{bolus}$, as set forth in FIGS. 4A through 4C, is suspended until such time as the insulin medicament regimen 206 adherence rises above this a threshold value, as illustrated in FIG. 11.

Example 1: Use of glucose measurements to determine whether a bolus injection event or a fasting event is insulin regimen adherent. In some embodiments, the first data set 220 comprising a plurality of glucose measurements is obtained. In some embodiments the glucose measurements are obtain autonomously, for instance by a continuous glucose monitor. In this example, in addition to the autonomous glucose measurements, insulin administration events are obtained in the form of insulin medicament records from one or more insulin pens 104 used by the subject to apply the insulin medicament regimen 206. These insulin medicament records may be in any format, and in fact may be spread across multiple files or data structures. As such, in some embodiments, the instant disclosure leverages the recent advances of insulin administration pens, which have become "smart" in the sense that they can remember the timing and the amount of insulin medicament administered in the past. One example of such an insulin pen 104 is the NovoPen 5. Such pens assists patients in logging doses and prevent double dosing. It is contemplated that insulin pens will be able to send and receive insulin medicament dose volume and timing, thus allowing the integration of continuous glucose monitors 102, insulin pens 104 and the algorithms of the present disclosure. As such, insulin medicament records from one or more insulin pens 104 is contemplated, including the wireless acquisition of such data from the one or more insulin pens 104.

In some embodiments, each insulin medicament record comprises: (i) a respective insulin medicament injection event including an amount of insulin medicament injected into the subject using a respective insulin pen in the one or more insulin pens and (ii) a corresponding electronic timestamp that is automatically generated by the respective insulin pen 104 upon occurrence of the respective insulin medicament injection event.

In some embodiments, a fasting event is identified using the glucose measurements 222 of the subject and their associated glucose measurement timestamps 224 in the first data set 220. Once a fasting event is identified, by the method described for blocks 406 and 408 above, or any other method, a classification is applied to the fasting event. The classification is one of "insulin regimen adherent" and "insulin regimen nonadherent."

A fasting event is deemed insulin regimen adherent when the acquired one or more medicament records establish, on a temporal and quantitative basis, adherence with the long acting insulin medicament regimen 208 during the fasting event. A fasting event is deemed insulin regimen nonadherent when the acquired one or more medicament records do not include one or more medicament records that establish, on a temporal and quantitative basis, adherence with the long acting insulin medicament regimen during the fasting event. In some embodiments the long acting insulin medicament regimen 208 specifies that a dose of long acting insulin medicament 210 is to be taken during each respective epoch 212 in a plurality of epochs and that a fasting event is deemed insulin regimen nonadherent when there are no medicament records for the epoch 212 associated with the fasting event. In various embodiments, each epoch in the plurality of epochs is two days or less, one day or less, or 12 hours or less. Thus, consider the case where the first data set 220 is used to identify a fasting period and the long acting insulin medicament regimen 208 specifies to take dosage A of a long acting insulin medicament 210 every 24 hours. In this example, therefore, the epoch is one day (24 hours). The fasting event is inherently timestamped because it is derived from a period of minimum variance in timestamped glucose measurements, or by other forms of analysis of the timestamped glucose measurements 222. Thus the timestamp, or period of fasting, represented by a respective fasting event is used as a starting point for examining whether the fasting event is insulin regimen adherent. For instance, if the period of fasting associated with the respective timestamp is 6:00 AM on Tuesday, May 17, what is sought in the medicament injection records is evidence that the subject took dosage A of the long acting insulin medicament in the 24 hour period (the epoch) leading up to 6:00 AM on Tuesday, May 17 (and not more or less of the prescribed dosage). If the subject took the prescribed dosage of the long acting insulin medicament during this epoch, the fasting event (and/or the basal injection event and/or the glucose measurements during this time) is deemed insulin regimen adherent. If the subject did not take the dose of the long acting insulin medicament 210 during this epoch 212 (or took more than the dose of the long acting insulin medicament during this period specified by the long acting insulin regimen 208), the fasting event (and/or the basal injection event and/or the glucose measurements during this time) is deemed to be insulin regimen nonadherent.

In some embodiments, the epoch is defined by the long acting insulin medicament regimen 208 and, so long as the subject took the amount of basal insulin required by the insulin medicament regimen 208 during the epoch (and not more), even if after the fasting event, the fasting event will be deemed insulin regimen adherent. For instance, if the epoch is one day beginning each day at just after midnight (in other words the long acting insulin medicament regimen 208 specifies one or more long acting insulin medicament dosages to be taken each day, and further defines a day as beginning and ending at midnight), and the fasting event occurs at noon, the fasting event will be deemed insulin regimen adherent provided that the subject takes the long acting insulin medicament injections prescribed for the day at some point during the day.

Continuing with this example, in some embodiments a meal event is identified from the glucose measurements 222 and the corresponding timestamps 224 in the first data 220 using a meal detection algorithm. Examples of such meal detection have been described above with reference to blocks 406 and 408. In some embodiments, a bolus injection event is deemed to be insulin regimen adherent when the injection event record for the bolus injection event indicates, on a temporal basis, a quantitative basis and a type of insulin medicament basis, adherence with the short acting insulin medicament regimen 214 with respect to the detected meal. In some embodiments, a bolus injection event is deemed insulin regimen nonadherent when the medicament record for the bolus injection event fails to indicate adherence, on a temporal basis, a quantitative basis, and a type of insulin medicament basis, with the short acting insulin medicament regimen 214 for the detected meal. For instance, consider the case where the short acting insulin medicament regimen 214 specifies that dosage A of insulin medicament B is to be taken up 30 minutes before a detected meal and that a meal that occurred at 7:00 AM on Tuesday, May 17. It will be appreciated that dosage A may be a function of the anticipated size or type of meal. What is sought in the medicament records is evidence that the subject took dosage A of insulin medicament B in the 30 minutes leading up to 7:00 AM on Tuesday, May 17 (and not more or less of the prescribed dosage). If the subject took the prescribed dosage A of the insulin medicament B during the 30 minutes leading up to the respective meal as a bolus injection, this bolus injection event will be deemed insulin regimen adherent. If the subject took a dosage A of the insulin medicament B outside the 30 minutes leading up to the respective meal (or it contained more than the prescribed dosage A of the insulin medicament B), the bolus administration will be deemed insulin regimen nonadherent. The time period of 30 minutes here is exemplary, in other embodiments the time is shorter or longer (e.g., between 15 minutes to 2 hours prior to the meal and/or is dependent upon the type of insulin medicament prescribed). In some embodiments, the short acting insulin medicament regimen 214 permits the bolus injection to be taken a short time after the meal.

In some embodiments, the short acting insulin medicament regimen 214 specifies that the short acting insulin medicament is to be taken up to a predetermined amount of time prior to a meal. In some such embodiments, a respective bolus injection event is deemed insulin regimen nonadherent when the respective bolus injection event occurs this permissible time. In some such embodiments, the predetermined amount of time is thirty minutes or less, twenty minutes or less, or fifteen minutes or less.

Example 2. The following example is made with reference to FIGS. 10A thorough 10D which detail four simulations of blood glucose, insulin injections and insulin sensitivity factor estimation. In this example, 35 days are simulated under the following set of conditions: three meals are ingested each day (breakfast, lunch and dinner), (ii) a simple bolus calculator uses ISF and CIR to calculate bolus and correction dose, (iii) dinner bolus dose is forgotten 40% of the time (to allow correction doses more frequently), (iv) a correction bolus is given four hours after a meal if glucose concentration is high, (v) insulin medicament titration follows a simple 2-0-2 algorithm every second day, (vi) if a hypoglycaemic event occurs during the day, the basal is titrated down by 2U, (vii) during days 16-23 the insulin sensitivity is decreased, to simulate flu or influenza, and (viii) during days 27-29 insulin sensitivity increases, to simulate increased activity/exercise.

Figure 10A:
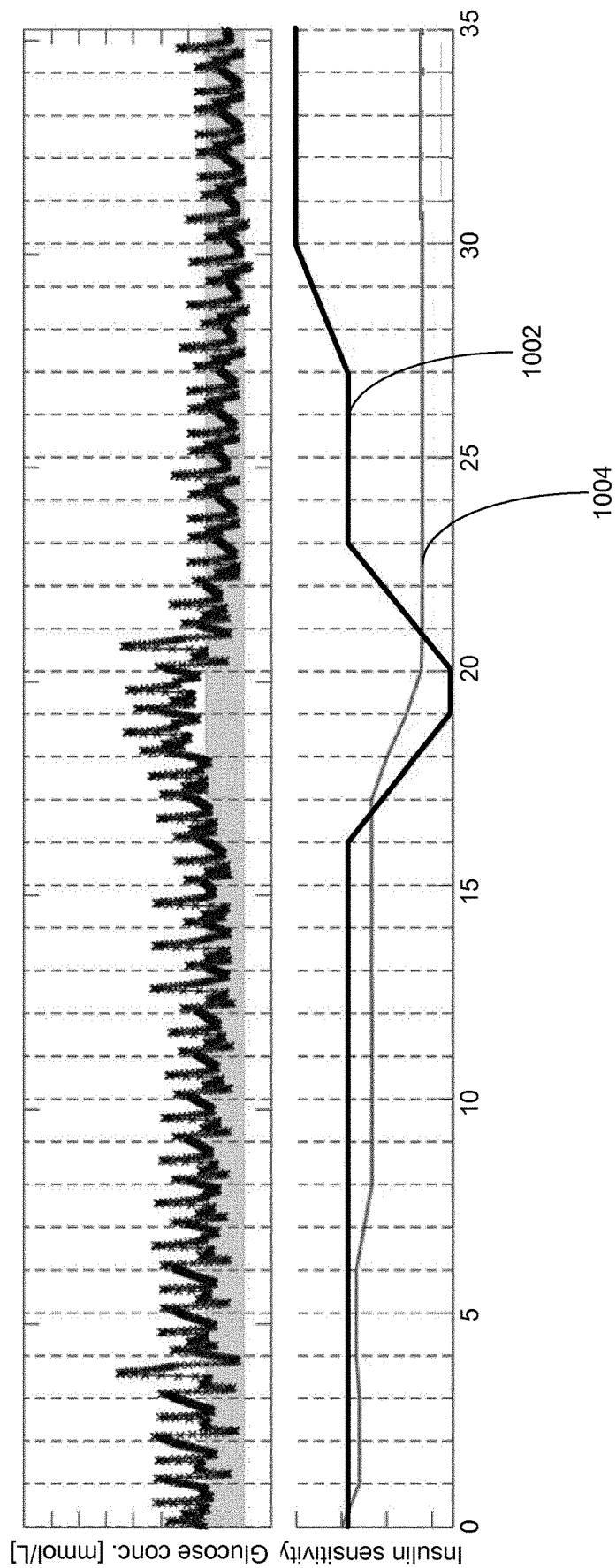
FIG. 10A illustrates an example in which insulin sensitivity factor updates for a subject are made based on correction bolus only.

FIG. 10A illustrates the case of ISF updates based on correction bolus only. Every time a correction bolus is given, the bolus insulin sensitivity factor ($ISF_{bolus,i,t}$) is updated in accordance with block 428 and this updated value is used to make an insulin sensitivity factor curve estimate ($ISF_{bolus,i}$) in accordance with block 432 and to update the bolus insulin sensitivity factor curve $ISF_{bolus}$ in accordance with block 442. The lower panel of FIG. 10A shows the normalized true insulin sensitivity 1002 and a normalized estimate of insulin sensitivity factor ISF 1004, which is proportional to ISF_bolus and ISF_basal. The insulin sensitivity factor ISF is not updated after day 22 since after that, no correction bolus is taken. Periods of hypoglycaemia occur around day 28-31 where insulin sensitivity is increasing, which is compensated for by reducing the basal, while the insulin sensitivity factor estimate does not change and boluses are calculated as before the increased sensitivity.

Figure 10B:
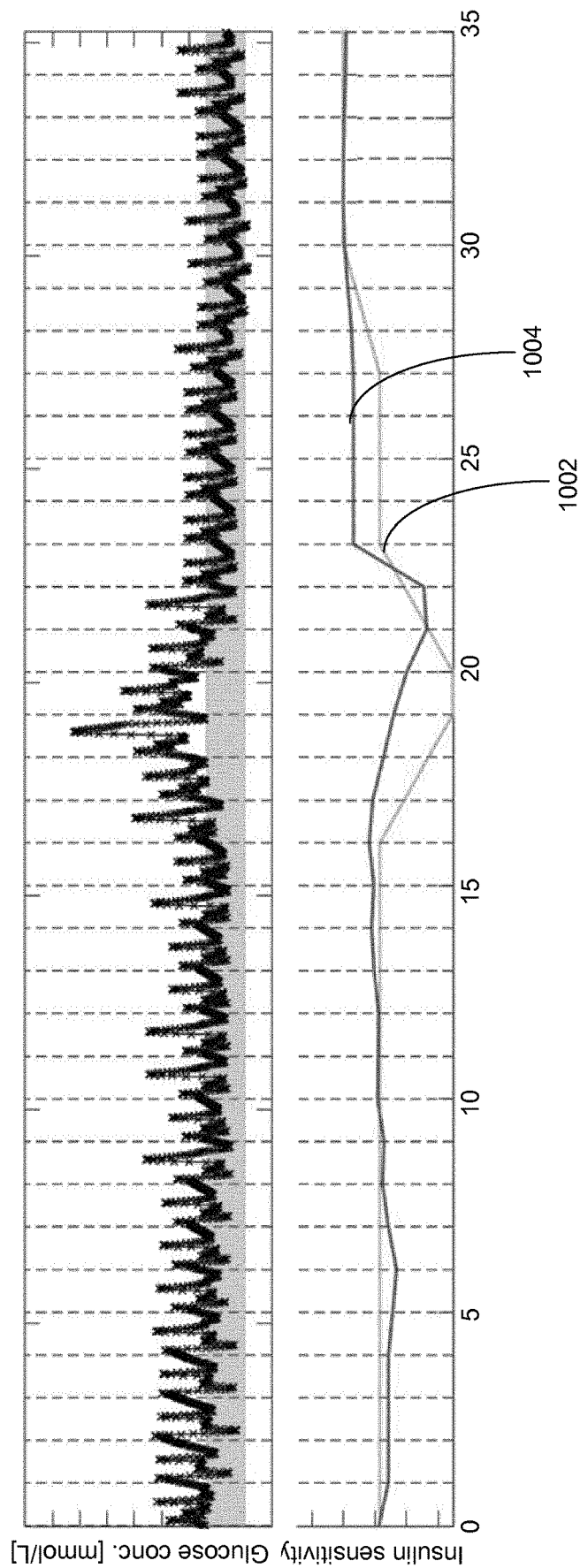
FIG. 10B illustrates an example in which insulin sensitivity factor updates are based on correction bolus and fasting glucose in accordance with the methods set forth in FIG. 4, in accordance with an embodiment of the present disclosure.

FIG. 10B illustrates the case where ISF updates are based on correction bolus and fasting glucose in accordance with the methods set forth in FIG. 4. Every time a correction bolus is given, the bolus insulin sensitivity factor estimate ($ISF_{bolus,i,t}$) is made in accordance with block 428 and this value is used to make an insulin sensitivity factor curve estimate ($ISF_{bolus,i}$) in accordance with block 432 of and to update the bolus insulin sensitivity factor curve in accordance with block 442 of FIG. 4C. Further, every time the patient is in bolus adherence and does not take a correction bolus at night, e.g. a correction bolus that affects the fasting blood glucose, the basal insulin sensitivity factor curve ($ISF_{basal}$) is updated based on the basal injection and fasting glucose, according to blocks 410, 416 and 426 of FIG. 4B. The lower panel of FIG. 10B shows the normalized true insulin sensitivity 1002, and a normalized estimate of the insulin sensitivity factor 1004, which is proportional to $ISF_{bolus}$ and $ISF_{basal}$. From FIG. 10B it is observed that adding a basal ISF estimation improves the performance significantly. The algorithm adjusts to increased insulin sensitivity after the period of illness, as well as the increased sensitivity following increased physical activity. Again, the basal is decreased but bolus calculations are also adjusted to the new physiological state via the new ISF estimate.

Figure 10C:
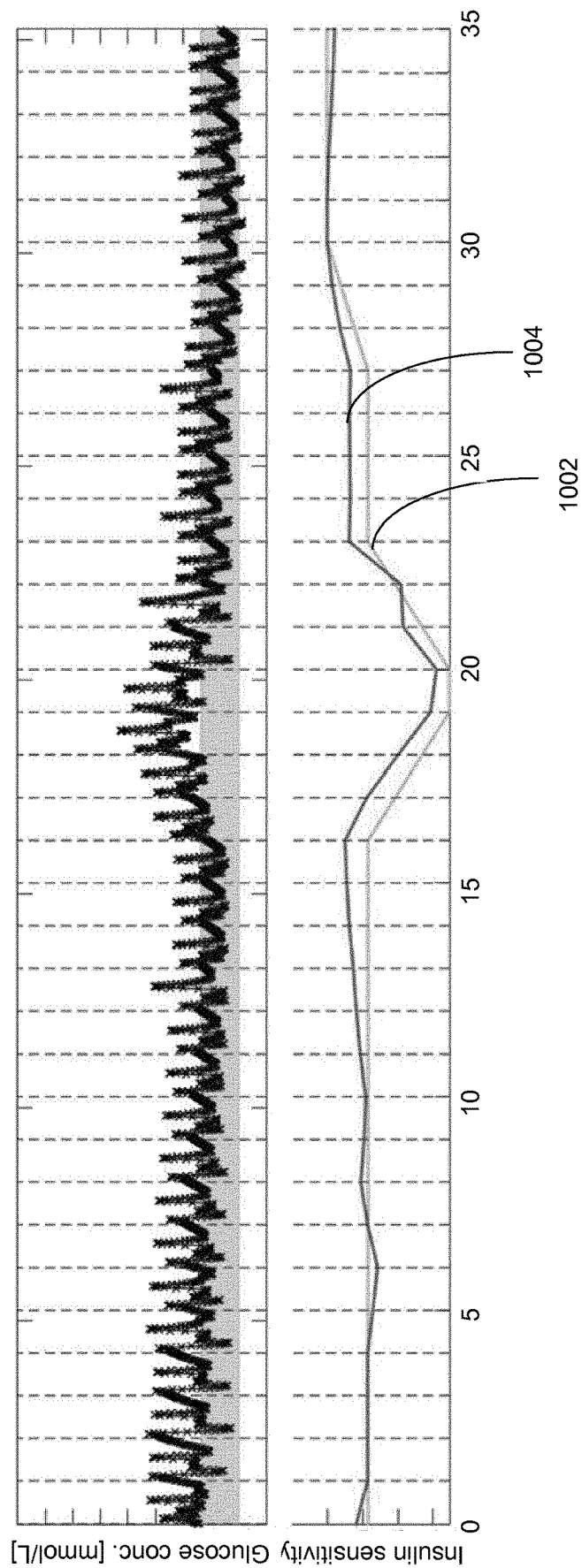
FIG. 10C illustrates an example in which insulin sensitivity factor updates are based on correction bolus and fasting glucose in accordance with the methods set forth in FIG. 4, and in particular information from the wearable devices is used to make new ISF curve estimates weigh higher than past ISF curve estimates when updating the insulin sensitivity factor curve based upon past insulin sensitivity curve estimates in accordance with an embodiment of the present disclosure.

FIG. 10C illustrates the case where the insulin sensitivity factor estimation is similar to that of FIG. 10B. However, here a temperature measuring device indicates that the patient has a fever and that changes in insulin sensitivity factor are expected from day 16-23. An exercise detector notices an increase in activity and announces that after day 27 an increase in insulin sensitivity factor is expected. Information from the wearable devices are used to make new ISF estimates weigh higher than past ISF estimates in accordance with the disclosure of blocks 426 and 444, and the estimation horizon is made shorter. The lower panel of FIG. 10C shows the normalized true insulin sensitivity 1002, and the normalized estimate of the insulin sensitivity factor 1004, which is proportional to $ISF_{bolus}$ and $ISF_{basal}$. Thus, in FIG. 10C, the algorithm had information about expected changes in ISF, and ISF and CIR, respectively. This allows the algorithm to more freely change the estimates based on new observations. It is observed that the estimates follow the curve of the true insulin sensitivity over time more precisely than in FIGS. 10A and 10B.

Figure 10D:
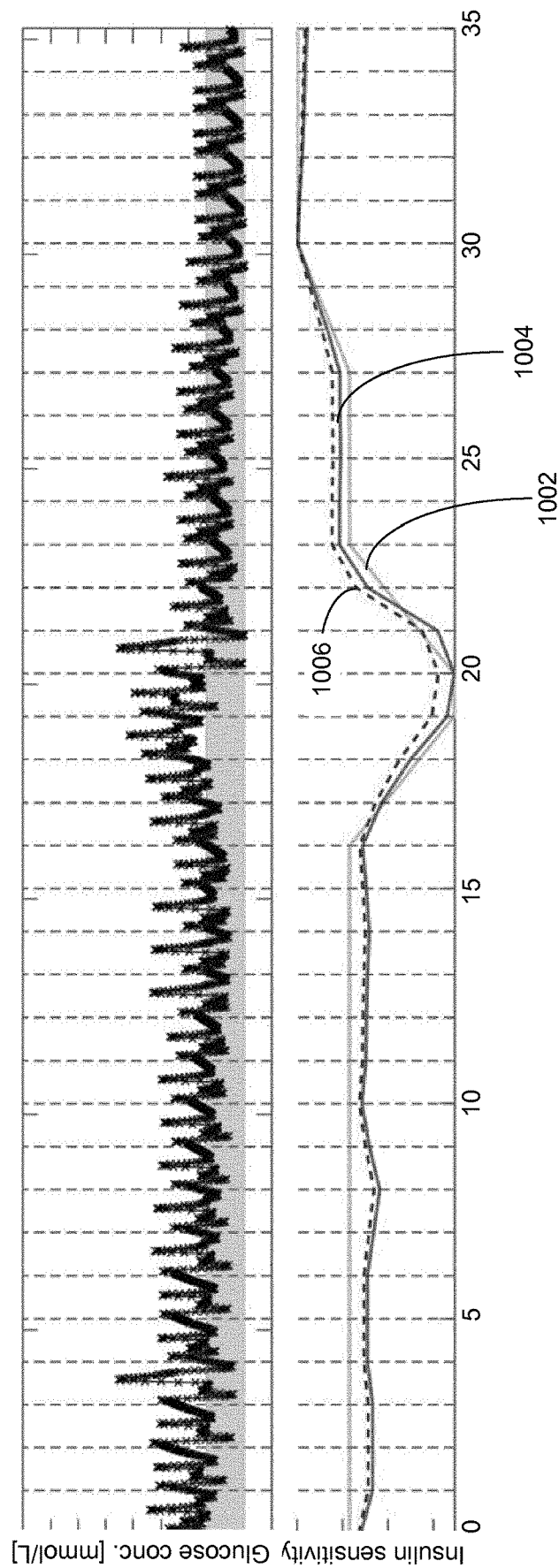
FIG. 10D illustrates an example in which insulin sensitivity factor updates are as in FIG. 10C except that the carb-to-insulin ratio CIR is updated proportionally to changes in ISF in accordance with an embodiment of the present disclosure.

FIG. 10D illustrates the case where the insulin sensitivity factor estimation is similar to that of FIG. 10C. However, the carb-to-insulin ratio CIR is changed proportionally to changes in ISF. When the algorithm adjusted CIR and ISF, the hypoglycaemic events during transition in insulin sensitivity around day 30 are minimized compared to the cases illustrated in FIGS. 10A, 10B, and 10C. The lower panel of FIG. 10D shows the normalized true insulin sensitivity 1002, the normalized estimate of the insulin sensitivity factor 1004, and the estimated carb-to-insulin ratio 1006. Here, the carb-to-insulin ratio is updated proportionally to the ISF estimate as follows:

$$CIR_i = \left(\frac{ISF_{i,t} - ISF_{i-p,t}}{ISF_{i-p,t}} + 1\right)CIR_{i-p}.$$

LIST OF EMBODIMENTS

1. A device (250) for estimating parameters in an insulin medicament regimen (206) for a subject that includes both a short acting insulin medicament regimen (214) and a long acting insulin medicament regimen (208), and wherein the device comprises one or more processors and a memory, the memory storing instructions that, when executed by the one or more processors, perform a method of:
   A) obtaining:
      A.1) a first data set (220), the first data set comprising a plurality of glucose measurements of the subject taken over a first period of time and, for each respective glucose measurement (222) in the plurality of glucose measurements, a timestamp (224) representing when the respective measurement was made;
      A.2) a second data set from one or more insulin pens used by the subject to apply the insulin medicament dosage regimen, the second data set comprises a plurality of insulin medicament records, each insulin medicament record in the plurality of medicament records comprises: (i) a respective insulin medicament injection event including an amount of insulin medicament injected into the subject using a respective insulin pen in the one or more insulin pens (ii) a corresponding electronic timestamp that is automatically generated by the respective insulin pen upon occurrence of the respective insulin medicament injection event, and (iii) a type of insulin medicament, wherein the type of insulin medicament is a short acting insulin medicament or a long acting insulin medicament;
   B) determining one or more insulin sensitivity change estimates by:
      B.1) making an estimate of a basal insulin sensitivity change between a basal insulin sensitivity estimate ($ISF_{basal,i,t}$) (230) for the subject related to the occurrence of a first basal insulin related event undertaken by the subject within the first period of time, when the first basal insulin related event is deemed qualified, and a basal insulin sensitivity estimate (ISF$_{basal,i-p,t}$) of the subject related to the occurrence of a qualified basal insulin related event occurring before the first basal insulin related event, wherein the occurrence of the basal insulin related events are identified in the first data set, the estimating using:
  (i) the basal insulin sensitivity estimate (ISF$_{basal,i-p,t}$) of the subject related to the occurrence of the qualified basal insulin related event occurring before the first basal insulin related event (ii) glucose measurements from the first data set contemporaneous with the occurrence of the first qualified basal insulin related event, (iii) glucose measurements from the first data set contemporaneous with the occurrence of the qualified basal insulin related event occurring before the first qualified basal insulin related event, (iv) an insulin medicament injection event from the second data set corresponding to the first qualified basal insulin related event, wherein the injection has been applied according to the long acting insulin medicament regimen (208), and (v) an insulin medicament injection event from the second data set corresponding to the qualified basal insulin related event occurring before the first qualified basal insulin related event, wherein the injection has been applied according to the long acting insulin medicament regimen (208); and/or
 B.2) making an estimate of a bolus insulin sensitivity change between a bolus insulin sensitivity estimate (ISF$_{bolus,i,t}$) (232) for the subject relating to the occurrence of a correction bolus with a short acting insulin medicament within the first period of time and a bolus insulin sensitivity estimate (ISF$_{bolus,i-p,t}$) of the subject related to the occurrence of a prior correction bolus with the short acting insulin medicament, wherein the occurrence of the correction bolus and the occurrence of the prior correction bolus are identified in the first data set, the estimating using: (i) glucose measurements from the first data set contemporaneous with the occurrence of the correction bolus with a short acting medicament, (ii) the bolus insulin sensitivity estimate (ISF$_{bolus,i-p,t}$) of the subject related to the occurrence of a prior correction bolus with the short acting insulin medicament and (iii) an insulin medicament injection event from the second data set corresponding to the occurrence of the correction bolus and applied according to the short acting insulin medicament regimen (214); and
 C) estimating the bolus insulin sensitivity estimate (ISF$_{bolus,i,t}$) as a function of the estimated basal insulin sensitivity change, in response to making an estimate of the basal insulin sensitivity change in B.1); and/or
 D) estimating the basal insulin sensitivity estimate (ISF$_{basal,i,t}$) as a function of the estimated bolus insulin sensitivity change, in response to making an estimate of the bolus insulin sensitivity change in B.2), and
wherein the insulin sensitivity estimates are parameters in the insulin medicament regimen.

2. The device of embodiment 1, wherein the estimated basal insulin sensitivity change is a function of the estimated basal insulin sensitivity estimate (ISF$_{basal,i,t}$) for the subject upon occurrence of the first basal insulin related event and the basal insulin sensitivity factor (ISF$_{basal,i-p,t}$) of the subject during the qualified basal insulin related event occurring before the first bolus insulin relevant event.

3. The device of any of embodiments 1-2, wherein the estimated bolus insulin sensitivity change is a function of the estimated bolus insulin sensitivity estimate (ISF$_{bolus,i,t}$) for the subject upon occurrence of the correction bolus with a short acting insulin medicament and the bolus insulin sensitivity factor (ISF$_{bolus,i-p,t}$) of the subject estimated based upon occurrence of a prior correction bolus with the short acting insulin medicament.

4. The device of any of embodiments 1-3, the method further comprising:
  E) estimating a basal insulin sensitivity factor curve (ISF$_{basal,i}$) (234) as a function of the estimated basal insulin change, in response to estimating the basal insulin sensitivity change in B.1) and/or in response to estimating the basal insulin sensitivity estimate in D).

5. The device of embodiment 4, wherein the estimating the basal insulin sensitivity factor curve (ISF$_{basal,i}$) in E) comprises computing:

$$ISF_{basal,i} = \left( \frac{ISF_{basal,i,t} - ISF_{basal,i-p,t}}{ISF_{basal,i-p,t}} + 1 \right) ISF_{basal,i-p},$$

wherein ISF$_{basal,i-p}$ represents a prior basal sensitivity factor curve estimate.

6. The device of any of embodiments 1-5, the method further comprising:
  F) estimating a bolus insulin sensitivity factor curve (ISF$_{bolus,i}$) (236) as a function of (i) the estimated bolus insulin sensitivity change, in response to estimating the bolus insulin sensitivity change in B2) and/or in response to estimating the bolus insulin sensitivity in C).

7. The device of embodiments 6, wherein the estimating the bolus sensitivity factor curve (ISF$_{bolus,i}$) in F) comprises computing:

$$ISF_{bolus,i} = \left( \frac{ISF_{bolus,i,t} - ISF_{bolus,i-p,t}}{ISF_{bolus,i-p,t}} + 1 \right) ISF_{bolus,i-p},$$

wherein ISF$_{bolus,i-p}$ represents a prior bolus sensitivity factor curve estimate.

8. The device of any of embodiments 4-7, the method further comprising:
  G) updating
    (i) the bolus insulin sensitivity curve (ISF$_{bolus}$) as a function of the estimated bolus insulin sensitivity factor curve (ISF$_{bolus,i}$) of F) and prior estimated bolus insulin sensitivity factor curves for the subject, and
    (ii) updating the basal insulin sensitivity curve (ISF$_{basal}$) as a function of the estimated basal insulin sensitivity factor curve (ISF$_{basal,i,t}$) of E) and prior estimated basal insulin sensitivity factor curves for the subject; and
  H) providing a recommended dose of the short acting insulin medicament to achieve a target fasting glucose level in the subject by using glucose measurements from a portion of the plurality of glucose measurements and the updated bolus insulin sensitivity curve (ISF$_{bolus}$) or the updated basal insulin sensitivity curve (ISF$_{basal}$).

9. The device of any one of embodiments 1-8, wherein estimating the basal insulin sensitivity change for the subject in B.1) is computed as:

$$\left(\frac{ISF_{basal,i}}{ISF_{basal,i-p}}\right) = \left(\frac{FBG_{expected} - \widehat{FBG}_i}{\widehat{FBG}_i} + 1\right),$$

wherein $FBG_{expected}$ is the expected blood glucose level ($FBG_{expected}$) in a period of time during the first qualified basal insulin related event based on (i) the basal insulin sensitivity estimate ($ISF_{basal,i-p,t}$) of the subject related to the occurrence of the qualified basal insulin related event occurring before the first basal insulin related event (ii) the glucose measurements from the first data set contemporaneous with the occurrence of the qualified basal insulin related event occurring before the first qualified basal insulin related event, (iii) the insulin medicament injection event from the second data set corresponding to the first qualified basal insulin related event, and (iv) the insulin medicament injection event from the second data set corresponding to the qualified basal insulin related event occurring before the first qualified basal insulin related event, and wherein $\widehat{FBG}_i$ is the glucose level ($\widehat{FBG}_i$) obtained from the glucose measurements from the first data set contemporaneous with the occurrence of the first qualified basal insulin related event.

10. The device of any one of embodiments 1-8, wherein estimating the basal insulin sensitivity change for the subject in B.1) is computed as:

$$\left(\frac{ISF_{basal,i,t}}{ISF_{basal,i-p,t}}\right) = \left(\frac{\widehat{FBG}_i - \widehat{FBG}_{i-p}}{FBG_{expected} - \widehat{FBG}_{i-p}}\right),$$

wherein $\widehat{FBG}_i$ is the glucose level ($\widehat{FBG}_i$) obtained from the glucose measurements from the first data set contemporaneous with the occurrence of the first qualified basal insulin related event, wherein $FBG_{expected}$ is the expected blood glucose level ($FBG_{expected}$) during the first basal insulin related event based on (i) the basal insulin sensitivity estimate ($ISF_{basal,i-p,t}$) of the subject related to the occurrence of the qualified basal insulin related event occurring before the first basal insulin related event (ii) the glucose measurements from the first data set contemporaneous with the occurrence of the qualified basal insulin related event occurring before the first qualified basal insulin related event, (iii) the insulin medicament injection event from the second data set corresponding to the first qualified basal insulin related event, and (iv) the insulin medicament injection event from the second data set corresponding to the qualified basal insulin related event occurring before the first qualified basal insulin related event, and wherein $\widehat{FBG}_{i-p}$ is the glucose level ($\widehat{FBG}_{i-p}$) obtained from the glucose measurements from the first data set contemporaneous with the occurrence of the qualified basal insulin related event occurring before the first qualified basal insulin related event, and wherein $FBG_{expected}$ is different from $\widehat{FBG}_{i-p}$.

11. The device of any of embodiments 9-10, wherein the expected blood glucose level ($FBG_{expected}$) is computed as:

$$FBG_{expected} = \widehat{FBG}_{basal,i-p} - ISF_{basal,i-p,t}(U_{basal,i} - U_{basal,i-p}),$$

wherein $U_{basal,i}$ is the amount of insulin medicament ($U_{basal,i}$) corresponding to the insulin medicament injection event from the second data set corresponding to the first qualified basal insulin related event, $U_{basal,i-1}$ is the amount of insulin ($U_{basal,i-p}$) corresponding to the insulin medicament injection event from the second data set corresponding to the qualified basal insulin related event occurring before the first qualified basal insulin related event.

12. The device of any one of embodiments 1-11, wherein the first basal insulin related event is deemed qualified when (i) the subject has taken no correction bolus of the short acting insulin medicament in the twelve hours prior to the first basal insulin related event and (ii) the subject has taken a meal bolus of the short acting insulin medicament with each hypoglycaemic event free meal in the fourteen hours prior to the first fasting event, wherein the occurrence of a correction bolus, a first basal insulin related event, a hypoglycaemic event free meal are identified in the first data set 13. The device of embodiment 12, wherein the occurrence of a correction bolus is further identified in the second data set.

14. The device of any one of embodiments 1-8, wherein the estimating the bolus insulin sensitivity change in B.2) is computed as:

$$\left(\frac{ISF_{bolus,i,t}}{ISF_{bolus,i-p,t}}\right) = \left(\frac{BG_{expected} - \widehat{BG}_{bolus,corr,i}}{\widehat{BG}_{bolus,corr,i}} + 1\right),$$

wherein $BG_{expected}$ is the expected blood glucose level ($BG_{expected}$) based on (i) the glucose level ($\widehat{BG}_{bolus,hyp,i}$) of the subject after a meal event, wherein $\widehat{BG}_{bolus,hyp,i}$ is obtained from the portion of the glucose measurements obtained from the first data set that are contemporaneous with a period of time during a hyperglycaemic event after a meal event, and whereby the portion of the glucose measurements is a subset of the measurements that are contemporaneous with the occurrence of the correction bolus with a short acting medicament, (ii) the bolus insulin sensitivity estimate ($ISF_{bolus,i-p,t}$) of the subject related to the occurrence of the prior correction bolus with the short acting insulin medicament and (iii) an insulin medicament injection event from the second data set corresponding to the occurrence of the correction bolus, and wherein $\widehat{BG}_{bolus,corr,i}$ is the glucose level ($\widehat{BG}_{bolus,corr,i}$) of the subject after the occurrence of the correction bolus, wherein $\widehat{BG}_{corr,i}$ is obtained from the portion of the glucose measurements of the first data set that are contemporaneous with a period of time after the occurrence of the correction bolus, and whereby the portion of the glucose measurements is a subset of the measurements that are contemporaneous with the occurrence of the correction bolus with a short acting medicament.

15. The device of any one of embodiments 1-8, wherein the estimating the bolus insulin sensitivity change in B.2) is computed as:

$$\left(\frac{ISF_{bolus,i,t}}{ISF_{bolus,i-p,t}}\right) = \left(\frac{\widehat{BG}_{bolus,hyp,i} - \widehat{BG}_{bolus,corr,i}}{\widehat{BG}_{bolus,corr,i} - BG_{expected}}\right),$$

wherein $\widehat{BG}_{bolus,hyp,i}$ is the glucose level ($\widehat{BG}_{bolus,hyp,i}$) of the subject after a meal event, wherein $\widehat{BG}_{bolus,hyp,i}$ is obtained from the portion of the glucose measurements obtained from the first data set that are contemporaneous with a period of time during a hyperglycaemic event after a meal event, and whereby the portion of the glucose measurements is a subset of the measurements that are contemporaneous with the occurrence of the correction bolus with a short acting medicament, wherein $\widehat{BG}_{bolus,corr,i}$ is the glucose level ($\widehat{BG}_{corr,i}$) of the subject after occurrence of the correction bolus, wherein $\widehat{BG}_{bolus,corr,i}$ is the glucose level ($\widehat{BG}_{bolus,corr,i}$) of the subject after the occurrence of the correction bolus, wherein $\widehat{BG}_{bolus,corr,i}$ is obtained from the portion of the glucose measurements of the first data set that are contemporaneous with a period of time after the occurrence of the correction bolus, and whereby the portion of the glucose measurements is a subset of the measurements that are contemporaneous with the occurrence of the correction bolus with a short acting medicament, and wherein $BG_{expected}$ is the expected blood glucose level ($BG_{expected}$) based on (i) the glucose level $\widehat{BG}_{bolus,hyp,i}$ of the subject after a meal event, wherein $\widehat{BG}_{bolus,hyp,i}$ is obtained from the portion of the glucose measurements obtained from the first data set that are contemporaneous with a period of time during a hyperglycaemic event after a meal event, and whereby the portion of the glucose measurements is a subset of the measurements that are contemporaneous with the occurrence of the correction bolus with a short acting medicament, (ii) the bolus insulin sensitivity estimate ($ISF_{bolus,i-p,t}$) of the subject related to the occurrence of the prior correction bolus with the short acting insulin medicament and (iii) an insulin medicament injection event from the second data set corresponding to the occurrence of the correction bolus.

15. The device of any of embodiments 14-15, wherein the expected blood glucose level ($BG_{expected}$) is computed as:

$$BG_{expected} = \widehat{BG}_{bolus1,hyp,i} - ISF_{bolus,i-p,t} U_{bolus,i}.$$

16. The device of any of embodiments 1-15, wherein the estimating the bolus insulin sensitivity curve ($ISF_{bolus,i}$) as a function of the estimated basal insulin sensitivity change, in response to estimating the basal insulin sensitivity change in B.1) comprises computing:

$$ISF_{bolus,i} = \left( \frac{ISF_{basal,i,t} - ISF_{basal,i-p,t}}{ISF_{basal,i-p,t}} + 1 \right) ISF_{bolus,i-p},$$

wherein $ISF_{bolus,i-p}$ represents a prior bolus sensitivity factor curve estimate.

17. The device of any of embodiments 1-16, wherein the estimating the basal insulin sensitivity curve ($ISF_{basal,i}$) as a function of the estimated bolus insulin sensitivity change, in response to estimating the bolus insulin sensitivity change in B2) comprises computing:

$$ISF_{basal,i} = \left( \frac{ISF_{bolus,i,t} - ISF_{bolus,i-p,t}}{ISF_{bolus,i-p,t}} + 1 \right) ISF_{basal,i-p},$$

wherein $ISF_{basal,i-p}$ represents a prior basal sensitivity factor curve estimate.

18. The device of any of embodiments 6-7 and 16 wherein the updating the bolus insulin sensitivity factor curve comprises computing:

$$ISF_{bolus} = \sum_{n=i-q}^{i} w_n ISF_{bolus,n},$$

wherein,
q is a predetermined number of historical updates to the bolus insulin sensitivity curve ($ISF_{bolus}$),
w is a linear or nonlinear vector of normalised weights,
n is an integer index into the historical updates to the bolus insulin sensitivity curve ($ISF_{bolus}$) and vector w, and
$ISF_{bolus,n}$ is an $n^{th}$ past bolus insulin sensitivity curve ($ISF_{bolus}$) curve.

19. The device of any of embodiments 4-5 and 17 wherein the updating the basal insulin sensitivity factor curve comprises computing:

$$ISF_{basal} = \sum_{n=i-q}^{i} w_n ISF_{basal,n}$$

wherein,
q is a predetermined number of historical updates to the basal insulin sensitivity curve ($ISF_{basal}$),
w is a linear or nonlinear vector of normalised weights,
n is an integer index into the historical updates to the basal insulin sensitivity curve ($ISF_{basal}$) and vector w, and
$ISF_{basal,n}$ is an $n^{th}$ past basal insulin sensitivity curve ($ISF_{basal}$).

20. The device of any one of embodiments 1-17, wherein the method further comprises:
obtaining a third data set (238), the third data set comprising a plurality of physiological measurements of the subject taken over the first period of time and, for each respective physiological measurement (240) in the plurality of physiological measurements, a physiological measurement timestamp (242) representing when the respective physiological measurement was made; and wherein
a value of p is determined by the plurality of physiological measurements.

21. The device of embodiment 20, wherein each physiological measurement is a measurement of body temperature of the subject and wherein p is reduced during periods when the subject has an elevated temperature.

22. The device of embodiment 20, wherein each physiological measurement is a measurement of activity of the subject and wherein p is reduced during periods when the subject is incurring elevated activity.

23. A method for estimating parameters in an insulin medicament dosage regimen for a subject that includes both a short acting insulin medicament regimen and a long acting insulin medicament regimen, the method comprising:
A) obtaining:
A.1) a first data set (220), the first data set comprising a plurality of glucose measurements of the subject taken over a first period of time and, for each respective glucose measurement (222) in the plurality of glucose measurements, a timestamp (224) representing when the respective measurement was made;
A.2) a second data set from one or more insulin pens used by the subject to apply the insulin medicament dosage regimen, the second data set comprises a plurality of insulin medicament records, each insulin medicament record in the plurality of medicament records comprises: (i) a respective insulin medicament injection event including an amount of insulin medicament injected into the subject using a respective insulin pen in the one or more insulin pens (ii) a corresponding electronic timestamp that is automatically generated by the respective insulin pen upon occurrence of the respective insulin medicament injection event, and (iii) a type of insulin medicament, wherein the type of insulin medicament is a short acting insulin medicament or a long acting insulin medicament;

B) determining one or more insulin sensitivity change estimates by:

B.1) making an estimate of a basal insulin sensitivity change between a basal insulin sensitivity estimate ($ISF_{basal,i,t}$) (230) for the subject related to the occurrence of a first basal insulin related event undertaken by the subject within the first period of time, when the first basal insulin related event is deemed qualified, and a basal insulin sensitivity estimate ($ISF_{basal,i-p,t}$) of the subject related to the occurrence of a qualified basal insulin related event occurring before the first basal insulin related event, wherein the occurrence of the basal insulin related events are identified in the first data set, the estimating using: (i) the basal insulin sensitivity estimate ($ISF_{basal,i-p,t}$) of the subject related to the occurrence of the qualified basal insulin related event occurring before the first basal insulin related event (ii) glucose measurements from the first data set contemporaneous with the occurrence of the first qualified basal insulin related event, (iii) glucose measurements from the first data set contemporaneous with the occurrence of the qualified basal insulin related event occurring before the first qualified basal insulin related event, (iv) an insulin medicament injection event from the second data set corresponding to the first qualified basal insulin related event, wherein the injection has been applied according to the long acting insulin medicament regimen (208), and (v) an insulin medicament injection event from the second data set corresponding to the qualified basal insulin related event occurring before the first qualified basal insulin related event, wherein the injection has been applied according to the long acting insulin medicament regimen (208); and/or B.2) making an estimate of a bolus insulin sensitivity change between a bolus insulin sensitivity estimate ($ISF_{bolus,i,t}$) (232) for the subject relating to the occurrence of a correction bolus with a short acting insulin medicament within the first period of time and a bolus insulin sensitivity estimate ($ISF_{bolus,i-p,t}$) of the subject related to the occurrence of a prior correction bolus with the short acting insulin medicament, wherein the occurrence of the correction bolus and the occurrence of the prior correction bolus are identified in the first data set, the estimating using: (i) glucose measurements from the first data set contemporaneous with the occurrence of the correction bolus with a short acting medicament, (ii) the bolus insulin sensitivity estimate ($ISF_{bolus,i-p,t}$) of the subject related to the occurrence of a prior correction bolus with the short acting insulin medicament and (iii) an insulin medicament injection event from the second data set corresponding to the occurrence of the correction bolus and applied according to the short acting insulin medicament regimen (214); and C) estimating the bolus insulin sensitivity estimate ($ISF_{bolus,i,t}$) as a function of the estimated basal insulin sensitivity change, in response to making an estimate of the basal insulin sensitivity change in B.1); and/or D) estimating the basal insulin sensitivity estimate ($ISF_{basal,i,t}$) as a function of the estimated bolus insulin sensitivity change, in response to making an estimate of the bolus insulin sensitivity change in B.2), and wherein the insulin sensitivity estimates are parameters in the insulin medicament regimen.

24. A computer program is provided comprising instructions that, when executed by one or more processors, perform the method according to embodiment 23.

25. A computer-readable data carrier having stored thereon the computer program according to embodiment 24.

REFERENCES CITED AND ALTERNATIVE EMBODIMENTS

All references cited herein are incorporated herein by reference in their entirety and for all purposes to the same extent as if each individual publication or patent or patent application was specifically and individually indicated to be incorporated by reference in its entirety for all purposes.

The present invention can be implemented as a computer program product that comprises a computer program mechanism embedded in a nontransitory computer readable storage medium. For instance, the computer program product could contain the program modules shown in any combination of FIG. 1, 2, or 3 and/or described in FIG. 4. These program modules can be stored on a CD-ROM, DVD, magnetic disk storage product, or any other non-transitory computer readable data or program storage product.

Many modifications and variations of this invention can be made without departing from its spirit and scope, as will be apparent to those skilled in the art. The specific embodiments described herein are offered by way of example only. The embodiments were chosen and described in order to best explain the principles of the invention and its practical applications, to thereby enable others skilled in the art to best utilize the invention and various embodiments with various modifications as are suited to the particular use contemplated. The invention is to be limited only by the terms of the appended claims, along with the full scope of equivalents to which such claims are entitled.

The invention claimed is:

1. A device for estimating parameters in an insulin medicament regimen for a subject that includes both a short acting insulin medicament regimen and a long acting insulin medicament regimen, and wherein the device comprises one or more processors and a memory, the memory storing instructions that, when executed by the one or more processors, perform a method of:

A) obtaining:

A.1) a first data set, the first data set comprising a plurality of glucose measurements of the subject taken over a first period of time received autonomously originating from one or more glucose sensors attached to a subject on an ongoing basis and, for each respective glucose measurement in the plurality of glucose measurements, a timestamp representing when the respective measurement was made;

A.2) a second data set from one or more insulin pens used by the subject to apply the insulin medicament dosage regimen, the second data set comprises a plurality of insulin medicament records, each insulin medicament record in the plurality of medicament records comprises: (i) a respective insulin medicament injection event including an amount of insulin medicament injected into the subject using a respective insulin pen in the one or more insulin pens (ii)

a corresponding electronic timestamp that is automatically generated by the respective insulin pen upon occurrence of the respective insulin medicament injection event, and (iii) a type of insulin medicament, wherein the type of insulin medicament is a short acting insulin medicament or a long acting insulin medicament;

B) determining one or more insulin sensitivity change estimates by:

B. 1) making an estimate of a basal insulin sensitivity change between a basal insulin sensitivity estimate ($ISF_{basil,i,t}$) for the subject related to the occurrence of a first basal insulin related event undertaken by the subject within the first period of time, when the first basal insulin related event is deemed qualified, and a basal insulin sensitivity estimate ($ISF_{basil,i-p,t}$) of the subject related to the occurrence of a qualified basal insulin related event occurring before the first basal insulin related event, wherein the occurrence of the basal insulin related events are identified in the first data set, the estimating using:

(i) the basal insulin sensitivity estimate ($ISF_{basil,i-p,t}$) of the subject related to the occurrence of the qualified basal insulin related event occurring before the first basal insulin related events (ii) glucose measurements from the first data set contemporaneous with the occurrence of the first qualified basal insulin related event, (iii) glucose measurements from the first data set contemporaneous with the occurrence of the qualified basal insulin related event occurring before the first qualified basal insulin related event, (iv) an insulin medicament injection event from the second data set corresponding to the first qualified basal insulin related event, wherein the injection has been applied according to the long acting insulin medicament regimen, and (v) an insulin medicament injection event from the second data set corresponding to the qualified basal insulin related event occurring before the first qualified basal insulin related event, wherein the injection has been applied according to the long acting insulin medicament regimen; and/or B.2) making an estimate of a bolus insulin sensitivity change between a bolus insulin sensitivity estimate ($ISF_{bolus,i,t}$) for the subject relating to the occurrence of a correction bolus with a short acting insulin medicament within the first period of time and a bolus insulin sensitivity estimate ($ISF_{bolus,i-p,t}$) of the subject related to the occurrence of a prior correction bolus with the short acting insulin medicament, wherein the occurrence of the correction bolus and the occurrence of the prior correction bolus are identified in the first data set, the estimating using:

(i) glucose measurements from the first data set contemporaneous with the occurrence of the correction bolus with a short acting medicament, (ii) the bolus insulin sensitivity estimate ($ISF_{bolus,i-p,t}$) of the subject related to the occurrence of a prior correction bolus with the short acting insulin medicament, and (iii) an insulin medicament injection event from the second data set corresponding to the occurrence of the correction bolus and applied according to the short acting insulin medicament regimen; and C) estimating the bolus insulin sensitivity estimate ($ISF_{bolus,i,t}$) as a function of the estimated basal insulin sensitivity change, in response to making an estimate of the basal insulin sensitivity change in B.1); and/or D) estimating the basal insulin sensitivity estimate ($ISF_{basil,i,t}$) as a function of the estimated bolus insulin sensitivity change, in response to making an estimate of the bolus insulin sensitivity change in B.2), E) estimating a basal insulin sensitivity factor curve ($ISF_{basal}$) as a function of the estimated basal insulin change, in response to estimating the basal insulin sensitivity change in B.1) and/or in response to estimating the basal insulin sensitivity estimate in D);

F) estimating a bolus insulin sensitivity factor curve ($ISF_{bolus,i}$) as a function of (i) the estimated bolus insulin sensitivity change, in response to estimating the bolus insulin sensitivity change in B2) and/or in response to estimating the bolus insulin sensitivity in C);

G) updating: (i) the bolus insulin sensitivity curve ($ISF_{bolus}$) as a function of the estimated bolus insulin sensitivity factor curve ($ISF_{bolus,i}$) of F) and prior estimated bolus insulin sensitivity factor curves for the subject, and (ii) updating the basal insulin sensitivity curve ($ISF_{basal}$) as a function of the estimated basal insulin sensitivity factor curve ($ISF_{basal,i}$) of E) and prior estimated basal insulin sensitivity factor curves for the subject; and H) providing a recommended dose of the short acting insulin medicament to achieve a target fasting glucose level in the subject by using glucose measurements from a portion of the plurality of glucose measurements and the updated bolus insulin sensitivity curve ($ISF_{bolus}$) or the updated basal insulin sensitivity curve ($ISF_{basal}$), wherein the insulin sensitivity estimates are parameters in the insulin medicament regimen.

2. The device of claim 1, wherein the estimated basal insulin sensitivity change is a function of the estimated basal insulin sensitivity estimate ($ISF_{basal,i,t}$) for the subject upon occurrence of the first basal insulin related event and the basal insulin sensitivity factor ($ISF_{basal,i-p,t}$) of the subject during the qualified basal insulin related event occurring before the first bolus insulin relevant event.

3. The device of claim 1, wherein the estimated bolus insulin sensitivity change is a function of the estimated bolus insulin sensitivity estimate ($ISF_{bolus,i,t}$) for the subject upon occurrence of the correction bolus with a short acting insulin medicament and the bolus insulin sensitivity factor ($ISF_{bolus,i-p,t}$) of the subject estimated based upon occurrence of a prior correction bolus with the short acting insulin medicament.

4. The device of claim 1, wherein the estimating the basal insulin sensitivity factor curve ($ISF_{basal,i}$) in E) comprises computing:

$$ISF_{basal,i} = \left( \frac{ISF_{basal,i,t} - ISF_{basal,i-p,t}}{ISF_{basal,i-p,t}} + 1 \right) ISF_{basal,i-p},$$

wherein $ISF_{basal,i-p}$ represents a prior basal sensitivity factor curve estimate.

5. The device of claim 1, wherein the estimating the bolus sensitivity factor curve ($ISF_{bolus,i}$) in F) comprises computing:

$$ISF_{bolus,i} = \left( \frac{ISF_{bolus,i,t} - ISF_{bolus,i-p,t}}{ISF_{bolus,i-p,t}} + 1 \right) ISF_{bolus,i-p},$$

wherein $ISF_{bolus,i-p}$ represents a prior bolus sensitivity factor curve estimate.

6. The device of claim 1, wherein estimating the basal insulin sensitivity change for the subject in B.1) is computed as:

$$\left( \frac{ISF_{basal,i}}{ISF_{basal,i-p}} \right) = \left( \frac{FBG_{expected} - \widehat{FBG}_i}{\widehat{FBG}_i} + 1 \right),$$

wherein $FBG_{expected}$ is the expected blood glucose level ($FBG_{expected}$) in a period of time during the first qualified basal insulin related event based on:
  (i) the basal insulin sensitivity estimate ($ISF_{basal,i-p,t}$) of the subject related to the occurrence of the qualified basal insulin related event occurring before the first basal insulin related event,
  (ii) the glucose measurements from the first data set contemporaneous with the occurrence of the qualified basal insulin related event occurring before the first qualified basal insulin related event,
  (iii) the insulin medicament injection event from the second data set corresponding to the first qualified basal insulin related event, and
  (iv) the insulin medicament injection event from the second data set corresponding to the qualified basal insulin related event occurring before the first qualified basal insulin related event, and wherein $\widehat{FBG}_i$ is the glucose level ($\widehat{FBG}_i$) obtained from the glucose measurements from the first data set contemporaneous with the occurrence of the first qualified basal insulin related event.

7. The device of claim 6, wherein the expected blood glucose level ($FBG_{expected}$) is computed as:

$$FBG_{expected} = \widehat{FBG}_{basal,i-p} - ISF_{basal,i-p,t}(U_{basal,i} - U_{basal,i-p}),$$

wherein $\widehat{FBG}_{basal,i-p}$ is the glucose level ($\widehat{FBG}_{basal,i-p}$) based on the glucose measurements from the first data set contemporaneous with the occurrence of the qualified basal insulin related event occurring before the first qualified basal insulin related event, wherein $U_{basal,i}$ is the amount of insulin medicament ($U_{basal,i}$) corresponding to the insulin medicament injection event from the second data set corresponding to the first qualified basal insulin related event, $U_{basal,i-1}$ is the amount of insulin ($U_{basal,i-p}$) corresponding to the insulin medicament injection event from the second data set corresponding to the qualified basal insulin related event occurring before the first qualified basal insulin related event.

8. The device of claim 1, wherein the first basal insulin related event is deemed qualified when:
  (i) the subject has taken no correction bolus of the short acting insulin medicament in the twelve hours prior to the first basal insulin related event, and
  (ii) the subject has taken a meal bolus of the short acting insulin medicament with each hypoglycaemic event free meal in the fourteen hours prior to the first fasting event, wherein the occurrence of a correction bolus, a first basal insulin related event, a hypoglycaemic event free meal are identified in the first data set.

9. The device of claim 1, wherein the estimating the bolus insulin sensitivity change in B.2) is computed as:

$$\left( \frac{ISF_{bolus,i,t}}{ISF_{bolus,i-p,t}} \right) = \left( \frac{BG_{expected} - \widehat{BG}_{bolus,corr,i}}{\widehat{BG}_{bolus,corr,i}} + 1 \right),$$

wherein $BG_{expected}$ is the expected blood glucose level ($BG_{expected}$) based on:
  (i) the glucose level ($\widehat{BG}_{bolus,hyp,i}$) of the subject after a meal event, wherein $\widehat{BG}_{bolus,hyp,i}$ is obtained from the portion of the glucose measurements obtained from the first data set that are contemporaneous with a period of time during a hyperglycaemic event after a meal event, and whereby the portion of the glucose measurements is a subset of the measurements that are contemporaneous with the occurrence of the correction bolus with a short acting medicament,
  (ii) the bolus insulin sensitivity estimate ($ISF_{bolus,i-p,t}$) of the subject related to the occurrence of the prior correction bolus with the short acting insulin medicament, and
  (iii) an insulin medicament injection event from the second data set corresponding to the occurrence of the correction bolus, and wherein $\widehat{BG}_{bolus,corr,i}$ is the glucose level ($\widehat{BG}_{bolus,corr,i}$) of the subject after the occurrence of the correction bolus, wherein $\widehat{BG}_{bolus,corr,i}$ is obtained from the portion of the glucose measurements of the first data set that are contemporaneous with a period of time after the occurrence of the correction bolus, and whereby the portion of the glucose measurements is a subset of the measurements that are contemporaneous with the occurrence of the correction bolus with a short acting medicament.

10. The device of claim 9, wherein the expected blood glucose level ($BG_{expected}$) is computed as:

$$BG_{expected} = \widehat{BG}_{bolusl,hyp,i} - ISF_{bolus,i-p,t} U_{bolus,i}.$$

11. A method for estimating parameters in an insulin medicament dosage regimen for a subject that includes both a short acting insulin medicament regimen and a long acting insulin medicament regimen, the method comprising:
  A) obtaining:
    A. 1) a first data set, the first data set comprising a plurality of glucose measurements of the subject taken over a first period of time received autonomously originating from one or more glucose sensors attached to a subject on an ongoing basis and, for each respective glucose measurement in the plurality of glucose measurements, a timestamp representing when the respective measurement was made;
    A. 2) a second data set from one or more insulin pens used by the subject to apply the insulin medicament dosage regimen, the second data set comprises a plurality of insulin medicament records, each insulin medicament record in the plurality of medicament records comprises: (i) a respective insulin medicament injection event including an amount of insulin medicament injected into the subject using a respective insulin pen in the one or more insulin pens (ii) a corresponding electronic timestamp that is automatically generated by the respective insulin pen upon occurrence of the respective insulin medicament injection event, and (iii) a type of insulin medicament, wherein the type of insulin medicament is a short acting insulin medicament or a long acting insulin medicament;

B) determining one or more insulin sensitivity change estimates by:

B. 1) making an estimate of a basal insulin sensitivity change between a basal insulin sensitivity estimate ($ISF_{basil,i,t}$) for the subject related to the occurrence of a first basal insulin related event undertaken by the subject within the first period of time, when the first basal insulin related event is deemed qualified, and a basal insulin sensitivity estimate ($ISF_{basil,i-p,t}$) of the subject related to the occurrence of a qualified basal insulin related event occurring before the first basal insulin related event, wherein the occurrence of the basal insulin related events are identified in the first data set, the estimating using:

(i) the basal insulin sensitivity estimate ($ISF_{basil,i-p,t}$) of the subject related to the occurrence of the qualified basal insulin related event occurring before the first basal insulin related events (ii) glucose measurements from the first data set contemporaneous with the occurrence of the first qualified basal insulin related event, (iii) glucose measurements from the first data set contemporaneous with the occurrence of the qualified basal insulin related event occurring before the first qualified basal insulin related event, (iv) an insulin medicament injection event from the second data set corresponding to the first qualified basal insulin related event, wherein the injection has been applied according to the long acting insulin medicament regimen, and (v) an insulin medicament injection event from the second data set corresponding to the qualified basal insulin related event occurring before the first qualified basal insulin related event, wherein the injection has been applied according to the long acting insulin medicament regimen; and/or B.2) making an estimate of a bolus insulin sensitivity change between a bolus insulin sensitivity estimate ($ISF_{bolus,i,t}$) for the subject relating to the occurrence of a correction bolus with a short acting insulin medicament within the first period of time and a bolus insulin sensitivity estimate ($ISF_{bolus,i-p,t}$) of the subject related to the occurrence of a prior correction bolus with the short acting insulin medicament, wherein the occurrence of the correction bolus and the occurrence of the prior correction bolus are identified in the first data set, the estimating using:

(i) glucose measurements from the first data set contemporaneous with the occurrence of the correction bolus with a short acting medicament, (ii) the bolus insulin sensitivity estimate ($ISF_{bolus,i-p,t}$) of the subject related to the occurrence of a prior correction bolus with the short acting insulin medicament, and (iii) an insulin medicament injection event from the second data set corresponding to the occurrence of the correction bolus and applied according to the short acting insulin medicament regimen; and C) estimating the bolus insulin sensitivity estimate ($ISF_{bolus,i,t}$) as a function of the estimated basal insulin sensitivity change, in response to making an estimate of the basal insulin sensitivity change in B.1); and/or D) estimating the basal insulin sensitivity estimate ($ISF_{basal}$) as a function of the estimated bolus insulin sensitivity change, in response to making an estimate of the bolus insulin sensitivity change in B.2), E) estimating a basal insulin sensitivity factor curve ($ISF_{basal}$) as a function of the estimated basal insulin change, in response to estimating the basal insulin sensitivity change in B.1) and/or in response to estimating the basal insulin sensitivity estimate in D);

F) estimating a bolus insulin sensitivity factor curve ($ISF_{bolus,i}$) as a function of (i) the estimated bolus insulin sensitivity change, in response to estimating the bolus insulin sensitivity change in B2) and/or in response to estimating the bolus insulin sensitivity in C);

G) updating: (i) the bolus insulin sensitivity curve ($ISF_{bolus}$) as a function of the estimated bolus insulin sensitivity factor curve ($ISF_{bolus,i}$) of F) and prior estimated bolus insulin sensitivity factor curves for the subject, and (ii) updating the basal insulin sensitivity curve ($ISF_{basal}$) as a function of the estimated basal insulin sensitivity factor curve ($ISF_{basal,i}$) of E) and prior estimated basal insulin sensitivity factor curves for the subject; and H) providing a recommended dose of the short acting insulin medicament to achieve a target fasting glucose level in the subject by using glucose measurements from a portion of the plurality of glucose measurements and the updated bolus insulin sensitivity curve ($ISF_{bolus}$) or the updated basal insulin sensitivity curve ($ISF_{basal}$), wherein the insulin sensitivity estimates are parameters in the insulin medicament regimen.

* * * * *

UNITED STATES PATENT AND TRADEMARK OFFICE
CERTIFICATE OF CORRECTION

PATENT NO. : 11,195,606 B2
APPLICATION NO. : 16/315820
DATED : December 7, 2021
INVENTOR(S) : Henrik Bengtsson et al.

It is certified that error appears in the above-identified patent and that said Letters Patent is hereby corrected as shown below:

In the Claims

At Column number 55, Claim number 11, please replace Line 28 with the following:
"basal insulin related event"

At Column number 56, Claim number 11, please replace Line 21 with the following:
"($ISF_{basal,i,t}$) as a function of the estimated bolus insulin"

At Column number 56, Claim number 11, please replace Line 24 with the following:
"($ISF_{basal,i}$) as a function of the estimated basal insulin"

Signed and Sealed this
Twenty-fifth Day of October, 2022

*Katherine Kelly Vidal*

Katherine Kelly Vidal
*Director of the United States Patent and Trademark Office*